(12) United States Patent
Zachar

(10) Patent No.: US 9,533,169 B2
(45) Date of Patent: Jan. 3, 2017

(54) APPARATUS AND METHOD FOR IRRADIATING BIOLOGICAL TISSUE

(71) Applicant: Oron Zachar, Tel Aviv (IL)

(72) Inventor: Oron Zachar, Tel Aviv (IL)

(73) Assignee: PRODOLUX SP Z O O, Warsaw (PL)

( * ) Notice: Subject to any disclaimer, the term of this patent is extended or adjusted under 35 U.S.C. 154(b) by 0 days.

(21) Appl. No.: 14/447,630

(22) Filed: Jul. 31, 2014

(65) Prior Publication Data

US 2015/0057736 A1    Feb. 26, 2015

Related U.S. Application Data

(63) Continuation-in-part of application No. PCT/IB2012/050453, filed on Jan. 31, 2012.

(51) Int. Cl.
| | |
|---|---|
| *A61B 18/18* | (2006.01) |
| *A61N 5/04* | (2006.01) |
| *A61N 2/00* | (2006.01) |
| *A61N 2/02* | (2006.01) |
| *A61B 18/00* | (2006.01) |

(52) U.S. Cl.
CPC .............. *A61N 5/04* (2013.01); *A61N 2/006* (2013.01); *A61B 18/1815* (2013.01); *A61B 2018/00321* (2013.01); *A61N 2/02* (2013.01)

(58) Field of Classification Search
CPC ............ A61N 5/04; A61N 2/02; A61N 2/006; A61B 18/1815; A61B 2018/00321
USPC .......................................... 607/88; 600/9, 13
See application file for complete search history.

(56) References Cited

U.S. PATENT DOCUMENTS

2009/0171422 A1* 7/2009 Hillis et al. ..................... 607/88

* cited by examiner

*Primary Examiner* — Carl H Layno
*Assistant Examiner* — Jon Eric C Morales
(74) *Attorney, Agent, or Firm* — Marc Van Dyke; Fourth Dimension IP

(57) ABSTRACT

Methods and apparatus for irradiating biological tissue by EM radiation having radiation frequency(ies) of at most 10 Gigahertz are disclosed herein. In some embodiments, the tissue is irradiated by passing converging EM waves (e.g. generated using an ellipsoidal mirror 110) through a surrogate medium having a specially shaped ENTRY_SURFACE via which the converging EM waves enter the surrogate medium. In some embodiments, a refractive index at a sub-10 Gigahertz of the surrogate medium is at least 2 or at least 3 or at least 5 and/or substantially matches a refractive index of an irradiated biological tissue. In some embodiments, converging EM waves are formed within the surrogate medium. Some embodiments relate to methods and apparatus for irradiating neuron(s), for example, to non-invasively stimulating or otherwise modify a behavior of neuron(s) using focused or non-focused EM radiation.

1 Claim, 38 Drawing Sheets

---

Generate S201 converging EM waves within an 'index-matching' Surrogate medium having a refraction index (i.e. for frequency(ies) less than 2 Gigahertz) that substantially match that of the biological tissue EM waves propagate S205 through the surrogate medium *en route* to the Biological tissue such that the substantially the entire optical path between:
(i) the location where the converging EM waves were generated (i.e. in step S201) and
(ii) a surface of the biological tissue,
is occupied by any 'index-matching' surrogate medium Converging EM waves enter the biological tissue, and propagate S209 within the biological tissue such that EM energy is focused at a target location (e.g. corresponding to *F2*)

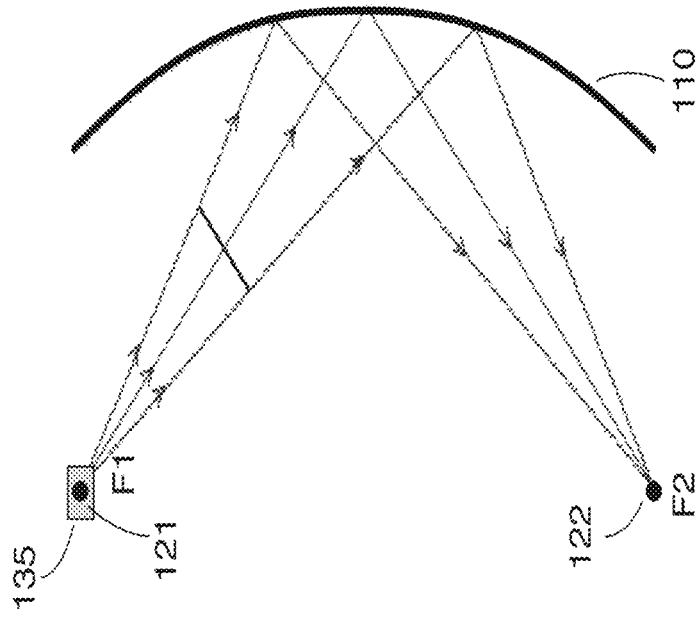
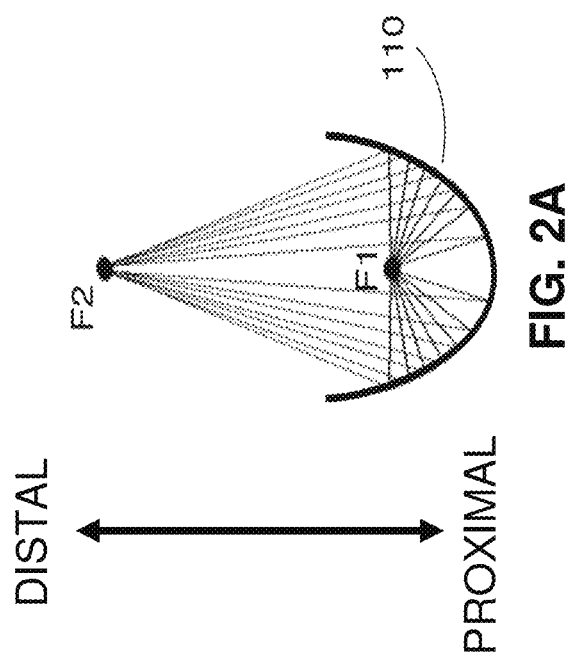
PRIOR ART
FIG. 2A
FIG. 2B

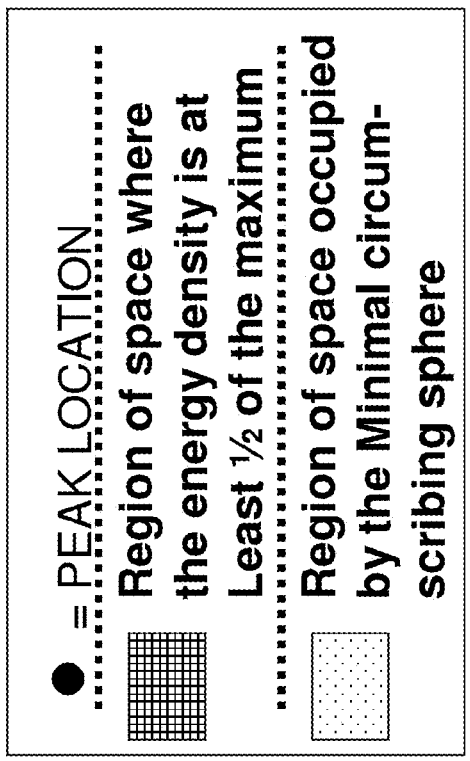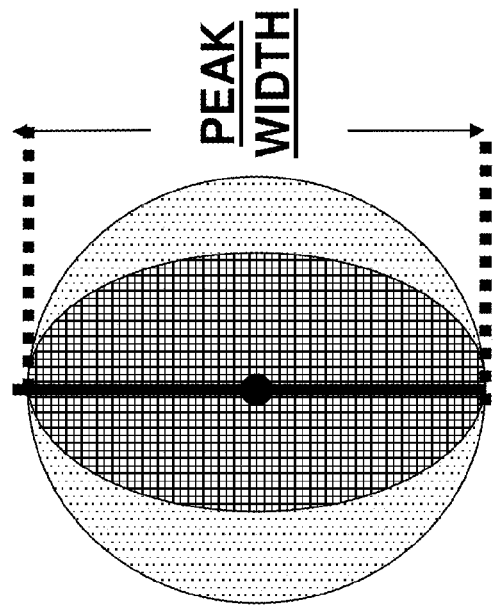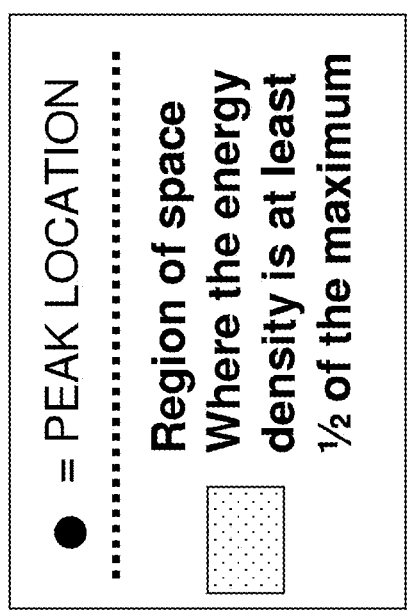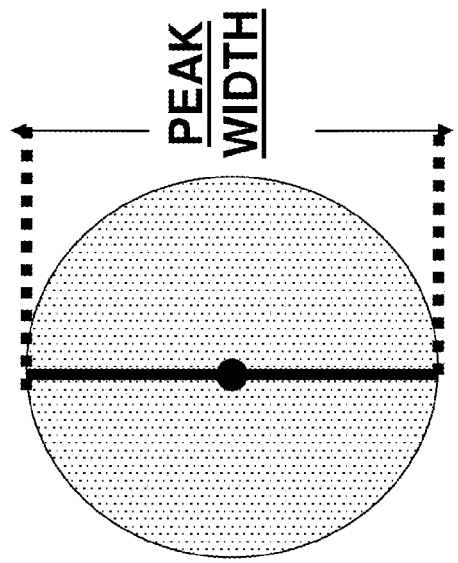
FIG. 7A
FIG. 7B

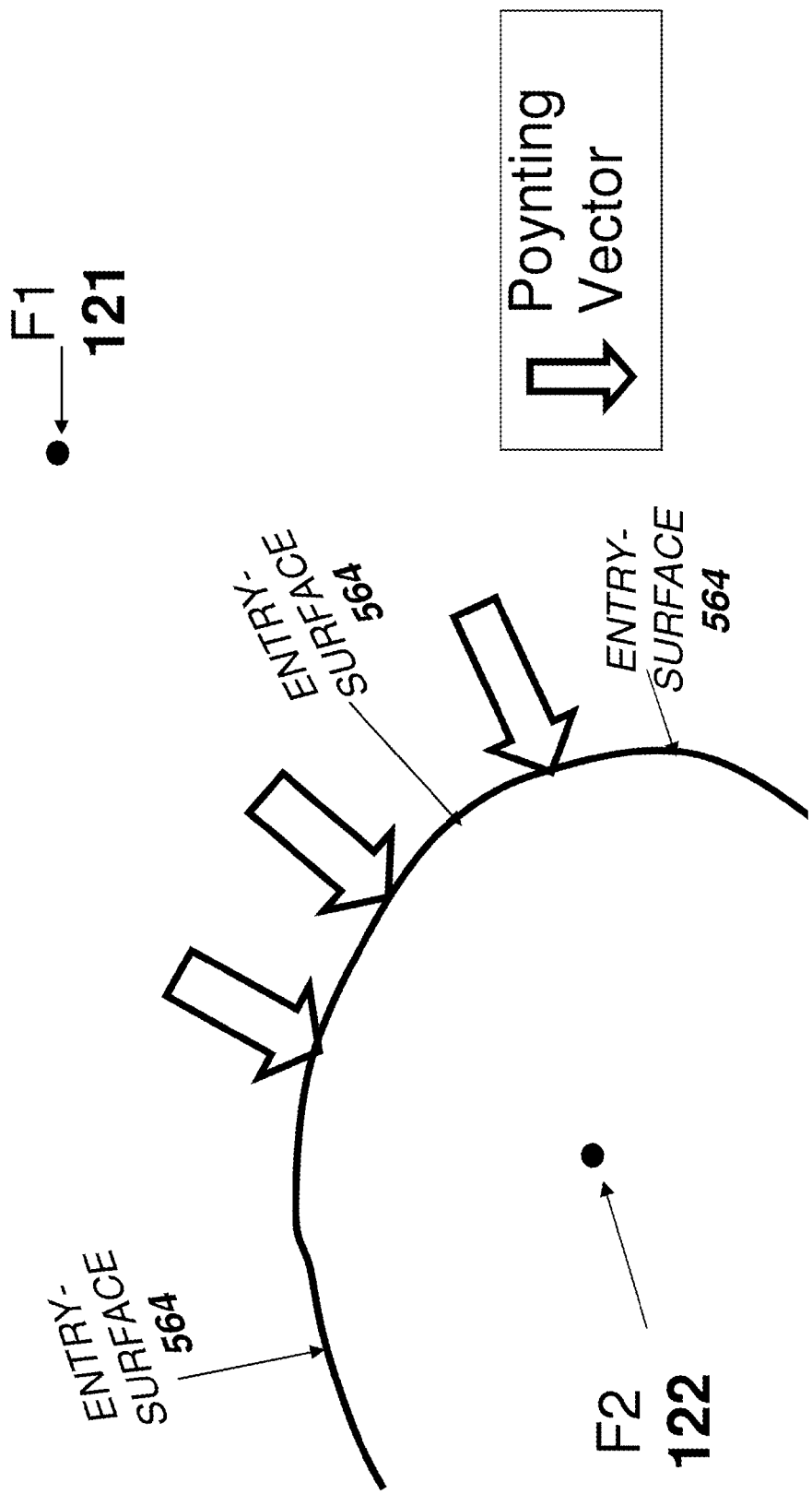

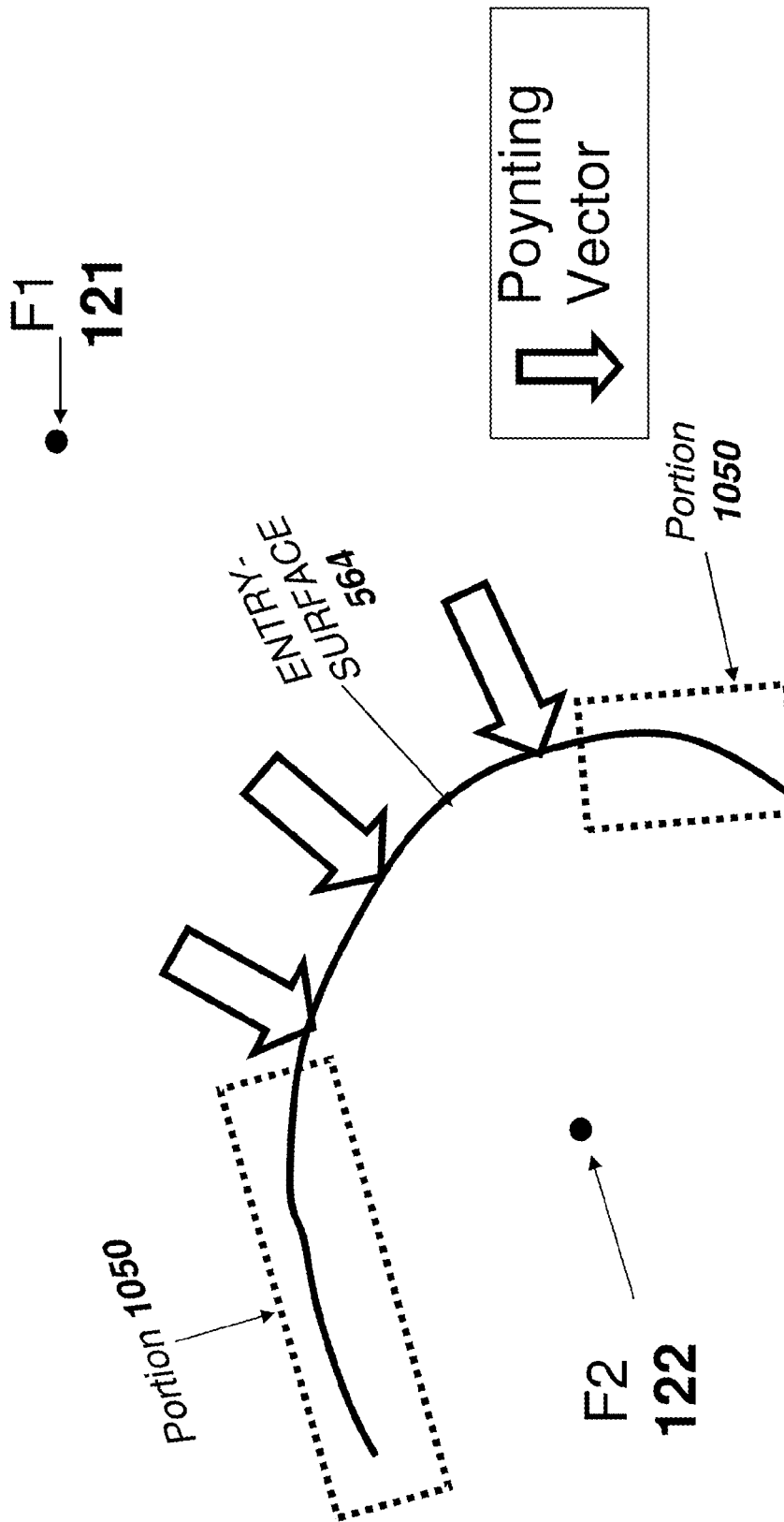

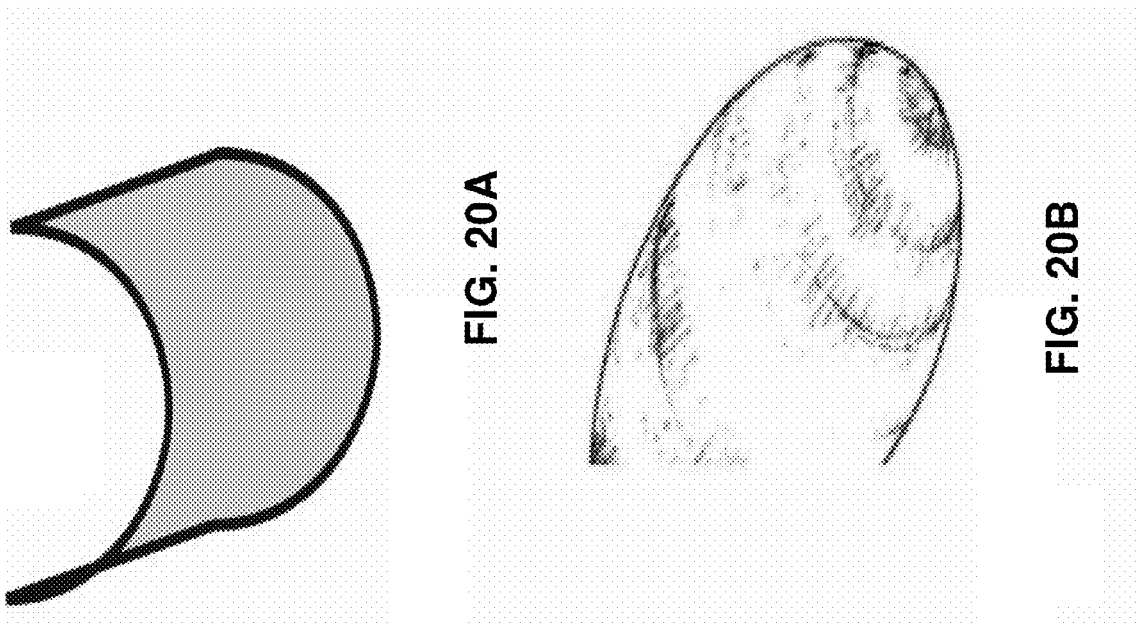

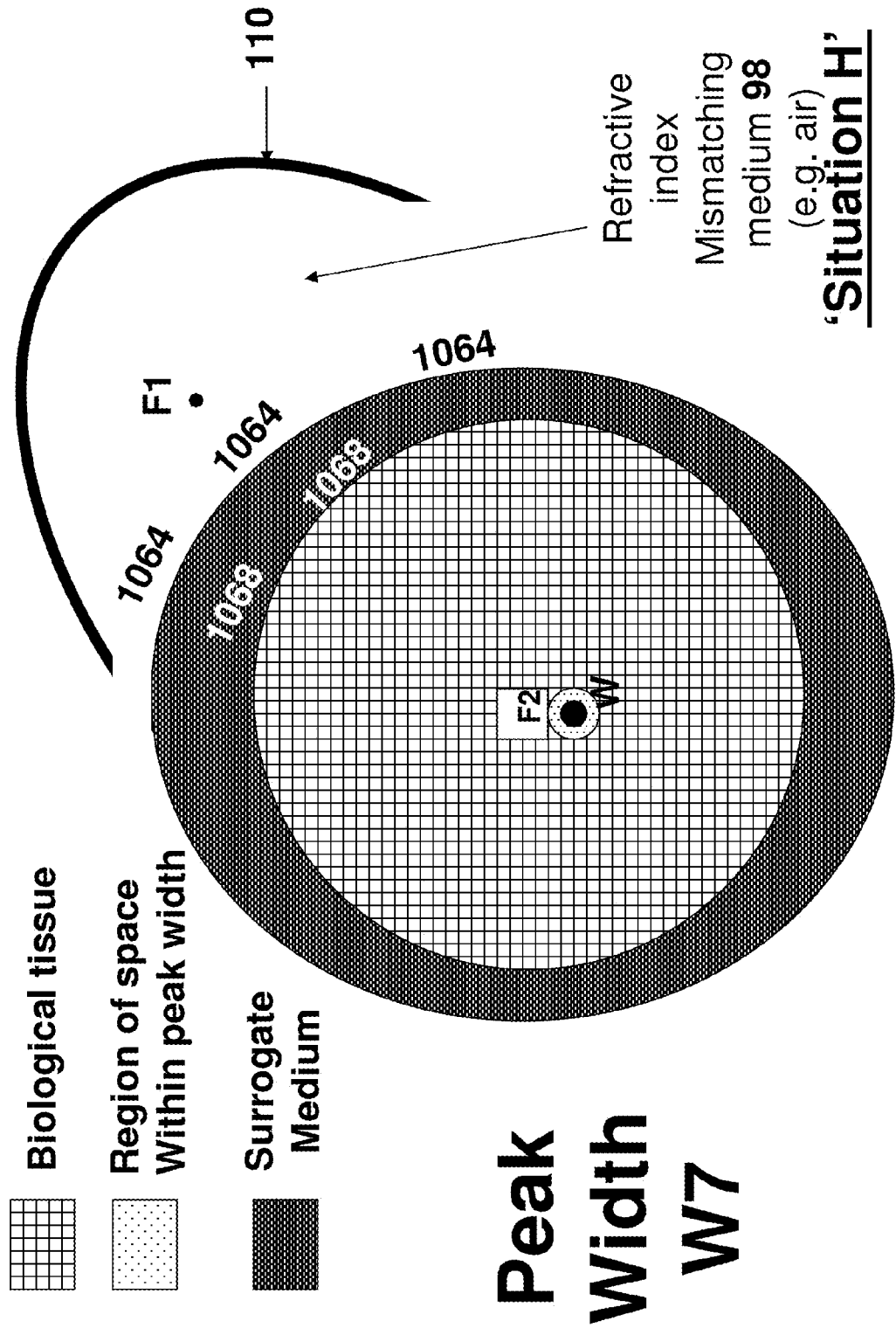

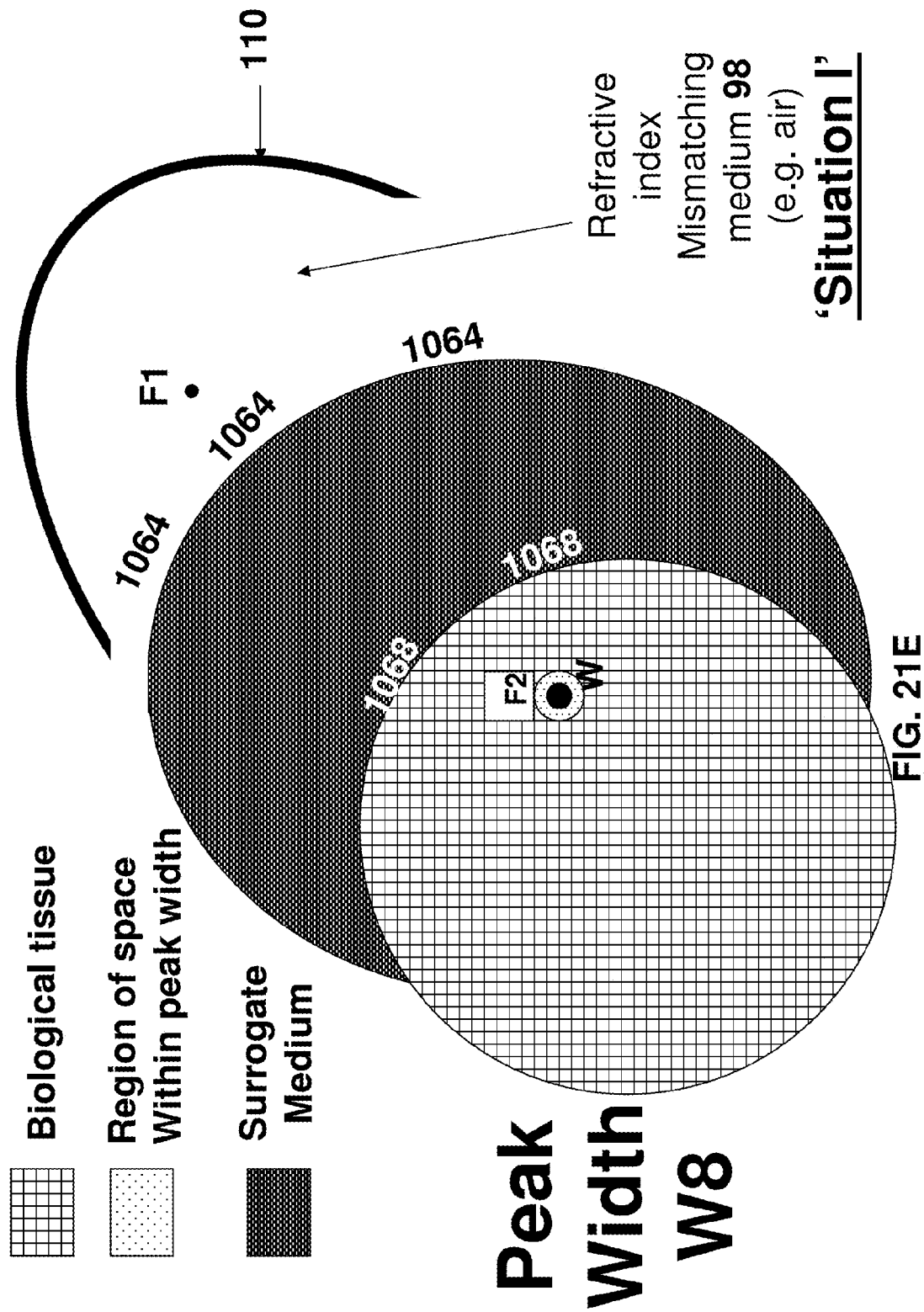

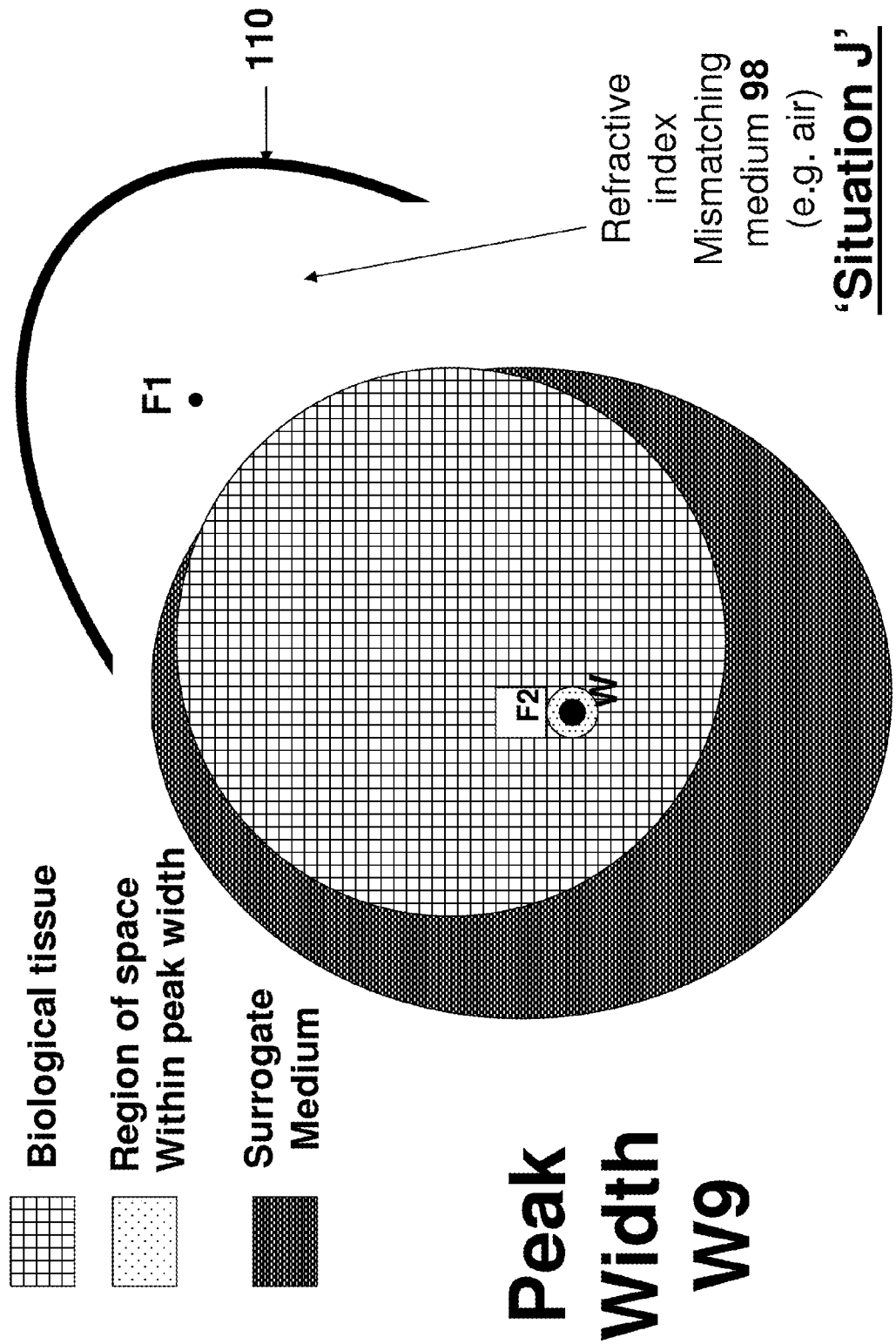

APPARATUS AND METHOD FOR IRRADIATING BIOLOGICAL TISSUE

CROSS-REFERENCE TO RELATED APPLICATIONS

This application is a continuation-in-part of PCT/IB2012/050453 filed on Jan. 31, 2012 (and which published on Aug. 8, 2013 as WO/2013/114156), which is hereby incorporated by reference in its entirety.

FIELD OF THE INVENTION

The present invention relates to apparatus and methods for irradiating biological tissue by converging EM waves and/or for non-invasively stimulating neural tissue by radiation.

BACKGROUND AND RELATED ART

Frequency Dependence of the Dielectric Constant and the Refractive Index

Biological Tissue Vs. Water

Tissue is composed primarily of water. The human body is between 50% and 70% water by weight. FIG. 1, reproduced from Kenneth R. Foster and Herman P. Schwan, "Dielectric properties of tissues and biological materials: a critical review" Crit. Rev. in Biomed. Engr., 17, pp. 25-104, 1989, illustrates the frequency dependence of the dielectric constant $\in$ of dispersion both for biological tissue as well as pure water.

At audio frequencies, the alpha dispersion is dominated by counterion polarization effects. At HF frequencies, the beta dispersion is dominated by interfacial polarization of the cell walls. At radio and microwave frequencies above about 100 MHz, the dispersion characteristics of water and tissue are well matched. This is the so called gamma dispersion where the Debye relaxation of water molecules dominates the dispersion of tissue.

The dielectric constant is simply the square of the (complex) refractive index in a non-magnetic medium (one with a relative permeability of unity). The refractive index is used for optics in Fresnel equations and Snell's law; while the dielectric constant is used in Maxwell's equations and electronics. Where $\tilde{\in}$, $\in_1$, $\in_2$, n, and κ are functions of wavelength:

$$\tilde{\in} = \in_1 + i\in_2 = (n+i\kappa)^2. \quad \text{(Eq. 1)}$$

Conversion between refractive index "n" and dielectric constant $\in$ is carried out by:

$$\epsilon_1 = n^2 - \kappa^2 \quad \text{(Eq. 2)}$$

$$\epsilon_2 = 2n\kappa \quad \text{(Eq. 3)}$$

$$n = \sqrt{\frac{\sqrt{\epsilon_1^2 + \epsilon_2^2} + \epsilon_1}{2}} \quad \text{(Eq. 4)}$$

$$\kappa = \sqrt{\frac{\sqrt{\epsilon_1^2 + \epsilon_2^2} - \epsilon_1}{2}}. \quad \text{(Eq. 5)}$$

In connection with FIG. 1, it is noted that the index of refraction is approximately equal to the real part of the dielectric constant, i.e., n~Re[$\in$], so the verticle axis of FIG. 4 can be regarded also as designating $n^2$.

The known Snell's principle of refraction is that light incoming from medium $n_1$ at an angle $\theta_1$ to the normal of the interface to medium $n_2$ is continuing in medium $n_2$ at angle $\theta_2$ according to $$\frac{\sin\theta_1}{\sin\theta_2} = \frac{v_1}{v_2} = \frac{n_2}{n_1} \quad \text{(Eq 6)}$$

It is clear from FIG. 1 that for frequencies less than 10 Gigahertz, a value of a refractive index of biological tissue is much closer to a refractive index value of water than to the refractive index value of air, which is around 1. In this sense, it may be said that water provides a much better 'match' to biological tissue with respect to refractive index than air, which is much more of a 'mismatching' medium.

Converging EM Waves

It is known in the art that ellipsoidally-shaped reflectors (used interchangeably with 'ellipsoidal reflectors') are useful for generating converging EM waves, and for focusing energy of the same. One salient feature of ellipsoidal reflectors are focal points F1 and F2.

As is illustrated in FIGS. 2A-2B, when EM radiation is transmitted from one of the focus points, at least a portion of the transmitted EM radiation is reflected by the ellipsoidal reflector 110. In theory (i.e. under 'perfect conditions'), and as illustrated in FIGS. 2A-2B, all energy that is reflected by the ellipsoidal reflector 110 passes through the second focus point.

FIG. 3 illustrates a system including a 'theoretical point-source' of EM radiation located exactly at F1 and a 'perfect' ellipsoidal reflector (i.e. no distortions, etc). In the example of FIG. 3, the medium via which EM energy propagates is a theoretically 'perfect' medium. The point-size source exactly at F1 continuously transmits radiation at a constant intensity—at any point in time, the function describing the EM energy density near F1 behaves likes a Dirac delta function around F1.

At least a portion of the transmitted EM energy is reflected by the ellipsoidal mirror and focused onto F2. As noted above, for the pure theoretical case of FIG. 3, the source of radiation is a 'perfect' point-source, and the ellipsoidal mirror and the medium via which EM energy are 'perfect' and free of distortion. As such, (i) all energy which is reflected by the ellipsoidal mirror is converted into converging EM waves having a perfectly-circular wave front; (ii) all energy which is reflected by the ellipsoidal mirror passes through the point F2; and (iii) the EM energy density around F2 is a perfect reflection of the energy intensity density around F1 and may also be described by a Dirac delta function.

This 'pure theory case' is also described in the flow chart of FIG. 4. In step S101A, EM radiation transmitted from point F1 propagates away from point F1 in a perfect medium as a diverging wave front. In step S105A, at least a portion of this EM radiation is reflected by the perfect ellipsoidal reflector to form converging EM waves whose wave front has a perfectly circular shape. In step S109, these converging EM waves propagate through free space. In step S113, 100% of the energy of the converging EM waves passes through the second focus—i.e. point F2.

In practice, many of the aforementioned assumptions of the 'pure theory case' are not valid. In practice, the EM radiation source is not a point source, the medium via which the EM radiation propagates is not perfect (e.g. there is energy loss, dispersion of energy, or other imperfections which may distort a wavefront shape) and the ellipsoidal mirror is also not perfect. For example, when converging EM waves propagate through a region of space characterized by non-uniform optical properties, this may contribute to distortion of a wave front shape.

FIG. 5 illustrates a 'real-life' system comprising a source of EM radiation (not a point source as in FIG. 3), and an elliptical reflector 110 which may include 'imperfections.' In contrast to the example of FIG. 3 where the region of space outside of the EM radiation source and the reflector is considered a 'perfect non-attenuating medium,' this is not case for the 'real-life' example of FIG. 3—the medium is not 'perfect.'

Due to any combination of these 'imperfections,' in real-world systems (e.g. FIG. 5), many conclusions that were reached with respect to the 'pure theory' example of FIG. 3 are not true in 'real-world' systems. Thus, in contrast to the 'pure theory' example of FIG. 3, in real-world systems, (i) 100% of the energy does not pass through the point F2, (ii) the 'peak location' of maximum intensity of energy density will be not located exactly at F2 but rather is offset from F2 by some 'offset distance'; and (iii) the energy density around 'peak location' is not be described by a Dirac delta function but may, to first order, be approximately described by some sort of Gaussian distribution having a finite peak width.

FIG. 6 illustrates a Gaussian-like peak centered around 0. FIG. 6 describes, for a symmetric one-dimensional case, the variation of energy intensity as a function of the distance from the 'peak location.' At the 'peak location,' the intensity function (in our case, representing 'energy density') reaches a maximum. Moving away from the peak location in either direction, the intensity function decreases. For the one-dimensional example of FIG. 6, the 'peak width' is characterized by the distance between the two points where the intensity is one half of the maximum.

For the present disclosure, for a particular EM frequency, the 'peak location' is the location where the energy density of EM energy of the particular frequency reaches its maximum.

For situations where the energy intensity function is radially-symmetric, the one-dimensional symmetric case provides an adequate description of how energy density behaves at and near the peak location. This is illustrated in FIG. 7A where region of space where the energy density exceeds one half of its maximum is shaded using the 'light shading.' In FIG. 7A, this region of space is shaped like a sphere, and the peak width is the diameter of this sphere.

In the example of FIG. 7B, there is no radial symmetry, and the region of space where the energy density exceeds one half of its maximum (now shaded using the 'dark shading') is non-spherical. It is, however, possible to determine a minimally-circumscribing sphere which circumscribes the region of space where the energy density exceeds one half of its maximum. The volume within this 'circumscribing sphere' is shaded using the 'light shading.'

Thus, for the present disclosure, a 'peak location' is the location of the maximum energy density, and the 'peak width' is the diameter of the minimally-sized circumscribing sphere whose center coincides with the peak location (i.e. location of the maximum energy density) and which completely circumscribes the region of space where the energy intensity is at least one half of the maximum.

In one non-limiting example where the (i) EM radiation source is a circular or 'loop' radiation source having a diameter of about 1 cm and a center that corresponds with F1 within a few millimeters; (ii) the distance between F1 and F2 is about 40 cm; and (iii) the EM radiation propagates through air, the energy density distribution near F2 will be a 'close to perfect' image of the energy distribution near F1. In this example, the peak width will be at F2 (within a tolerance of a few millimeters) and the 'peak width' will be around 1 cm (within a tolerance of a few millimeters). This case would correspond to the situation of FIG. 7B—the energy distribution near the peak location would not necessarily have radial symmetry.

FIG. 4, describes above, is a flow chart describing how the 'theoretical system' of FIG. 3 operates. FIG. 8 is a flow chart for the corresponding 'real world' system of FIG. 5. In step S101B, EM radiation transmitted from location(s) near F1—the transmitted EM radiation propagates away from point F1 in a perfect medium as a diverging wave front. In contrast to what prevailed in the 'pure theory' case of FIGS. 3-4 (see step S101A), in the case of step S101B the diverging EM waves do not produce a wave front whose shape is exactly a perfect sphere. In step S105B, at least a portion of this EM radiation is reflected by the perfect ellipsoidal reflector to form converging EM waves whose wave front—once again, the wave front shape will not be a perfect sphere. In step S117, the converging EM waves produce a convergence peak whose maximum intensity is at or near F2 and which has a finite peak width.

FIG. 9 illustrates an ellipsoidal reflector including a plurality of voids 108. This may also be used to generate converging EM waves.

Although the aforementioned examples related to the specific case of an ellipsoidal reflector, the skilled artisan will appreciate that converging EM waves may be formed using other devices—see, for example, U.S. Pat. No. 5,097,844 which is incorporated herein by reference in its entirety.

Although the aforementioned examples related to the specific case of converging EM waves having a nearly-spherical wave front, the skilled artisan appreciates that converging EM waves may be associated with wave fronts of other shapes, including but not limited to circular, quasi-circular, and quasi-cylindrical.

SUMMARY OF EMBODIMENTS

Some embodiments relate to methods and apparatus of irradiating biological tissue by sub-10 GHz radiation to form a relatively narrow intensity peak within the tissue even for locations that are relatively deep within the biological tissue. Some embodiments relate to method and apparatus for irradiating neural tissue—for example, at one or more resonant frequencies of the neural tissue or cell(s) thereof. Although the radiation at the resonant frequency(ies) may be focused, and in some embodiments it is preferred to do so, this is not a requirement.

Some embodiments relate to both features—focused radiation at resonant frequency(ies) of the neural tissue.

In some embodiments, an apparatus and methods for irradiating biological tissue is disclosed. EM radiation having radiation frequency(ies) that are less than 10 Gigahertz is focused upon a target location situated beneath a surface of the tissue so as to generate a relatively narrow and localized intensity peak around the target location. In some embodiments, even for relatively deep locations, it is possible to achieve a high degree of focus despite the refractive-index mismatch between biological tissue and air outside of the tissue.

It is now disclosed a system for irradiating biological tissue comprising:
a. an ellipsoidal reflector having foci F1 and F2 separated from each other by at least an F1-F2 separation distance of at least 5 cm; b. a source of EM radiation configured to emit diverging EM waves of sub-10 GHz EM radiation, at least some of which are reflected by the ellipsoidal reflector to form converging EM waves having one or more sub-10 GHz radiation frequency(ies); and c. a surrogate medium having an ENTRY_SURFACE via which converging EM waves enter the surrogate medium, wherein for a selected one or more of sub-10 GHz radiation frequency(ies) of the sub-10 GHz EM radiation, i. an average refractive index $n^{AVERAGE}_{SURROGATE\_MEDIUM}$ of the surrogate medium equals at least a minimum refractive-index threshold value that is at least 2; ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and iii. for all locations on the power-significant portion of the ENTRY_SURFACE: A. a local normal line passes within an F2-tolerance-distance from F2, the F2 tolerance-distance being at most 1 cm and/or B. a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising: a. a converging EM wave source of converging waves of EM radiation at sub-10 GHz frequency(ies); and b. a surrogate medium having an ENTRY SURFACE through which the converging waves enter into the surrogate medium, wherein for a selected one or more of sub-10 GHz radiation frequency(ies) of the sub-10 GHz EM radiation i. an average refractive index $n^{AVERAGE}_{SURROGATE\_MEDIUM}$ of the surrogate medium equals at least a minimum refractive-index threshold value that is at least 2; ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and iii. for every location on the power-significant portion of the ENTRY_SURFACE, a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising: a. a converging EM wave source of converging waves of EM radiation at sub-10 GHz frequency(ies); and b. a surrogate medium having an ENTRY SURFACE through which the converging waves enter into the surrogate medium, wherein, wherein for a selected one or more of sub-10 GHz radiation frequency(ies) of the sub-10 GHz EM radiation: i. an average refractive index $n^{AVERAGE}_{SURROGATE\_MEDIUM}$ of the surrogate medium equals at least a minimum refractive-index threshold value that is at least 2; ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; iii. before entering the surrogate medium via the ENTRY_SURFACE, the EM radiation at the selected frequency(ies) has focused at an initial focus location IFL; and iii. for all locations on the power-significant portion of the ENTRY_SURFACE, a local normal line passes within an IFL-tolerance-distance from the initial focus location IFL, the IFL-tolerance-distance being at most 1 cm.

It is now disclosed a method for irradiating biological tissue, the method comprising: a. providing an ellipsoidal reflector and a surrogate medium, the ellipsoidal reflector being shaped as an ellipsoidal section and having proximal and distal foci F1 and F2 that are separated from each other by at least an F1-F2 separation distance of at least 5 cm, the surrogate medium including an ENTRY-SURFACE including one or more OP-oriented portions(s) that are oriented relative to an orientation point OP such that a local normal of all locations in the region(s) within an OP tolerance distance that is at most 1 cm; b. determining a target location within the biological tissue at a target depth beneath the surface of the biological tissue; c. in accordance with the determined target depth and/or target location, positioning and/or orienting and/or configuring: i. an F2 location of the ellipsoidal reflector relative to the biological tissue; and ii. the OP-oriented portion(s) of the ENTRY SURFACE relative to the biological tissue; d. reflecting sub-10 GHz EM radiation from the ellipsoidal reflector so as to form converging EM waves of sub-10 GHz EM radiation wherein for a selected one or more of sub-10 GHz radiation frequency(ies) of the sub-10 GHz EM radiation: i. an entry-surface-power-significant-fraction ESPSF equal to at least 0.1 by power of the converging waves enters the surrogate medium via one of the OP-oriented portion(s) of the ENTRY SURFACE, traverses the surrogate medium, exits the surrogate medium, and enters into the biological tissue so as to irradiate the biological tissue; ii. respective average refractive indexes $n^{AVERAGE}_{SURROGATE\_MEDIUM}$ and $n^{AVERAGE}_{BIOLOGICAL\_TISSUE}$ of the surrogate medium and the biological tissue in respective regions via which the EM waves travel en route to the target location, are substantially equal to each other within a medium-tissue tolerance that is at most 50%.

It is now disclosed a method for irradiating biological tissue, the method comprising:
 a. providing an ellipsoidal reflector and a surrogate medium, the ellipsoidal reflector being shaped as an ellipsoidal section and having proximal and distal foci F1 and F2 that are separated from each other by at least an F1-F2 separation distance of at least 5 cm, the surrogate medium including an ENTRY-SURFACE including one or more OP-oriented portions(s) that are oriented relative to an orientation point OP such that a local normal of all locations in the region(s) within an OP tolerance distance that is at most 1 cm;
 b. determining a target location within the biological tissue at a target depth beneath the surface of the biological tissue;
 c. in accordance with the determined target depth and/or target location, positioning and/or orienting and/or configuring:
    i. an F2 location of the ellipsoidal reflector relative to the biological tissue; and
    ii. the OP-oriented portion(s) of the ENTRY SURFACE relative to the biological tissue;
 d. reflecting sub-10 GHz EM radiation from the ellipsoidal reflector so as to form converging EM waves of sub-10 GHz EM radiation wherein for a selected one or more of sub-10 GHz radiation frequency(ies) of the sub-10 GHz EM radiation:
    i. an entry-surface-power-significant-fraction ESPSF equal to at least 0.1 by power of the converging waves enters the surrogate medium via one of the OP-oriented portion(s) of the ENTRY SURFACE, traverses the surrogate medium, exits the surrogate medium, and enters into the biological tissue so as to irradiate the biological tissue;

ii. respective average refractive indexes $n^{AVERAGE}_{SURROGATE\_MEDIUM}$ and $n^{AVERAGE}_{BIOLOGICAL\_TISSUE}$ of the surrogate medium and the biological tissue in respective regions via which the EM waves travel en route to the target location, are substantially equal to each other within a medium-tissue tolerance that is at most 50%.

It is now disclosed a method for irradiating biological tissue, the method comprising:

a. providing converging EM wave source and a surrogate medium, the surrogate medium including an ENTRY-SURFACE including one or more OP-oriented portions(s) that are oriented relative to an orientation point OP such that a local normal of all locations in the region(s) within an OP tolerance distance that is at most 1 cm;

b. determining a target location within the biological tissue at a target depth beneath the surface of the biological tissue;

c. in accordance with the determined target depth and/or target location"
  i. setting a focus location of the converging EM wave source beneath a surface of the biological tissue; and
  ii. positioning and/or orienting and/or configuring the OP-oriented portion(s) of the ENTRY SURFACE relative to the biological tissue;

d. generating converging EM waves by the converging EM wave source such that, for a selected one or more of sub-10 GHz radiation frequency(ies) of the sub-10 GHz EM radiation:
  i. an entry-surface-power-significant-fraction ESPSF equal to at least 0.1 by power of the converging waves enters the surrogate medium via one of the OP-oriented portion(s) of the ENTRY SURFACE, traverses the surrogate medium, exits the surrogate medium, and enters into the biological tissue so as to irradiate the biological tissue;
  ii. respective average refractive indexes $n^{AVERAGE}_{SURROGATE\_MEDIUM}$ and $n^{AVERAGE}_{BIOLOGICAL\_TISSUE}$ of the surrogate medium and the biological tissue in respective regions via which the EM waves travel en route to the target location, are substantially equal to each other within a medium-tissue tolerance that is at most 50%.

It is now disclosed a system for irradiating biological tissue comprising:

a. an ellipsoidal reflector having foci F1 and F2 separated from each other by at least an F1-F2 separation distance of at least 5 cm;

b. a source of EM radiation configured to emit diverging EM waves of sub-10 GHz EM radiation, at least some of which are reflected by the ellipsoidal reflector to form converging EM waves having one or more sub-10 GHz radiation frequency(ies); and c. a surrogate medium having an ENTRY_SURFACE via which converging EM waves enter the surrogate medium, wherein for a selected one or more of sub-10 GHz radiation frequency(ies) of the sub-10 GHz EM radiation,
  i. an average refractive index $n^{AVERAGE}_{SURROGATE\_MEDIUM}$ of the surrogate medium equals at least a minimum refractive-index threshold value that is at least 2;
  ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
  iii. a position and/or orientation and/or configuration of the power-significant portion of the ENTRY_SURFACE is mechanically constrained relative to the ellipsoidal reflector so that for all locations on the power-significant portion of the ENTRY_SURFACE:
    A. a local normal line passes within an F2-tolerance-distance from F2, the F2-tolerance-distance being at most 1 cm and/or
    B. a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:

a. a converging EM wave source of converging waves of EM radiation at sub-10 GHz frequency(ies); and b. a surrogate medium having an ENTRY SURFACE through which the converging waves enter into the surrogate medium, wherein for a selected one or more of sub-10 GHz radiation frequency(ies) of the sub-10 GHz EM radiation
  i. an average refractive index $n^{AVERAGE}_{SURROGATE\_MEDIUM}$ of the surrogate medium equals at least a minimum refractive-index threshold value that is at least 2;
  ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
  iii. a position and/or orientation and/or configuration of the power-significant portion of the ENTRY_SURFACE is mechanically constrained relative to the ellipsoidal reflector so that for every location on the power-significant portion of the ENTRY_SURFACE, a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:

a. a converging EM wave source of converging waves of EM radiation at sub-10 GHz frequency(ies); and b. a surrogate medium having an ENTRY SURFACE through which the converging waves enter into the surrogate medium, wherein, wherein for a selected one or more of sub-10 GHz radiation frequency(ies) of the sub-10 GHz EM radiation:
  i. an average refractive index $n^{AVERAGE}_{SURROGATE\_MEDIUM}$ of the surrogate medium equals at least a minimum refractive-index threshold value that is at least 2;
  ii. the ENTRY_SURFACE includes a power-significant portion via which an entry-surface-power-significant-cant-fraction ESPSF equal to at least 0.1 by power of the converging waves of EM radiation at the sub-10 GHz selected frequency(ies) enter the surrogate medium;
iii. before entering the surrogate medium via the ENTRY_SURFACE, the EM radiation at the selected frequency(ies) has focused at an initial focus location IFL; and
iii. a position and/or orientation and/or configuration of the power-significant portion of the ENTRY_SURFACE is mechanically constrained relative to the ellipsoidal reflector so that for all locations on the power-significant portion of the ENTRY_SURFACE, a local normal line passes within an IFL-tolerance-distance from the initial focus location IFL, the IFL-tolerance-distance being at most 1 cm.

It is now disclosed a system for irradiating biological tissue comprising:
a. an ellipsoidal reflector having foci F1 and F2 separated from each other by at least an F1-F2 separation distance of at least 5 cm;
b. a source of EM radiation configured to emit diverging EM waves of sub-10 GHz EM radiation, at least some of which are reflected by the ellipsoidal reflector to form converging EM waves having one or more sub-10 GHz radiation frequency(ies); and
c. a surrogate medium having an ENTRY_SURFACE via which converging EM waves enter the surrogate medium, wherein for a selected one or more of sub-10 GHz radiation frequency(ies) of the sub-10 GHz EM radiation,
  i. an average refractive index $n^{AVERAGE}_{SURROGATE\_MEDIUM}$ of the surrogate medium equals at least a minimum refractive-index threshold value that is at least 2;
  ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
  iii. for all locations on the power-significant portion of the ENTRY_SURFACE:
    A. a local normal line passes within an F2-tolerance-distance from F2, the F2-tolerance-distance being at most 1 cm and/or
    B. a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:
a. a converging EM wave source of converging waves of EM radiation at sub-10 GHz frequency(ies); and
b. a surrogate medium having an ENTRY SURFACE through which the converging waves enter into the surrogate medium, wherein for a selected one or more of sub-10 GHz radiation frequency(ies) of the sub-10 GHz EM radiation
  i. an average refractive index $n^{AVERAGE}_{SURROGATE\_MEDIUM}$ of the surrogate medium equals at least a minimum refractive-index threshold value that is at least 2;
  ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
  iii. for every location on the power-significant portion of the ENTRY_SURFACE, a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:
a. a converging EM wave source of converging waves of EM radiation at sub-10 GHz frequency(ies); and
b. a surrogate medium having an ENTRY SURFACE through which the converging waves enter into the surrogate medium, wherein,
wherein for a selected one or more of sub-10 GHz radiation frequency(ies) of the sub-10 GHz EM radiation:
  i. an average refractive index $n^{AVERAGE}_{SURROGATE\_MEDIUM}$ of the surrogate medium equals at least a minimum refractive-index threshold value that is at least 2;
  ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium;
  iii. before entering the surrogate medium via the ENTRY_SURFACE, the EM radiation at the selected frequency(ies) has focused at an initial focus location IFL; and
  iii. for all locations on the power-significant portion of the ENTRY_SURFACE, a local normal line passes within an IFL-tolerance-distance from the initial focus location IFL, the IFL-tolerance-distance being at most 1 cm,
wherein the surrogate medium has an ENTRY SURFACE through which the converging waves enter into the surrogate medium, and the EXIT SURFACE includes a movable location on the F1-F2 line segment between foci F1 and F2 that is movable relative to the power-significant portion of the ENTRY SURFACE over a range of at least 0.5 cm or at least 1 cm or at least 2 cm along the F1-F2 line segment.

It is now disclosed a system for irradiating biological tissue comprising:
a. an ellipsoidal reflector having foci F1 and F2 separated from each other by at least an F1-F2 separation distance of at least 5 cm;
b. a source of EM radiation configured to emit diverging EM waves of sub-10 GHz EM radiation, at least some of which are reflected by the ellipsoidal reflector to form converging EM waves having one or more sub-10 GHz radiation frequency(ies); and
c. a surrogate medium having an ENTRY_SURFACE via which converging EM waves enter the surrogate medium, wherein for a selected one or more of sub-10 GHz radiation frequency(ies) of the sub-10 GHz EM radiation,
  i. an average refractive index $n^{AVERAGE}_{SURROGATE\_MEDIUM}$ of the surrogate medium equals at least a minimum refractive-index threshold value that is at least 2;
  ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
iii. for all locations on the power-significant portion of the ENTRY_SURFACE:
A. a local normal line passes within an F2-tolerance-distance from F2, the F2-tolerance-distance being at most 1 cm and/or
B. a local Poynting vector of converging EM waves at the selected frequency(ies) is substantially normal to the ENTRY_SURFACE at the location within an angular deviation tolerance that is at most 10 degrees,
wherein the surrogate medium has an ENTRY_SURFACE through which the converging waves enter into the surrogate medium, and an exit surface power-significant-fraction EXS_PF equal to at least 0.1 of the ellipsoidal-reflector-formed converging EM waves at the selected frequency(ies) exit the surrogate medium via a exit-surface-power-significant portion of the EXIT_SURFACE, and the exit-surface-power-significant portion of the EXIT_SURFACE is convex and/or substantially flat.

It is now disclosed a system for irradiating biological tissue comprising:
a. a converging EM wave source of converging waves of EM radiation at sub-10 GHz frequency(ies); and
b. a surrogate medium having an ENTRY SURFACE through which the converging waves enter into the surrogate medium, wherein for a selected one or more of sub-10 GHz radiation frequency(ies) of the sub-10 GHz EM radiation
i. an average refractive index $n^{AVERAGE}_{SURROGATE\_MEDIUM}$ of the surrogate medium equals at least a minimum refractive-index threshold value that is at least 2;
ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
iii. for every location on the power-significant portion of the ENTRY_SURFACE, a local Poynting vector of converging EM waves at the selected frequency(ies) is substantially normal to the ENTRY_SURFACE at the location within an angular deviation tolerance that is at most 10 degrees,
wherein the surrogate medium has an ENTRY_SURFACE through which the converging waves enter into the surrogate medium, and an exit surface power-significant-fraction EXS_PF equal to at least 0.1 of the ellipsoidal-reflector-formed converging EM waves at the selected frequency(ies) exit the surrogate medium via a exit-surface-power-significant portion of the EXIT_SURFACE, and the exit-surface-power-significant portion of the EXIT_SURFACE is convex and/or substantially flat.

It is now disclosed a system for irradiating biological tissue comprising:
a. a converging EM wave source of converging waves of EM radiation at sub-10 GHz frequency(ies); and
b. a surrogate medium having an ENTRY SURFACE through which the converging waves enter into the surrogate medium, wherein,
wherein for a selected one or more of sub-10 GHz radiation frequency(ies) of the sub-10 GHz EM radiation:
i. an average refractive index $n^{AVERAGE}_{SURROGATE\_MEDIUM}$ of the surrogate medium equals at least a minimum refractive-index threshold value that is at least 2;
ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium;
iii. before entering the surrogate medium via the ENTRY_SURFACE, the EM radiation at the selected frequency(ies) has focused at an initial focus location IFL; and
iii. for all locations on the power-significant portion of the ENTRY_SURFACE, a local normal line passes within an IFL-tolerance-distance from the initial focus location IFL, the IFL-tolerance-distance
wherein the surrogate medium has an ENTRY SURFACE through which the converging waves enter into the surrogate medium, and an exit surface power-significant-fraction EXS_PF equal to at least 0.1 of the ellipsoidal-reflector-formed converging EM waves at the selected frequency(ies) exit the surrogate medium via a exit-surface-power-significant portion of the EXIT_SURFACE, and the exit-surface-power-significant portion of the EXIT_SURFACE is convex and/or substantially flat.

It is now disclosed a system for irradiating biological tissue comprising:
a. an ellipsoidal reflector having foci F1 and F2 separated from each other by at least an F1-F2 separation distance of at least 5 cm;
b. a source of EM radiation configured to emit diverging EM waves of sub-10 GHz EM radiation, at least some of which are reflected by the ellipsoidal reflector to form converging EM waves having one or more sub-10 GHz radiation frequency(ies); and
c. a surrogate medium having an ENTRY_SURFACE via which converging EM waves enter the surrogate medium, wherein for a selected one or more of sub-10 GHz radiation frequency(ies) of the sub-10 GHz EM radiation,
i. an average refractive index $n^{AVERAGE}_{SURROGATE\_MEDIUM}$ of the surrogate medium equals at least a minimum refractive-index threshold value that is at least 5;
ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
iii. for all locations on the power-significant portion of the ENTRY_SURFACE:
A. a local normal line passes within an F2-tolerance-distance from F2, the F2-tolerance-distance being at most 1 cm and/or
B. a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:
  a. a converging EM wave source of converging waves of EM radiation at sub-10 GHz frequency(ies); and
  b. a surrogate medium having an ENTRY SURFACE through which the converging waves enter into the surrogate medium, wherein for a selected one or more of sub-10 GHz radiation frequency(ies) of the sub-10 GHz EM radiation
    i. an average refractive index $n^{AVERAGE}_{SURROGATE\_MEDIUM}$ of the surrogate medium equals at least a minimum refractive-index threshold value that is at least 5;
    ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
    iii. for every location on the power-significant portion of the ENTRY_SURFACE, a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:
  a. a converging EM wave source of converging waves of EM radiation at sub-10 GHz frequency(ies); and
  b. a surrogate medium having an ENTRY SURFACE through which the converging waves enter into the surrogate medium, wherein,
  wherein for a selected one or more of sub-10 GHz radiation frequency(ies) of the sub-10 GHz EM radiation:
    i. an average refractive index $n^{AVERAGE}_{SURROGATE\_MEDIUM}$ of the surrogate medium equals at least a minimum refractive-index threshold value that is at least 5;
    ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium;
    iii. before entering the surrogate medium via the ENTRY_SURFACE, the EM radiation at the selected frequency(ies) has focused at an initial focus location IFL; and
    iii. for all locations on the power-significant portion of the ENTRY_SURFACE, a local normal line passes within an IFL-tolerance-distance from the initial focus location IFL, the IFL-tolerance-distance being at most 1 cm.

It is now disclosed a system for irradiating biological tissue comprising:
  a. an ellipsoidal reflector having foci F1 and F2 separated from each other by at least an F1-F2 separation distance of at least 5 cm;
  b. a source of EM radiation configured to emit diverging EM waves of sub-10 GHz EM radiation, at least some of which are reflected by the ellipsoidal reflector to form converging EM waves having one or more sub-10 GHz radiation frequency(ies); and
  c. substantially incompressible flowable surrogate medium bounded by an ENTRY SURFACE via which converging EM waves enter the surrogate medium, the flowable medium being retained within a container having a deformable and/or elastic surface(s), wherein for a selected one or more of sub-10 GHz radiation frequency(ies) of the sub-10 GHz EM radiation,
    i. an average refractive index $n^{AVERAGE}_{SURROGATE\_MEDIUM}$ of the surrogate medium equals at least a minimum refractive-index threshold value that is at least 2;
    ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
    iii. for all locations on the power-significant portion of the ENTRY_SURFACE:
      A. a local normal line passes within an F2-tolerance-distance from F2, the F2-tolerance-distance being at most 1 cm and/or
      B. a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:
  a. a converging EM wave source of converging waves of EM radiation at sub-10 GHz frequency(ies); and
  b. a substantially incompressible flowable surrogate medium bounded by an ENTRY SURFACE via which converging EM waves enter the surrogate medium, the flowable medium being retained within a container having a deformable and/or elastic surface(s), wherein for a selected one or more of sub-10 GHz radiation frequency(ies) of the sub-10 GHz EM radiation
    i. an average refractive index $n^{AVERAGE}_{SURROGATE\_MEDIUM}$ of the surrogate medium equals at least a minimum refractive-index threshold value that is at least 2;
    ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium; and
    iii. for every location on the power-significant portion of the ENTRY_SURFACE, a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:
  a. a converging EM wave source of converging waves of EM radiation at sub-10 GHz frequency(ies); and
  b. a substantially incompressible flowable surrogate medium bounded by an ENTRY SURFACE via which converging EM waves enter the surrogate medium, the flowable medium being retained within a container having a deformable and/or elastic surface(s), wherein,
  wherein for a selected one or more of sub-10 GHz radiation frequency(ies) of the sub-10 GHz EM radiation:
    i. an average refractive index $n^{AVERAGE}_{SURROGATE\_MEDIUM}$ of the surrogate medium equals at least a minimum refractive-index threshold value that is at least 2;

ii. the ENTRY_SURFACE includes a power-significant portion via which an entry-surface-power-significant-fraction ESPSF equal to at least 0.1 by power of the converging waves of EM radiation at the sub-10 GHz selected frequency(ies) enter the surrogate medium;

iii. before entering the surrogate medium via the ENTRY_SURFACE, the EM radiation at the selected frequency(ies) has focused at an initial focus location IFL; and iii. for all locations on the power-significant portion of the ENTRY_SURFACE, a local normal line passes within an IFL-tolerance-distance from the initial focus location IFL, the IFL-tolerance-distance being at most 1 cm.

It is now disclosed a system for irradiating biological tissue comprising:

a. an ellipsoidal reflector having foci F1 and F2 separated from each other by at least an F1-F2 separation distance of at least 5 cm;

b. a source of EM radiation configured to emit diverging EM waves of sub-10 MHz EM radiation, at least some of which are reflected by the ellipsoidal reflector to form converging EM waves having one or more sub-10 MHz radiation frequency(ies); and c. a surrogate medium having an ENTRY_SURFACE via which converging EM waves enter the surrogate medium, wherein for a selected one or more of sub-10 MHz radiation frequency(ies) of the sub-10 MHz EM radiation, i. an average refractive index $n^{AVERAGE}_{SURROGATE\_MEDIUM}$ of the surrogate medium equals at least a minimum refractive-index threshold value that is at least 2;

ii. the ENTRY_SURFACE includes a power-significant portion via which an entry-surface-power-significant-fraction ESPSF equal to at least 0.1 by power of the converging waves of EM radiation at the sub-10 MHz selected frequency(ies) enter the surrogate medium; and iii. for all locations on the power-significant portion of the ENTRY_SURFACE:
  A. a local normal line passes within an F2-tolerance-distance from F2, the F2-tolerance-distance being at most 1 cm and/or
  B. a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:

a. a converging EM wave source of converging waves of EM radiation at sub-10 MHz frequency(ies); and b. a surrogate medium having an ENTRY SURFACE through which the converging waves enter into the surrogate medium, wherein for a selected one or more of sub-10 MHz radiation frequency(ies) of the sub-10 MHz EM radiation i. an average refractive index $n^{AVERAGE}_{SURROGATE\_MEDIUM}$ of the surrogate medium equals at least a minimum refractive-index threshold value that is at least 2;

ii. the ENTRY_SURFACE includes a power-significant portion via which an entry-surface-power-significant-fraction ESPSF equal to at least 0.1 by power of the converging waves of EM radiation at the sub-10 MHz selected frequency(ies) enter the surrogate medium; and iii. for every location on the power-significant portion of the ENTRY_SURFACE, a local Poynting vector of converging EM waves at the selected frequency(ies) is substantially normal to the ENTRY_SURFACE at the location within an angular deviation tolerance that is at most 10 degrees.

It is now disclosed a system for irradiating biological tissue comprising:

a. a converging EM wave source of converging waves of EM radiation at sub-10 MHz frequency(ies); and b. a surrogate medium having an ENTRY SURFACE through which the converging waves enter into the surrogate medium, wherein, wherein for a selected one or more of sub-10 MHz radiation frequency(ies) of the sub-10 MHz EM radiation:

i. an average refractive index $n^{AVERAGE}_{SURROGATE\_MEDIUM}$ of the surrogate medium equals at least a minimum refractive-index threshold value that is at least 2;

ii. the ENTRY_SURFACE includes a power-significant portion via which an entry-surface-power-significant-fraction ESPSF equal to at least 0.1 by power of the converging waves of EM radiation at the sub-10 MHz selected frequency(ies) enter the surrogate medium;

iii. before entering the surrogate medium via the ENTRY_SURFACE, the EM radiation at the selected frequency(ies) has focused at an initial focus location IFL; and iii. for all locations on the power-significant portion of the ENTRY_SURFACE, a local normal line passes within an IFL-tolerance-distance from the initial focus location IFL, the IFL-tolerance-distance being at most 1 cm.

It is now disclosed a system for irradiating biological tissue comprising:

a. an ellipsoidal reflector having foci F1 and F2 separated from each other by at least an F1-F2 separation distance of at least 5 cm;

b. a source of EM radiation configured to emit diverging EM waves of sub-10 GHz EM radiation, at least some of which are reflected by the ellipsoidal reflector to form converging EM waves having one or more sub-10 GHz radiation frequency(ies);

c. a lid whose outer surface mechanically coupled to and/or attached to the ellipsoidal reflector to form a substantially water-tight seal between an interior region bounded by the ellipsoidal reflector and the bounding surface and an exterior region, wherein the lid is shaped so that for a selected one or more of sub-10 GHz radiation frequency(ies) of the sub-10 GHz EM radiation, an outer surface of the lid includes a power-significant portion via which an entry-surface-power-significant-fraction ESPSF equal to at least 0.1 by power of the converging waves of EM radiation at the sub-10 GHz selected frequency(ies) pass, and for all locations on the power-significant portion of the lid:
  A. a local normal line passes within an F2-tolerance-distance from F2, the F2-tolerance-distance being at most 1 cm and/or
  B. a local Poynting vector of converging EM waves at the selected frequency(ies) is substantially normal to the ENTRY_SURFACE at the location within an angular deviation tolerance that is at most 10 degrees.

In some embodiments, the power-significant portion of the outer surface of the lid is immersed within a surrogate medium so that the outer surface of the lid defines an ENTRY_SURFACE through which converging EM waves enter the surrogate medium.

In some embodiments, the power-significant portion of the outer surface of the lid is immersed within a surrogate medium so that the outer surface of the lid defines an ENTRY_SURFACE through which converging EM waves enter the surrogate medium and a refractive index $n_{SURROGATE\_MEDIUM}$ of the surrogate medium equals at least a minimum refractive-index threshold value that is at least 2;

In some embodiments, the power-significant portion of the outer surface of the lid is immersed within a surrogate medium so that the outer surface of the lid defines an ENTRY_SURFACE through which converging EM waves enter the surrogate medium and a power-average refractive index $n^{AVERAGE}_{SURROGATE\_MEDIUM}$ of the surrogate medium equals average by a power-weighted optical paths of the converging EM waves is at least a minimum refractive-index threshold value that is at least 2.

In some embodiments, the surrogate medium is within a backward style sink.

In some embodiments, the surrogate medium is within a backward style sink including a neck slot.

It is now disclosed a method of irradiating biological tissue comprising:
  a. immersing a portion of biological tissue in a surrogate medium substance having an average refractive indexes $n^{AVERAGE}_{SURROGATE\_MEDIUM}$ equal to at least 2;
  b. within the surrogate medium substance, generating converging EM waves of EM radiation at sub-10 GHz frequency(ies) which travel through the surrogate medium substance and enter the biological tissue via the immersed portion so as to irradiate the biological tissue.

In some embodiments, at least 90% of an optical path between a location that the converging EM waves are generated and a surface of location of the immerse portion is within the surrogate medium.

In some embodiments, the converging EM waves are generated at a surface of an ellipsoidal reflector within the surrogate medium substance.

In some embodiments, the converging EM waves are generated by reflecting diverging EM waves within the surrogate medium substance, the diverging EM waves being generated by EM radiation source(s) immersed within the surrogate medium substance.

It is now disclosed a non-invasive method of heating tissue of a live human subject using electromagnetic (EM) energy, the method comprising:
  a. for a target location range that comprises a spherical region having a radius of less than 5 cm, each location within the target location range being buried beneath all external and internal skin surfaces of the human subject by at least 1 cm, selecting any target location within the target range; and
  b. without any solid objet penetrating the skin of the human subject towards the target location, heating the any selected target location by using externally-delivered EM energy radiating from outside the body of the human subject so as to heat the any selected target location to a temperature that exceeds 42 degrees Celsius while all locations within the human subject that are displaced from the selected target location by more than 2 cm are maintained at a temperature that is less than 42 degrees C.

It is now disclosed a non-invasive method of heating a target tissue of a live human subject using electromagnetic (EM) energy, the method comprising:
  Without any solid object penetrating skin of the human subject, heating a buried target location that is beneath all external and internal skin surfaces of the human subject by at least 1 cm using externally-delivered EM energy from outside the body of the human subject so as to heat the selected target location to a temperature that exceeds 42 degrees Celsius such that:
    i. all locations within the human subject that are displaced from the selected target location by more than 2 cm are maintained at a temperature that is less than 42 degrees; and
    ii. for every patch of skin surface of the human patient whose area is 75 cm^2 and boundary is a circle via which at least 10% of the tissue-heating EM energy passes, a center of a best spherical section approximation to the patch of skin surface is displaced from the actual convergence peak location by at least 1 cm.

It is now disclosed a method of treating neural tissue of a mammalian subject, the method comprising:
  transmitting low-frequency low-intensity CW electromagnetic (EM) energy having very low frequency(ies) below 10 Mhz into the mammalian subject's body so that a peak intensity of the transmitted low frequency EM energy occurs within neuronal tissue at a depth of at least 2 cm beneath the skin surface above the neural tissue so as to stimulate and/or depolarize neurons in the vicinity of a location of the peak intensity wherein:
    i) the non-invasive method is carried out without mechanically penetrating beneath the skull; and
    ii) a peak intensity of the low-intensity CW within the patient's body is below a threshold needed to induce necrosis or apoptosis in neural cells of the neural tissue.

It is now disclosed a method of heating tissue of a live human subject using electromagnetic (EM) energy, the method comprising:
  without penetrating skin of the human subject, stimulating neurons at a buried target location that is beneath all external and internal skin surfaces of the human subject by at least 1 cm using externally-delivered EM energy from outside the body of the human subject such that:
    i. no locations within the human subject that are displaced from the selected target location by less than 5 cm and more than 2 cm are subjected to neuron-stimulating EM radiation; and
    ii. for every circular patch of skin of the human patient whose area is 75 cm^2 via which at least 10% of the tissue-heating EM energy passes, a center of a best spherical section approximation of the circular patch of skin is displaced from the actual convergence peak location by at least 1 cm.

It is now disclosed a method of neuron irradiation comprising:
  generating EM radiation having a frequency-dependent power profile determined in accordance with one or more resonance frequencies of mammalian neural cell(s) and/or neural tissue to elevate a neural cell potential; and
  causing the EM radiation generated outside of the mammalian subject to propagate outside of a mammalian subject and to subsequently penetrate the skin of the mammalian subject so as to irradiate neuron(s) of the live, mammalian subject.

It is now disclosed a method of neuron irradiation comprising:

generating EM radiation having a frequency-dependent power profile determined in accordance with one or more resonance frequencies of mammalian neural cell(s) and/or neural tissue; and causing the EM radiation generated outside of the mammalian subject to propagate outside of a mammalian subject and to subsequently penetrate the skin of the mammalian subject so as to irradiate neuron(s) of the live, mammalian subject.

In some embodiments:

i. the frequency-dependent power profile is such that for a given resonance frequency band having a peak value PV and a peak width PW, a radiation power of at least one resonance frequency exceeds by at least a factor p a radiation intensity at any off-peak frequency that deviates from the peak width by at least twice the peak width and at most three times the peak width; and ii. a value of p is at least 2.

In some embodiments, the value of p is at least 5 or at least 10 or at least 50.

In some embodiments, the EM radiation include converging EM waves of radiation.

In some embodiments, the EM converging waves are generated using an ellipsoidal reflector.

In some embodiments, the radiation is administered to produce a peak location at a depth exceeding 1 cm beneath the skin.

In some embodiments, the radiation is administered to produce a peak location at a depth exceeding 2 cm beneath the skin.

In some embodiments, the radiation is administered to produce a peak location at a depth exceeding 3 cm beneath the skin.

In some embodiments, the radiation is administered to produce a peak location at a depth exceeding 5 cm beneath the skin.

In some embodiments, the radiation is administered to produce a peak location at a depth d beneath a skin surface and a peak width PW around the peak location such that a ratio between the peak width PW and the depth d is at most 0.5.

In some embodiments, the ratio is at most 0.3 or at most 0.1.

In some embodiments, the irradiation of the neurons is sufficient to cause at least a 10% change in some neural cell membrane potential.

In some embodiments, the irradiation of the neurons is sufficient to cause depolarization and/or stimulate the neuron(s).

In some embodiments, EM radiation is applied to irradiate the neuron(s) for at least 30 seconds.

In some embodiments, EM radiation is applied to irradiate the neuron(s) for at least 5 minutes or at least 20 minutes or at least 60 minutes In some embodiments, the EM radiation is applied to a subject's brain.

In some embodiments, the EM radiation is used to stimulate brain pleasure centers.

In some embodiments, the EM radiation is used to improve subject memory.

In some embodiments, the method is used to treat at least one condition selected from the group consisting of: clinical depression, non-clinical depression, dysthymia, bipolar disorder, drug addiction, substance abuse, anxiety disorder, obsessive compulsive disorder, or Parkinson's disease.

In some embodiments, the neural resonance frequency is less than 1 KHz.

In some embodiments, the resonance frequency is selected from the frequency bands of: 1-4 Hz, 4-8 Hz, 8-13 Hz, 13-30 Hz, 30-100 Hz, 100-250 Hz, and excluding 50 Hz and 60 Hz.

In some embodiments, the resonance frequency selected from the frequency bands of 1-4 Hz, and the neuron is in the frontal cortex.

In some embodiments, the resonance frequency selected from the frequency bands of 8-13 Hz, and the neuron is in posterior regions of head or in the sensorimotor cortex.

In some embodiments, the resonance frequency selected from the frequency bands of 30-100 Hz, and the neuron is in the somatosensory cortex.

An apparatus comprising:

a source of converging EM waves having a frequency-dependent power profile determined in accordance with one or more resonant frequencies of mammalian neural cell(s) and/or neural tissue.

In some embodiments, comprising a surrogate medium.

In some embodiments, the source of converging EM waves includes an ellipsoidal reflector.

It is now disclosed a system for irradiating biological tissue system comprising:

a. an ellipsoidal reflector that is shaped as an ellipsoidal section to define an inner region, the ellipsoidal reflector having a proximal focus F1 and a distal focus F2 that are separated from each other by at least 5 cm;

b. a source of EM radiation configured to emit diverging EM waves of sub-10 GHz EM radiation, at least some of which are reflected by the ellipsoidal reflector to form converging EM waves having one or more sub-10 GHz radiation frequency(ies); and c. a surrogate medium which fills substantially an entirety of a proximal portion of the ellipsoidal reflector that is more proximal than focus F1, the surrogate medium having a EXIT SURFACE, wherein for one or more of the sub-10 GHz radiation frequency(ies):

i. at least 30% or at least 50% of power of the converging EM waves pass at the selected one or more frequency(ies) pass through the EXIT_SURFACE; and ii. an average refractive index $n^{AVERAGE}_{SURROGATE\_MEDIUM}$ of the surrogate medium equals at least a minimum refractive-index threshold value that is at least 2.

It is now disclosed a system for irradiating biological tissue system comprising:

a. an ellipsoidal reflector that is shaped as an ellipsoidal section to define an inner region, the ellipsoidal reflector having a proximal focus F1 and a distal focus F2 that are separated from each other by at least 5 cm;

b. a source of EM radiation configured to emit diverging EM waves of sub-10 GHz EM radiation, at least some of which are reflected by the ellipsoidal reflector to form converging EM waves having one or more sub-10 GHz radiation frequency(ies); and c. a surrogate medium which fills substantially an entirety of a proximal portion of the ellipsoidal reflector that is more proximal than focus F1, the surrogate medium having a EXIT_SURFACE located distal to F1 and proximal to F2, wherein for one or more of the sub-10 GHz radiation frequency(ies):

i. at least 30% or at least 50% of power of the converging EM waves pass at the selected one or more frequency(ies) pass through the EXIT_SURFACE; and ii. an average refractive index $n^{AVERAGE}_{SURROGATE\_MEDIUM}$ of the surrogate medium equals at least a minimum refractive-index threshold value that is at least 2.

It is now disclosed a system for irradiating biological tissue system comprising:
a. an ellipsoidal reflector that is shaped as an ellipsoidal section to define an inner region, the ellipsoidal reflector having a proximal focus F1 and a distal focus F2;
b. a source of EM radiation configured to emit diverging EM waves of sub-10 GHz EM radiation, at least some of which are reflected by the ellipsoidal reflector to form converging EM waves having one or more sub-10 GHz radiation frequency(ies);
c. a surrogate medium which fills substantially an entirety of a proximal portion of the ellipsoidal reflector that is more proximal than focus F1, the surrogate medium having a convex EXIT_SURFACE that bulges towards F2 via which at least 30% or at least 50% of the power of the converging EM waves pass, the EXIT SURFACE being located distal to F1 and proximal to F2, wherein for at least one given frequency(ies) of the radiation frequency(ies) that is less than an upper bound frequency, an average refractive index $n^{AVERAGE}_{SURROGATE\_MEDIUM}$ of the surrogate medium equals at least a minimum refractive-index threshold value that is at least 2.

It is now disclosed a system for irradiating biological tissue system comprising:
a. an ellipsoidal reflector that is shaped as an ellipsoidal section to define an inner region, the ellipsoidal reflector having a proximal focus F1 and a distal focus F2;
b. a source of EM radiation configured to emit diverging EM waves of sub-10 GHz EM radiation, at least some of which are reflected by the ellipsoidal reflector to form converging EM waves having one or more sub-10 GHz radiation frequency(ies); and
c. a surrogate medium which fills substantially an entirety of a proximal portion of the ellipsoidal reflector that is more proximal than focus F1, the surrogate medium having a flat EXIT SURFACE located distal to F1 and proximal to F2 via which at least 30% or at least 50% of power of the converging EM waves pass, an average location of the EXIT SURFACE being at least 1 cm proximal of F2,
wherein for at least one given frequency(ies) of the radiation frequency(ies) that is less than an upper bound frequency, an average refractive index $n^{AVERAGE}_{SURROGATE\_MEDIUM}$ of the surrogate medium equals at least a minimum refractive-index threshold value that is at least 2.

It is now disclosed a system comprising:
a. a shell assembly comprising a ellipsoidal reflector that is shaped as an ellipsoidal section and having a proximal focus F1 and a distal focus F2, the shell assembly defining an inner region including focus F1;
b. a source of EM radiation configured to emit diverging EM waves of sub-10 GHz EM radiation, at least some of which are reflected by the ellipsoidal reflector to form converging EM waves having one or more sub-10 GHz radiation frequency(ies); and
c. a surrogate medium which fills substantially an entirety of a proximal portion of the ellipsoidal reflector that is more proximal than focus F1, the surrogate medium having a flat EXIT SURFACE located distal to F1 and proximal to F2 via which at least 30% or at least 50% of power of the converging EM waves pass, an average location of the EXIT SURFACE being more distal than a distal end of the shell assembly, wherein for at least one given frequency(ies) of the radiation frequency(ies) that is less than an upper bound frequency, an average refractive index $n^{AVERAGE}_{SURROGATE\_MEDIUM}$ of the surrogate medium equals at least a minimum refractive-index threshold value that is at least 2.

In some embodiments, the distal end of the shell assembly is part of the ellipsoidal reflector.

In some embodiments, the distal end of the shell assembly is part of an extension section that is:
i. not shaped like an ellipsoidal section;
ii. attached to a distal end of the ellipsoidal reflector; and
iii. generally oriented in a proximal-distal direction substantially parallel to a line segment between F1 and F2.

In some embodiments, the EXIT_SURFACE has a longitudinal position more distal than F2.

In some embodiments, i. at least a portion of the surrogate medium is a substantially incompressible flowable substance retained within a container having a deformable bounding surface(s); and
ii. a shape and/or orientation and/or position of the EXIT SURFACE and a position of the movable location along the F1-F2 line segment of the surrogate medium is determined at least in part by a configuration of the deformable container surface(s).

In some embodiments, the EXIT SURFACE includes a movable location on the F1-F2 line segment between foci F1 and F2 that is movable relative to the ellipsoidal reflector over a range of at least 2 mm (or at least 5 mm or at least 1 cm or at least 2 cm or at least 5 cm) along the F1-F2 line segment.

In some embodiments, the EXIT_SURFACE is deformable and wherein motion of the movable location deforms the EXIT_SURFACE.

The system or method of any preceding claim the range is at least 2 cm.

In some embodiments, is ENTRY_SURFACE contiguous.

In some embodiments, is ENTRY_SURFACE discontiguous.

In some embodiments,
i. it is possible to divide ENTRY_SURFACE into infinitesimal patches;
ii. at least some patches are F2-oriented relative to focus F2 so that local normal line passes within a F2-tolerance distance of F2;
iii. outward projections of all F2-oriented patches onto a reference sphere centered at F2 and having a radius equal to the F1-F2 separation distance occupy at least 10% of the reference sphere and/or a majority of all locations on the reference sphere within 30 degrees of F1.

In some embodiments, the surrogate medium has an ENTRY SURFACE through which the converging waves enter into the surrogate medium, and the EXIT SURFACE includes a movable location on the F1-F2 line segment between foci F1 and F2 that is movable relative to the power-significant portion of the ENTRY SURFACE over a range of at least 0.5 cm (or at least 1 cm or at least 2 cm) along the F1-F2 line segment.

In some embodiments, i. at least a portion of the surrogate medium is a substantially incompressible flowable substance retained within a container having a deformable bounding surface(s); and ii. a shape and/or orientation and/or position of the EXIT SURFACE and a position of the movable location along the F1-F2 line segment of the surrogate medium is determined at least in part by a configuration of the deformable container surface(s).

In some embodiments, flow of the flowable surrogate medium substance within the container:
  i. deforms the EXIT SURFACE so as to cause motion of the movable location along the F1-F2 line segment; and
  ii. deforms the deformable and/or elastic bounding surface(s) of the container.

In some embodiments, deformation of the deformable container surface(s) induces flow of the flowable surrogate medium substance within the container so as to deform the EXIT SURFACE, thereby causing motion of the movable location along the F1-F2 line segment.

In some embodiments, at least a portion of the deformable surface(s) of the container is also elastic.

In some embodiments, at least a portion of the surrogate medium is a substantially incompressible flowable substance retained within a container having an elastic bounding surface(s).

In some embodiments, a shape of the ENTRY SURFACE is maintained constant by a rigid surface of the container.

In some embodiments, the surrogate medium includes a deformable portion which when deformed enables modification of the position of the movable location to provide the range.

In some embodiments, a. the EXIT SURFACE is deformable; and b. deformation of the EXIT SURFACE causes motion of the movable location.

In some embodiments, i. the substantially incompressible flowable surrogate medium has an EXIT SURFACE via which converging EM waves exit the surrogate medium; ii. an exit surface power fraction EXS_PF equal to at least 0.3 of the ellipsoidal-reflector-formed converging EM waves at the selected frequency(ies) exit the surrogate medium via a power-significant portion of the EXIT_SURFACE; iii. a shape of the power-significant portion of the EXIT_SURFACE is determined by the deformable and/or elastic container surface(s).

In some embodiments, the surrogate medium is or includes any combination of a liquid, solid, a gel, a liquid biological fluids, a colloid solution, plant tissue, animal tissue, granular matter, and natural or artificial material having a cellular-structure.

In some embodiments, the liquid includes any combination of an aqueous solution, a saline solution, a non-polar solvent, and an oil or oily liquid.

In some embodiments, the biological fluid(s) includes any combination of blood, lymph fluid, spinal cord fluid, and brain fluid.

In some embodiments, the animal tissue includes any combination of fat, bone marrow, and muscle.

In some embodiments, the average refractive index $n^{AVERAGE}_{SURROGATE\_MEDIUM}$ of the surrogate medium is the average computed along a line extension of the F1-F2 line segment between foci F1 and F2.

In some embodiments, the average refractive index $n^{AVERAGE}_{SURROGATE\_MEDIUM}$ of the surrogate medium is power-averaged, optical-path-averaged according to the converging EM waves that pass through the surrogate medium wherein the power-averaging is at the selected frequency(ies).

In some embodiments, a power-averaged location on the power-significant portion of the ENTRY_SURFACE is distanced from F2 by at least 10% of the distance between F1 and F2.

In some embodiments, a power-averaged location on the ENTRY_SURFACE is distanced from F2 by at least 10% of the distance between F1 and F2.

In some embodiments, a power-averaged location on the power-significant portion ENTRY_SURFACE is distanced from F2 by at least 20% of the distance between F1 and F2.

In some embodiments, the surrogate medium has an EXIT_SURFACE through which the converging waves exit from the surrogate medium, and a power-averaged location on the EXIT_SURFACE is distanced from F2 by at least 10% of the distance between F1 and F2.

In some embodiments, the surrogate medium has an EXIT SURFACE through which the converging waves exit from the surrogate medium, and a power-averaged location on the EXIT_SURFACE is distanced from F2 by at least 20% of the distance between F1 and F2.

In some embodiments, the surrogate medium has a substantially uniform refractive index at the given frequency(ies) such that, for a weighted majority of location(s) within the surrogate medium that is weighted by an intensity of power of the diverging EM waves traveling within the surrogate medium, the location-dependent refractive index of the surrogate medium $n^{LOCATION-DEPENDENT}_{SURROGATE\_MEDIUM}$ equals the average refractive indexes $n^{AVERAGE}_{SURROGATE\_MEDIUM}$ within a index-match tolerance value equal to at most 30% at the at least one given frequency(ies).

In some embodiments, the index-match tolerance value is at most 20% or at most 10% or at most 5% or at most 2.5% or at most 1% or at most 0.5% or at most 0.1%.

In some embodiments, at least, by power, of the converging EM waves formed by the ellipsoidal reflector has frequency(ies) at the selected frequency(ies).

In some embodiments, at least a majority, by area, of the power-significant portion of the ENTRY SURFACE is part of a single rigid body.

In some embodiments, at least the position of the power-significant portion of ENTRY_SURFACE is mechanically constrained relative to the ellipsoidal reflector.

In some embodiments, at least the orientation of the power-significant portion of ENTRY_SURFACE is mechanically constrained relative to the ellipsoidal reflector.

In some embodiments, at least the configuration of the power-significant portion of ENTRY_SURFACE is mechanically constrained relative to the ellipsoidal reflector.

In some embodiments, the power-significant portion of the ENTRY SURFACE includes a plurality of discontiguous sub-portions {subportion$_1$, subportion$_2$, . . . subportion$_N$}, a respective sub-section power fraction subsection_power_fraction$_i$ of the converging EM waves at the selected frequency(ies) entering via each sub-portion of the plurality, a sum of the sub-section power fractions being equal to at least the entry surface power fraction ENS_F.

In some embodiments, the entry surface power fraction ENS_F is at least 0.5.

In some embodiments, the entry surface power fraction ENS_F is at least 0.6 or at least 0.7 or at least 0.8 or at least 0.9.

In some embodiments, substantially an entirety, by area, of the power-significant portion of the ENTRY SURFACE is part of a single rigid body.

In some embodiments, the positioning and/or orienting and/or configuring includes positioning and/or orienting and/or configuring the biological tissue relative to a stationary ellipsoidal reflector.

In some embodiments, the positioning and/or orienting and/or configuring includes positioning and/or orienting and/or configuring the ellipsoidal reflector relative to a stationary biological tissue.

In some embodiments, the positioning and/or orienting and/or configuring includes positioning and/or orienting both the ellipsoidal reflector and the biological tissue.

In some embodiments, the $n^{AVERAGE}_{SURROGATE\_MEDIUM}$ of the surrogate medium is equal to at least 3 or at least 4 or at least 5 or at least 6 or at least 8 or at least 10.

In some embodiments, the F1-F2 separation distance is at least 7.5 cm.

In some embodiments, the F1-F2 separation distance is at least 10 cm or at least 12.5 cm or at least 15 cm or at least 20 cm and/or at most 1 meter or at most 50 cm or at most 25 cm or at most 20 cm or at most 15 cm.

In some embodiments, the sub-10 GHz EM radiation comprises sub-3 GHz EM radiation, and wherein the selected frequency(ies) are sub-3 GHz radiation frequency(ies).

In some embodiments, the sub-10 GHz EM radiation comprises sub-2 GHz EM radiation, and wherein the selected frequency(ies) are sub-2 GHz radiation frequency(ies).

In some embodiments, the sub-10 GHz EM radiation comprises sub-1 GHz EM radiation, and wherein the selected frequency(ies) are sub-1 GHz radiation frequency(ies).

In some embodiments, the sub-10 GHz EM radiation comprises sub-0.5 GHz EM radiation, and wherein the selected frequency(ies) are sub-0.5 GHz radiation frequency(ies).

In some embodiments, the sub-10 GHz EM radiation comprises sub-100 MHz EM radiation, and wherein the selected frequency(ies) are sub-100 MHz radiation frequency(ies).

In some embodiments, the sub-10 GHz EM radiation comprises sub-10 MHz EM radiation, and wherein the selected frequency(ies) are sub-10 MHz radiation frequency(ies).

In some embodiments, the sub-10 GHz EM radiation comprises sub-5 MHz EM radiation, and wherein the selected frequency(ies) are sub-5 MHz radiation frequency(ies).

In some embodiments, the sub-10 GHz EM radiation comprises sub-2 MHz EM radiation, and wherein the selected frequency(ies) are sub-5 MHz radiation frequency(ies).

In some embodiments, the sub-10 GHz EM radiation comprises sub-1 MHz EM radiation, and wherein the selected frequency(ies) are sub-1 MHz radiation frequency(ies).

In some embodiments, the sub-10 GHz EM radiation comprises sub-0.5 MHz EM radiation, and wherein the selected frequency(ies) are sub-0.5 MHz radiation frequency(ies).

In some embodiments, the sub-10 GHz EM radiation comprises sub-0.1 MHz EM radiation, and wherein the selected frequency(ies) are sub-0.1 MHz radiation frequency(ies).

In some embodiments, the minimum refractive-index threshold value is at least threshold value is at least 3 or at least 4 or at least 5 or at least 6 or at least 8 or at least 10 or at least 20.

In some embodiments, the entry-surface-power-significant-fraction ESPSF is equal to at least 0.2 or at least 0.3 or at least 0.5 or at least 0.75 or at least 0.9.

In some embodiments, the exit surface power-significant-fraction EXS_PF is equal to at least 0.2 or at least 0.3 or at least 0.5 or at least 0.75 or at least 0.9.

In some embodiments, the angular deviation tolerance is at most 5 degrees or at most 2.5 degrees or at most 1 degree.

In some embodiments, the IFL-tolerance-distance and/or the OP tolerance distance and/or the F2 tolerance distance is at most 0.75 cm or at most 0.5 cm or at most 2.5 mm or at most 2 mm.

In some embodiments, the IFL-tolerance-distance and/or the OP tolerance distance and/or the F2 tolerance distance is at most 1 mm.

In some embodiments, the medium-tissue tolerance that is at most 30%. In some embodiments, the medium-tissue tolerance that is at most 20% or at most 10% or at most 5% or at most 2.5% or at most 1%.

In some embodiments, a longest dimension of the EM radiation source is less than the wavelength of the EM radiation at maximum power.

In some embodiments, a longest dimension of the EM radiation source is less than one half of the wavelength of the EM radiation at maximum power.

In some embodiments, a longest dimension of the EM radiation source is less one quarter of the wavelength of the EM radiation at maximum power.

188. In some embodiments, a longest dimension of the EM radiation source is less than 3 cm or least than 2 cm or less than 1 cm.

In some embodiments, the EM radiation source includes an EM-radiation-emitting location located at most 3 cm (or at most 2 cm or at most 1 cm) from the focus F1.

In some embodiments, a centroid of the EM radiation source is displaced from the focus F1 by at most 3 cm (or at most 2 cm or at most 1 cm).

In some embodiments, the EM radiation source is attached to and/or mechanically coupled to the ellipsoidal reflector.

In some embodiments, the target depth is determined in accordance with an ultrasound image, an NMR image, a CAT scan, an x-ray or any other medical image.

In some embodiments, a longest dimension of the EM radiation source is at most 25% (or at most 20% or at most 15% or at most 10% or at most 5%) of the wavelength of the EM radiation at maximum power.

In some embodiments, the surrogate medium further fills the portion of the ellipsoidal reflector that is more proximal than a location (i) along the F1-F2 line segment that is (ii) 1 cm from focus F1.

In some embodiments, the surrogate medium further fills the portion of the ellipsoidal reflector that is more proximal than a location (i) along the F1-F2 line segment that is (ii) twice as close to F1 as to F2.

In some embodiments, the surrogate medium further fills the portion of the ellipsoidal reflector that is more proximal than a location (i) along the F1-F2 line segment that is (ii) three times as close to F1 as to F2.

In some embodiments, the method is carried out so that and/or the system is configured so that power of the converging EM waves at the selected frequency(ies) is focused to produce within the biological tissue a peak width that is at most 2 cm.

In some embodiments, the method is carried out so that and/or the system is configured so that power of the converging EM waves at the selected frequency(ies) is focused to produce within the biological tissue a peak width that is at most 1 cm.

In some embodiments, the method is carried out so that and/or the system is configured so that power of the converging EM waves at the selected frequency(ies) is focused to produce within the biological tissue a peak width that is at most 5 mm.

In some embodiments, the method is carried out so that and/or the system is configured so that power of the converging EM waves at the selected frequency(ies) is focused to produce within the biological tissue a peak width that is at most 2.5 mm.

In some embodiments, the method is carried out so that and/or the system is configured so that power of the converging EM waves at the selected frequency(ies) is focused to produce within the biological tissue a peak width that is at most 1 mm.

In some embodiments, the method is carried out so that and/or the system is configured so that a peak location around which the peak width is centered is at least 1 cm or at least 2 cm or at least 3 cm beneath the surface of the biological tissue.

In some embodiments, the method is carried out so that and/or the system is configured so that power of the converging EM waves at the selected frequency(ies) is focused to produce within the biological tissue a peak width that is most 50% of a distance between a peak center and a surface of the biological tissue.

In some embodiments, the method is carried out so that and/or the system is configured so that power of the converging EM waves at the selected frequency(ies) is focused to produce within the biological tissue a peak width that is most 25% of a distance between a peak center and a surface of the biological tissue.

In some embodiments, the method is carried out so that and/or the system is configured so that power of the converging EM waves at the selected frequency(ies) is focused to produce within the biological tissue a peak width that is most 10% of a distance between a peak center and a surface of the biological tissue Use of the System or Method of Disclosed Herein to Irradiate Biological Tissue.

It is now disclosed for the first time a method for irradiating biological tissue comprising: a. transmitting diverging EM waves having radiation frequency(ies) that are less than 2.4 Gigahertz from a location that is substantially at F1 of an ellipsoidal reflector; b. reflecting at least a portion of the power of the diverging EM waves being reflected by the ellipsoidal reflector into converging EM waves, a distance between foci F1 and F2 of the ellipsoidal reflector being at least 5 cm; and c. receiving the converging EM waves into a surrogate media via a bounding surface including at least one substantially-sphere-section-shaped portion(s) whose associated sphere center is located substantially at focus F2 so that after traversing the surrogate medium, the converging EM waves enter into the biological tissue to irradiate the biological tissue at a time when focus F2 is located within the biological tissue, wherein for at least one of the radiation frequency(ies) that is less than 2.4 Gigahertz, a refractive index of the surrogate medium $n_{SURROGATE-MEDIUM}$ is at least one half of a refractive index of the biological tissue $n_{BIOLOGICAL-TISSUE}$ In some embodiments, the biological tissue is food and the method is effective to pyrolize the food.

In some embodiments, the biological tissue is live human tissue.

In some embodiments, the power level of radiation received into the biological tissue is insufficient to subject cells to necrosis or apoptosis.

In some embodiments, the method is carried out to treat any one of clinical depression, non-clinical depression, dysthymia, bipolar disorder, drug addiction, substance abuse, anxiety disorder, obsessive compulsive disorder, or Parkinson's disease.

In some embodiments, the method is carried out to kill cancer cells.

In some embodiments, foci F1 and F2 which are separated by at least 5 cm and at most 50 cm.

In some embodiments, the location from which the diverging EM waves are transmitted is source offset from F1 by an offset distance that is at most 1 cm.

In some embodiments, the offset distance is at most 5 mm.

In some embodiments, the offset distance is at most 5 mm.

In some embodiments, each of the at least one substantially-sphere-section-shaped portion(s) is respectively associated with a respective sphere center that is respectively located substantially at focus F2 within an F2 tolerance of at most 1 cm.

In some embodiments, the F2 tolerance is at most 5 mm or at most 2 mm.

In some embodiments, each of the at least one substantially-sphere-section-shaped portion(s) is respectively associated with a respective sphere center that is respectively located substantially at focus F2 within an F2 tolerance of at most 10% of a distance between F1 and F2.

In some embodiments, the F2 tolerance is at most 5% or at most 2% or at most 1% of a distance between F1 and F2.

In some embodiments, at a given frequency $\omega_{GIVEN}$ less than 2.4 Gigaheretz, a refractive index of the surrogate medium $n_{SURROGATE-MEDIUM}$ substantially matches a refractive index of human soft tissue $n_{HUMAN-SOFT-TISSUE}$ such that a surrogate-medium-human-soft-tissue-refractive-index-match ratio $$\frac{MAX(n_{surrogate-medium}, n_{human-soft-tissue})}{MIN(n_{surrogate-medium}, n_{human-soft-tissue})}$$

between: A. a greater of the refractive index of the surrogate medium $n_{SURROGATE-MEDIUM}$ and the refractive index of human soft tissue $n_{HUMAN-SOFT-TISSUE}$ defined as max $(n_{SURROGATE-MEDIUM}, n_{HUMAN-SOFT-TISSUE})$; and B. a lesser of the refractive index of the surrogate medium $n_{SURROGATE-MEDIUM}$ and the refractive index of human soft tissue $n_{HUMAN-SOFT-TISSUE}$ defined as min $(n_{SURROGATE-MEDIUM}, n_{HUMAN-SOFT-TISSUE})$, is at most a matching index max-ratio value MATCHING-MAX-RATIO that is at most 2.

In some embodiments, the matching index max-ratio value MATCHING-MAX-RATIO that is at most 1.5

In some embodiments, the matching index max-ratio value MATCHING-MAX-RATIO that is at most 1.3.

In some embodiments, the matching index max-ratio value MATCHING-MAX-RATIO that is at most 1.1.

In some embodiments, the system is configured to cause the EM radiation to propagate within a mismatching medium before entering into the surrogate medium such that at the given frequency $\omega_{GIVEN}$ a refractive index of the mismatching medium $n_{MISMATCHING-MEDIUM}$ differs significantly from the refractive index of the surrogate medium $n_{SURROGATE-MEDIUM}$ such that a surrogate-medium-human-soft-tissue-refractive-index-match ratio $$\frac{MAX(n_{surrogate-medium}, n_{mismatching-medium})}{MIN(n_{surrogate-medium}, n_{mismatching-medium})}$$

between:
A. a greater of the refractive index of the surrogate medium $n_{SURROGATE\text{-}MEDIUM}$ and the refractive index of the mismatching medium $n_{MISMATCHING\text{-}MEDIUM}$ defined as $\max(n_{SURROGATE\text{-}MEDIUM}, n_{MISMATCHING\text{-}MEDIUM})$; and
B. a lesser of the refractive index of the surrogate medium $n_{SURROGATE\text{-}MEDIUM}$ and the refractive index of the mismatching medium $n_{MISMATCHING\text{-}MEDIUM}$ defined as $\min(n_{SURROGATE\text{-}MEDIUM}, n_{MISMATCHING\text{-}MEDIUM})$, is at least a mismatching index min-ratio value MISMATCHING-MAX-RATIO that is at least 2.1 or at least 3 or at least 5.

In some embodiments, a ratio between:
i. MISMATCHING-MAX-RATIO; and
ii. MATCHING-MAX-RATIO,
is at least 2 or at least 3 or at least 5 or at least 6.

In some embodiments, the bounding surface includes exactly one substantially sphere-section-shaped portion associated with a sphere center location CENTER_LOC and a sphere radius $r_{SPHERE}$.

In some embodiments, a surface area of the sphere-shaped portion is equal to at least 10% of sphere surface area $4\pi(r_{SPHERE})^2$.

In some embodiments, the bounding surface includes a plurality of sphere section-shaped portions that all share a common sphere-center location CENTER_LOC.

In some embodiments, if each sphere section is radially projected onto a single sphere sphere centered at CENTER_LOC and having a radius of $4\pi(r_{SINGLE\text{-}SPHERE})^2$, the projected sphere section would cover at least 10% of the surface area $4\pi(r_{SINGLE\text{-}SPHERE})^2$ of the single sphere.

In some embodiments, a refractive index of the surrogate medium $n_{SURROGATE\text{-}MEDIUM}$ for at least one of the radiation frequency(ies) less than 2.4 Gigahertz is equal to at least 2.

In some embodiments, a refractive index of the surrogate medium $n_{SURROGATE\text{-}MEDIUM}$ for at least one of the radiation frequency(ies) less than 2.4 Gigahertz is equal to at least 2.

In some embodiments, a refractive index of the surrogate medium $n_{SURROGATE\text{-}MEDIUM}$ for at least one of the radiation frequency(ies) less than 2.4 Gigahertz is equal to at least 5.

In some embodiments, for at least one of the radiation frequency(ies) less than 2.4 Gigahertz, a ratio between a refractive index of the surrogate medium $n_{SURROGATE\text{-}MEDIUM}$ and a refractive index of a material and/or a substance bordering the surrogate medium via the bounding surface is a refractive index ration that is at least 1.1 or at least 1.5 or at least 2 or at least 4.

In some embodiments, the foci are separated by at least 10 cm.

In some embodiments, the radiation level is low enough to heat biological tissue to at most 70 degrees C.

It is now disclosed a method for irradiating biological tissue comprising: a. providing or generating converging waves of EM radiation having radiation frequency(ies) that are less than 2.4 Gigahertz; and b. causing the converging waves to enter into a surrogate medium via an actual bounding surface of the surrogate medium, to traverse the surrogate medium, and to enter into the biological tissue to irradiate where biological tissue, wherein for a given frequency $\omega_{GIVEN}$ of the radiation frequency(ies): (i) at the given frequency $\omega_{GIVEN}$, a refractive index of the surrogate medium $n_{SURROGATE\text{-}MEDIUM}$ substantially matches a refractive index of human soft tissue $n_{HUMAN\text{-}SOFT\text{-}TISSUE}$ such that a surrogate-medium-human-soft-tissue-refractive-index-match ratio $$\frac{\text{MAX}(n_{surrogate\text{-}medium}, n_{human\text{-}soft\text{-}tissue})}{\text{MIN}(n_{surrogate\text{-}medium}, n_{human\text{-}soft\text{-}tissue})}$$

between: A. a greater of the refractive index of the surrogate medium $n_{SURROGATE\text{-}MEDIUM}$ and the refractive index of human soft tissue $n_{HUMAN\text{-}SOFT\text{-}TISSUE}$ defined as $\max(n_{SURROGATE\text{-}MEDIUM}, n_{HUMAN\text{-}SOFT\text{-}TISSUE})$; and B. a lesser of the refractive index of the surrogate medium $n_{SURROGATE\text{-}MEDIUM}$ and the refractive index of human soft tissue $n_{HUMAN\text{-}SOFT\text{-}TISSUE}$ defined as $\min(n_{SURROGATE\text{-}MEDIUM}, n_{HUMAN\text{-}SOFT\text{-}TISSUE})$, is at most a matching index max-ratio value MATCHING-MAX-RATIO that is at most 2; (ii) immediately before entering into the surrogate medium via the bounding surface, the converging waves of EM radiation at the given frequency $\omega_{GIVEN}$ define a pre-crossing set of Poynting vectors that is associated with a first focus location $\text{FOCUS}_{FIRST}$; (iii) immediately after entering into the surrogate medium via the bounding surface, the converging waves of EM radiation at the given frequency $\omega_{GIVEN}$ define a post-crossing set of Poynting vectors that is associated with a second focus location $\text{FOCUS}_{SECOND}$; (iv) when the actual bounding surface ABS is subjected to a one millimeter length scale smoothing algorithm, this defines a mathematically smoothed bounding surface MBS; (v) the mathematically smoothed bounding surface MBS; includes one or more Poynting-vector-matching-portion(s) whose shape matches the pre-crossing set of Poynting vectors at the frequency $\omega_{GIVEN}$; (vi) at least a fraction F whose value is at least ½ of the power at frequency $\omega_{GIVEN}$ which enters into the surrogate medium and whose post-crossing Poynting vector points to a location within 10 cm of the second focus location $\text{FOCUS}_{SECOND}$ enters via one of the Poynting-vector-matching-portion(s) at an incidence angle that is substantially parallel to a local surface normal within an angular deviation tolerance whose value is at most 10 degrees.

It is now disclosed a system for irradiating biological tissue comprising:
a. an ellipsoidal reflector having two foci F1 and F2;
b. a source of EM radiation that is:
i. relatively small compared to dimensions of the ellipsoid;
ii. centered substantially at one of the foci F1; and
iii. configured to emit diverging EM waves having radiation frequency(ies) that are less than 2.4 Gigahertz, at least a portion of the power of the diverging EM waves being reflected by the ellipsoidal reflector into converging EM waves; and
c. a surrogate medium having a bounding surface through which the converging waves enter into the surrogate medium, the bounding surface including at least one substantially-sphere-section-shaped portion(s) whose associated sphere center is located substantially at focus F2, wherein for at least one of the radiation frequency(ies) that is less than 2.4 Gigahertz, a refractive index of the surrogate medium $n_{SURROGATE\text{-}MEDIUM}$ is at least one half of a refractive index of the biological tissue $n_{BIOLOGICAL\text{-}TISSUE}$ In some embodiments, at a given frequency $\omega_{GIVEN}$ less than 2.4 Gigaheretz, a refractive index of the surrogate medium $n_{SURROGATE\text{-}MEDIUM}$ substantially matches a refractive index of human soft tissue $n_{HUMAN\text{-}SOFT\text{-}TISSUE}$ such that a surrogate-medium-human-soft-tissue-refractive-index-match ratio $$\frac{MAX(n_{surrogate-medium}, n_{human-soft-tissue})}{MIN(n_{surrogate-medium}, n_{human-soft-tissue})}$$

between:
A. a greater of the refractive index of the surrogate medium $n_{SURROGATE\text{-}MEDIUM}$ and the refractive index of human soft tissue $n_{HUMAN\text{-}SOFT\text{-}TISSUE}$ defined as $max(n_{SURROGATE\text{-}MEDIUM}, n_{HUMAN\text{-}SOFT\text{-}TISSUE})$; and
B. a lesser of the refractive index of the surrogate medium $n_{SURROGATE\text{-}MEDIUM}$ and the refractive index of human soft tissue $n_{HUMAN\text{-}SOFT\text{-}TISSUE}$ defined as $min(n_{SURROGATE\text{-}MEDIUM}, n_{HUMAN\text{-}SOFT\text{-}TISSUE})$, is at most a matching index max-ratio value MATCHING-MAX-RATIO that is at most 2.

In some embodiments, the matching index max-ratio value MATCHING-MAX-RATIO that is at most 1.5 or at most 1.3 or at most 1.3.

In some embodiments, the system is configured to cause the EM radiation to propagate within a mismatching medium before entering into the surrogate medium such that at the given frequency $\omega_{GIVEN}$ a refractive index of the mismatching medium $n_{MISMATCHING\text{-}MEDIUM}$ differs significantly from the refractive index of the surrogate medium $n_{SURROGATE\text{-}MEDIUM}$ such that a surrogate-medium-human-soft-tissue-refractive-index-match ratio $$\frac{MAX(n_{surrogate-medium}, n_{mismatching-medium})}{MIN(n_{surrogate-medium}, n_{mismatching-medium})}$$

between:
A. a greater of the refractive index of the surrogate medium $n_{SURROGATE\text{-}MEDIUM}$ and the refractive index of the mismatching medium $n_{MISMATCHING\text{-}MEDIUM}$ defined as $max(n_{SURROGATE\text{-}MEDIUM}, n_{MISMATCHING\text{-}MEDIUM})$; and
B. a lesser of the refractive index of the surrogate medium $n_{SURROGATE\text{-}MEDIUM}$ and the refractive index of the mismatching medium $n_{MISMATCHING\text{-}MEDIUM}$ defined as $min(n_{SURROGATE\text{-}MEDIUM}, n_{MISMATCHING\text{-}MEDIUM})$,
is at least a mismatching index min-ratio value MISMATCHING-MAX-RATIO that is at least 2.1. or at least 3 or at least 5.

In some embodiments, a ratio between:
iii. MISMATCHING-MAX-RATIO; and
iv. MATCHING-MAX-RATIO,
is at least 2 or at least 3 or at least 5.

In some embodiments, the bounding surface includes exactly one substantially sphere-section-shaped portion associated with a sphere center location CENTER_LOC and a sphere radius $r_{SPHERE}$.

In some embodiments, a surface area of the sphere-shaped portion is equal to at least 10% of sphere surface area $4\pi(r_{SPHERE})^2$.

In some embodiments, the bounding surface includes a plurality of sphere section-shaped portions that all share a common sphere-center location CENTER_LOC.

In some embodiments, if each sphere section is radially projected onto a single sphere centered at CENTER_LOC and having a radius of $4\pi(r_{SINGLE\text{-}SPHERE})^2$, the projected sphere section would cover at least 10% of the surface area $4\pi(r_{SINGLE\text{-}SPHERE})^2$ of the single sphere.

In some embodiments, a refractive index of the surrogate medium $n_{SURROGATE\text{-}MEDIUM}$ for at least one of the radiation frequency(ies) less than 2.4 Gigahertz is equal to at least 2.

In some embodiments, a refractive index of the surrogate medium $n_{SURROGATE\text{-}MEDIUM}$ for at least one of the radiation frequency(ies) less than 2.4 Gigahertz is equal to at least 2.

In some embodiments, a refractive index of the surrogate medium $n_{SURROGATE\text{-}MEDIUM}$ for at least one of the radiation frequency(ies) less than 2.4 Gigahertz is equal to at least 5.

It is now disclosed a system for irradiating biological tissue comprising:
a. an ellipsoidal reflector having two foci F1 and F2;
b. a source of EM radiation that is:
  i. relatively small compared to dimensions of the ellipsoid;
  ii. centered substantially at one of the foci F1; and
  iii. configured to emit diverging EM waves having radiation frequency(ies) that are less than 2.4 Gigahertz, at least a portion of the power of the diverging EM waves being reflected by the ellipsoidal reflector into converging EM waves; and
c. a lid whose outer surface includes at least one substantially-sphere-section-shaped portion(s) whose associated sphere center is located substantially at focus F2, the lid located so that converging waves traverse the lid, the lid being directly or indirectly attached to the ellipsoidal reflector to form a substantially water-tight seal between an interior region bounded by the ellipsoidal reflector and the bounding surface and an exterior region.

In some embodiments, the outer surface of the lid includes exactly one substantially sphere-section-shaped portion associated with a sphere center location CENTER_LOC and a sphere radius $r_{SPHERE}$.

In some embodiments, a surface area of the sphere-shaped portion is equal to at least 10% of sphere surface area $4\pi(r_{SPHERE})^2$.

In some embodiments, the lid outer surface includes a plurality of sphere section-shaped portions that all share a common sphere-center location CENTER_LOC.

In some embodiments, if each sphere section is radially projected onto a single sphere centered at CENTER_LOC and having a radius of $4\pi(r_{SINGLE\text{-}SPHERE})^2$, the projected sphere section would cover at least 10% of the surface area $4\pi(r_{SINGLE\text{-}SPHERE})^2$ of the single sphere.

In some embodiments, a size of the EM energy source is at most 5 mm or at most 2 mm or at most 1 mm.

In some embodiments, a centroid of EM energy source offset from F1 by at most 5 mm or at most 2 mm or at most 1 mm.

In some embodiments, a size of the EM energy source is at most 0.1 times or at most 0.05 times a diameter of the ellipsoid defined by the ellipsoidal reflector at the plane of the focal point.

In some embodiments, a centroid of the EM energy source is offset from F1 by at most 0.1 or at most 0.05 times a diameter of the ellipsoid defined by the ellipsoidal reflector at the plane of the focal point.

In some embodiments, foci F1 and F2 which are separated by at most 50 cm or at most 100 cm.

In some embodiments, foci F1 and F2 which are separated by at least 10 cm.

In some embodiments, each of the at least one substantially-sphere-section-shaped portion(s) is respectively associated with a respective sphere center that is respectively located substantially at focus F2 within an F2 tolerance of at most 1 cm or at most 5 mm or at most 2 mm.

In some embodiments, each of the at least one substantially-sphere-section-shaped portion(s) is respectively associated with a respective sphere center that is respectively located substantially at focus F2 within an F2 tolerance of at most 10% or at most 5% or at most 2% of a distance between F1 and F2.

It is now disclosed a system for irradiating biological tissue comprising:
a. a source of converging waves of EM radiation having radiation frequency(ies) that are less than 2.4 Gigahertz; and
b. a surrogate medium having an actual bounding surface ABS through which the converging waves enter into the surrogate medium such that, for a given frequency $\omega_{GIVEN}$ of the radiation frequency(ies):
   (i) at the given frequency $\omega_{GIVEN}$, a refractive index of the surrogate medium $n_{SURROGATE\text{-}MEDIUM}$ substantially matches a refractive index of human soft tissue $n_{HUMAN\text{-}SOFT\text{-}TISSUE}$ such that a surrogate-medium-human-soft-tissue-refractive-index-match ratio $$\frac{\text{MAX}(n_{surrogate-medium}, n_{human-soft-tissue})}{\text{MIN}(n_{surrogate-medium}, n_{human-soft-tissue})}$$

between:
   A. a greater of the refractive index of the surrogate medium $n_{SURROGATE\text{-}MEDIUM}$ and the refractive index of human soft tissue $n_{HUMAN\text{-}SOFT\text{-}TISSUE}$ defined as $\max(n_{SURROGATE\text{-}MEDIUM}, n_{HUMAN\text{-}SOFT\text{-}TISSUE})$; and
   B. a lesser of the refractive index of the surrogate medium $n_{SURROGATE\text{-}MEDIUM}$ and the refractive index of human soft tissue $n_{HUMAN\text{-}SOFT\text{-}TISSUE}$ defined as $\min(n_{SURROGATE\text{-}MEDIUM}, n_{HUMAN\text{-}SOFT\text{-}TISSUE})$,
   is at most a matching index max-ratio value MATCHING-MAX-RATIO that is at most 2;
   (ii) immediately before entering into the surrogate medium via the bounding surface, the converging waves of EM radiation at the given frequency $\omega_{GIVEN}$ define a pre-crossing set of Poynting vectors that is associated with a first focus location $\text{FOCUS}_{FIRST}$;
   (iii) immediately after entering into the surrogate medium via the bounding surface, the converging waves of EM radiation at the given frequency $\omega_{GIVEN}$ define a post-crossing set of Poynting vectors that is associated with a second focus location $\text{FOCUS}_{SECOND}$;
   (iv) when the actual bounding surface ABS is subjected to a one millimeter length scale smoothing algorithm, this defines a mathematically smoothed bounding surface MBS;
   (v) the mathematically smoothed bounding surface MBS; includes one or more Poynting-vector-matching-portion(s) whose shape matches the pre-crossing set of Poynting vectors at the frequency $\omega_{GIVEN}$;
   (vi) at least a fraction F whose value is at least ½ of the power at frequency $\omega_{GIVEN}$ which enters into the surrogate medium and whose post-crossing Poynting vector points to a location within 10 cm of the second focus location $\text{FOCUS}_{SECOND}$ enters via one of the Poynting-vector-matching-portion(s) at an incidence angle that is substantially parallel to a local surface normal within an angular deviation tolerance whose value is at most 10 degrees.

In some embodiments, a displacement between $\text{FOCUS}_{FIRST}$ and $\text{FOCUS}_{SECOND}$ is at most 5 cm.

In some embodiments, a displacement between $\text{FOCUS}_{FIRST}$ and $\text{FOCUS}_{SECOND}$ is at most 2 cm.

In some embodiments, a displacement between $\text{FOCUS}_{FIRST}$ and $\text{FOCUS}_{SECOND}$ is at most 0.5 cm.

In some embodiments, a value of F is at least ¾ or at least 9/10.

In some embodiments, a value of the angular deviation tolerance is at most 5 degrees or at most 1 degree.

In some embodiments, the matching index max-ratio value MATCHING-MAX-RATIO that is at most 1.5 or at most 1.3 or at most 1.1.

In some embodiments, the system is configured to cause the EM radiation to propagate within a mismatching medium before entering into the surrogate medium such that at the given frequency $\omega_{GIVEN}$ a refractive index of the mismatching medium $n_{MISMATCHING\text{-}MEDIUM}$ differs significantly from the refractive index of the surrogate medium $n_{SURROGATE\text{-}MEDIUM}$ such that a surrogate-medium-human-soft-tissue-refractive-index-match ratio $$\frac{\text{MAX}(n_{surrogate-medium}, n_{mismatching-medium})}{\text{MIN}(n_{surrogate-medium}, n_{mismatching-medium})}$$

between:
   A. a greater of the refractive index of the surrogate medium $n_{SURROGATE\text{-}MEDIUM}$ and the refractive index of the mismatching medium $n_{MISMATCHING\text{-}MEDIUM}$ defined as $\max(n_{SURROGATE\text{-}MEDIUM}, n_{MISMATCHING\text{-}MEDIUM})$; and
   B. a lesser of the refractive index of the surrogate medium $n_{SURROGATE\text{-}MEDIUM}$ and the refractive index of the mismatching medium $n_{MISMATCHING\text{-}MEDIUM}$ defined as $\min(n_{SURROGATE\text{-}MEDIUM}, n_{MISMATCHING\text{-}MEDIUM})$,
   is at least a mismatching index min-ratio value MISMATCHING-MAX-RATIO that is at least 2.1 or at least 3 or at least 5.

In some embodiments, a ratio between:
   v. MISMATCHING-MAX-RATIO; and
   vi. MATCHING-MAX-RATIO,
   is at least 2. or at least 3 or at least 5.

In some embodiments, a wave front associated with the converging waves of EM energy at a location where the converging waves first encounters the bounding surface is shaped substantially as a spherical section.

In some embodiments, wherein:
   i. a best-fit ellipsoid of a wave front surface associated with the converging waves of EM energy at a location where the converging waves first encounters is defined as wave-front-best-fit-ellipsoid and is characterized by a pair of foci $F^{WAVE\text{-}FRONTG\text{-}BEST\text{-}FIT}_1$, $F^{WAVE\text{-}FRONTG\text{-}BEST\text{-}FIT}_2$; and
   ii. an inter-foci distance between the foci $F^{WAVE\text{-}FRONTG\text{-}BEST\text{-}FIT}_1$, $F^{WAVE\text{-}FRONTG\text{-}BEST\text{-}FIT}_2$ of the wave-front-best-fit-ellipsoid has a non-zero value defined as inter-foci-distance-wave-front-best-fit.

In some embodiments, the value inter-foci-distance-wave-front-best-fit exceeds 1 mm or exceeds 1 cm.

In some embodiments, each Poynting-vector-matching-portion(s) is shaped substantially as a spherical section.

In some embodiments, at least one Poynting-vector-matching-portion(s) is non-spherical such that for a given Poynting-vector-matching-portion selected from the at least one Poynting-vector-matching-portion(s), an inter-foci distance of a best fit ellipsoid of the given Poynting-vector-matching-portion is at least 1 mm or at least 1 cm.

In some embodiments, wherein a closest distance between:
i. a location where the converging EM waves are formed by the source of converging waves of EM radiation;
ii. the bounding surface, is at most 1 meter or at most 50 cm.

In some embodiments, the source of converging EM waves comprises:
i. a plurality of EM energy sources; and
ii. timing circuitry, the plurality of EM sources being configured to emit EM energy in response to the timing circuitry so that the superimposed EM radiation collectively emitted by the EM energy sources produces converging EM waves.

In some embodiments, the source of converging waves comprises:
i. an ellipsoidal reflector having two foci F1 and F2 which are separated by at least 5 cm; and
ii. a EM energy source that is relatively small compared to dimensions of the ellipsoid that is centered substantially at one of the foci F1, the EM energy source being configured to emit diverging EM waves which are at least partially reflected by the ellipsoidal reflector into converging EM waves.

It is now disclosed a method of irradiating biological tissue comprising:
a. generating converging EM waves having radiation frequency(ies) that are less than 2.4 Gigahertz; and
b. subjecting the biological tissue to the converging EM waves so that the converging EM waves enter the biological tissue, wherein:
i. for a given frequency $\omega_{GIVEN}$ of the radiation frequency(ies), every location LOC in space is said to have a respective location specific refractive index $n_{LOC}(LOC)$ respectively defined by the medium refractive index at the given frequency $\omega_{GIVEN}$ of the medium occupying location LOC in space;
ii. for the given frequency, a refractive index of the biological tissue is defined as $n_{BIOLOGICAL-TISSUE}$
iii. the location-specific refractive index $n_{LOC}$ (LOC) at the given frequency $\omega_{GIVEN}$ at locations along at least a fraction F of the optical path between:
A. a location where the EM converging waves are generated in step (a); and
B. a location where the EM converging waves enter into the biological tissue in step (b),
has a value equal to at least $$\frac{n_{biological-tissue}}{tolerance - multiple}$$

and at most tolerance-multiple*$n_{BIOLOGICAL-TISSUE}$;
iv. a value of fraction F is at least 0.9.
v. a value of tolerance multiple is at most 2.

It is now disclosed a method of irradiating biological tissue comprising:
a. immersing a portion of biological tissue in an index-matching substance; and
b. causing converging EM waves having radiation frequency(ies) that are less than 2.4 Gigahertz to enter into the biological tissue via an immersed biological tissue surface of the immersed portion of biological tissue.

In some embodiments, the EM waves are generated within index-matching substance.

In some embodiments, the EM waves are generated within index-matching substance by a source of converging EM waves that is at least partially immersed in the index-matching substance.

It is now disclosed a system comprising:
a. a source of converging waves of EM radiation having radiation frequency(ies) that are less than 2.4 Gigahertz;
b. a sink or bathtub or basin at least 10% of which is filled by surrogate medium(s);
the source of converging EM radiation source being configured to irradiate the surrogate medium.

It is now disclosed a system comprising
a. a source of converging waves of EM radiation having radiation frequency(ies) that are less than 2.4 Gigahertz; and b. a backward style sink (e.g. similar to what is common for hair washing in hair saloons where the patron leans his head back and his hair is washed) including a neck slot,
wherein the source of converging EM radiation source is configured to irradiate the space within the backward style sink.

In some embodiments, method of irradiating biological tissue, the method comprising:
causing EM energy of converging EM waves at one or more EM frequency(ies) less than 2 Gigahertz to:
a. cross through one or more non-gaseous surrogate medium(s) outside of the tissue of the live human subject; and
b. enter into the tissue of the biological tissue,
wherein, for a given frequency $\omega_{GIVEN}$ of the radiation frequency(ies),
i. in an initial state before crossing through the one or more non-gaseous surrogate medium(s) and entering into the biological tissue so that, in the initial state, the at least portion of the EM energy at the given frequency $\omega_{GIVEN}$ is initially focused to convergence peak $PEAK_{INITIAL-FOCUS}$ whose location is situated at least 2 cm beneath all surfaces of the biological tissue and whose peak width $PW_{INITIAL\_FOCUS}$ is at most 5 cm;
ii. the geometrical and/or optical properties of the one or more non-gaseous surrogate medium are such that an actual convergence peak $PEAK_{ACTUAL}$ of converging EM energy at the given frequency $\omega_{GIVEN}$ that actually enters into the biological tissue is also located at least 2 cm beneath all surfaces of the biological tissue and has a peak width $PW_{ACTUAL}$ whose magnitude is at most 5 times the initial focus peak width $PW_{INITIAL-FOCUS}$.

In some embodiments, a magnitude of a peak width $PW_{ACTUAL}$ of the actual convergence peak $PEAK_{ACTUAL}$ has a magnitude that is at most twice the initial focus peak width $PW_{INITIAL-FOCUS}$.

In some embodiments, a peak width $PW_{INITIAL\_FOCUS}$ is at most 2 cm or at most 1 cm.

In some embodiments, the initial focus of the converging EM waves and/or the geometrical and/or optical properties of the one or more non-gaseous surrogate medium are such that:
i. in a hypothetical absence of all of the one or more non-gaseous surrogate medium(s) so that all space via which converging EM waves propagate outside of the biological tissue is hypothetically a uniform medium having a refractive index of between 1 and 1.3 at the given frequency $\omega_{GIVEN}$, EM energy enters the biological tissue such that a hypothetical convergence peak $PEAK_{HYPOTHETICAL}$ of converging EM waves at the given frequency $\omega_{GIVEN}$ has a peak width $PW_{HYPOTHETICAL}$; and ii. an actual-hypothetical-peak-width-ratio between $PEAK_{ACTUAL}$ and is $PW_{HYPOTHETICAL}$ at most 0.5

In some embodiments, the actual-hypothetical-peak-width-ratio is at most 0.2.

In some embodiments, the biological tissue is tissue of a live human subject, and the convergence peaks are all located at least 1 cm beneath all skin surfaces of the live human subject.

In some embodiments, the convergence peaks are all located within a head of the live human subject.

In some embodiments, the actual convergence peak is located within a torso of the live human subject.

In some embodiments, the actual convergence peak is located within an arm or leg of the live human subject.

In some embodiments, for every patch of skin surface of the human patient whose area is 75 cm^2 and whose boundary is a circle via which at least 10% of the EM energy at the given frequency $\omega_{GIVEN}$ of the converging wave-front passes, a center of a best spherical surface section approximation to the surface patch of skin is displaced from the location of the actual convergence peak $PEAK_{ACTUAL}$ by at least 1 cm.

In some embodiments, for every patch of biological tissue surface of whose area is 75 cm^2 and whose boundary is a circle via which at least 10% of the EM energy at the given frequency $\omega_{GIVEN}$ of the converging wave-front passes, a center of a best spherical surface section approximation to the biological tissue surface patch is displaced from the location of the actual convergence peak $PEAK_{ACTUAL}$ by at least 1 cm.

In some embodiments, the method is carried out to raise a temperature of tissue at the location of the actual peak $PEAK_{ACTUAL}$ to at least 42 degrees C. and to at most 90 degrees C.

In some embodiments, the method is carried out without raising a temperature of tissue at the location of the actual peak $PEAK_{ACTUAL}$ to more than 42 degrees.

In some embodiments, before entering the one or more non-gaseous surrogate medium(s), an initial wavefront shape of the converging EM waves at the given frequency $\omega_{GIVEN}$ is substantially cylindrical or substantially shaped as a spherical section.

In some embodiments, the given frequency $\omega_{GIVEN}$ less than 10 megahertz or less than 1 megahertz.

It is now disclosed an apparatus for irradiating biological tissue, the apparatus comprising: one or more non-gaseous surrogate medium(s), b. a source of converging EM waves at one or more EM frequency(ies) less than 2 Gigahertz configured to direct the converging EM waves into the one or one or more non-gaseous surrogate medium(s) so that the converging EM waves enter the one or more non-gaseous surrogate medium(s), traverse the one or more non-gaseous surrogate medium(s), and exit the one or more non-gaseous surrogate medium(s), wherein: i. geometrical and/or optical properties of the one or more non-gaseous surrogate medium(s) can be defined terms of a uniform cubic object having: A. a side length of 50 cm; B. a cube object refractive index $n_{CUBE\_OBJECT}$ at a given frequency $\omega_{GIVEN}$ of the radiation frequency(ies) that is definable relative to a refractive index $n_{HUMAN-SOFT-TISSUE}$ of human soft tissue at the given frequency $\omega_{GIVEN}$ such that: I. a minimal value of $n_{CUBE\_OBJECT}$ is $$\frac{n_{HUMAN\_SOFT\_TISSUE}}{\text{tolerance\_multiple}};$$

II. a maximum value of $n_{CUBE\_OBJECT}$ is tolerance_multiple*$n_{BIOLOGICAL-TISSUE}$; and III. a value of tolerance_multiple is at most 2; C. a cube object location and orientation relative to converging EM waves at the given frequency $\omega_{GIVEN}$ that traverse the one or more non-gaseous surrogate medium(s) so that, in an initial state before traversing the one or more non-gaseous surrogate medium(s), the converging EM waves at the given frequency $\omega_{GIVEN}$ are initially focused to a convergence peak $PEAK_{INITIAL\_Focus}$ whose location is situated exactly 5 cm beneath a center of one of the cube faces and whose peak width $PW_{INITIAL\_FOCUS}$ is at most 5 cm, an optical path to the convergence peak $PEAK_{INITIAL\_FOCUS}$ traversing the one or more non-gaseous surrogate medium(s); ii. the geometrical and/or optical properties of the one or more non-gaseous surrogate medium(s) are such that when the converging EM waves at the given frequency $\omega_{GIVEN}$ are initially focused to the a location of $PEAK_{INITIAL\_FOCUS}$, converging the converging EM waves at the given frequency $\omega_{GIVEN}$ which actually enter the cube via are focused within the cube so that an actual convergence peak $PEAK_{ACTUAL}$ of energy of the converging EM waves at the given frequency $\omega_{GIVEN}$: has a location that is between 2.5 cm and 7.5 cm beneath the surface of the one of the cube faces and at least 10 cm from all of the other cube faces; and has a peak width $PW_{ACTUAL}$ whose magnitude is at most 5 times the initial focus peak width $PW_{INITIAL\_FOCUS}$ In some embodiments, a magnitude of a peak width $PW_{ACTUAL}$ of the actual convergence peak $PEAK_{ACTUAL}$ has a magnitude that is at most twice the initial focus peak width $PW_{INITIAL\_FOCUS}$.

In some embodiments, the geometrical and/or optical properties of the one or more non-gaseous surrogate medium can be further defined terms of a uniform cubic object such that:

i. in a hypothetical absence of all of the one or more non-gaseous surrogate medium(s) so that all space via which converging EM waves propagate outside of the biological tissue is hypothetically a uniform medium having a refractive index of exactly one at the given frequency $\omega_{GIVEN}$, EM energy enters the unit cube such that a hypothetical convergence peak $PEAK_{HYPOTHETICAL}$ of converging EM waves at the given frequency $\omega_{GIVEN}$ has a peak width $PW_{HYPOTHETICAL}$; and ii. an actual-hypothetical-peak-width-ratio between $PEAK_{ACTUAL}$ and is $PW_{HYPOTHETICAL}$ at most 0.5

It is now disclosed a non-invasive method of heating tissue of a live human subject using electromagnetic (EM) energy, the method comprising: a. for a target location range that comprises a spherical region having a radius of less than 5 cm, each location within the target location range being buried beneath all external and internal skin surfaces of the human subject by at least 1 cm, selecting any target location within the target range; and b. without any solid objet penetrating the skin of the human subject towards the target location, heating the any selected target location by using externally-delivered EM energy radiating from outside the body of the human subject so as to heat the any selected target location to a temperature that exceeds 42 degrees Celsius while all locations within the human subject that are displaced from the selected target location by more than 2 cm are maintained at a temperature that is less than 42 degrees C.

In some embodiments, a non-invasive method of heating a target tissue of a live human subject using electromagnetic (EM) energy, the method comprising:
Without any solid object penetrating skin of the human subject, heating a buried target location that is beneath all external and internal skin surfaces of the human subject by at least 1 cm using externally-delivered EM energy from outside the body of the human subject so as to heat the selected target location to a temperature that exceeds 42 or exceeds 45 or exceeds 50 or exceeds 70 or exceeds 100 degrees Celsius such that:
  i. all locations within the human subject that are displaced from the selected target location by more than 2 cm are maintained at a temperature that is less than 42 degrees; and ii. for every patch of skin surface of the human patient whose area is 75 cm^2 and boundary is a circle via which at least 10% of the tissue-heating EM energy passes, a center of a best spherical section approximation to the patch of skin surface is displaced from the actual convergence peak location by at least 1 cm.

In some embodiments, method of treating neural tissue of a mammalian subject, the method comprising:
transmitting low-frequency low-intensity CW electromagnetic (EM) energy having very low frequency(ies) below 10 Mhz into the mammalian subject's body so that a peak intensity of the transmitted low frequency EM energy occurs within neuronal tissue at a depth of at least 2 cm beneath the skin surface above the neural tissue so as to stimulate and/or depolarize neurons in the vicinity of a location of the peak intensity wherein:
  iii) the non-invasive method is carried out without mechanically penetrating beneath the skull; and
  iv) a peak intensity of the low-intensity CW within the patient's body is below a threshold needed to induce necrosis or apoptosis in neural cells of the neural tissue.

It is now disclosed a method of heating tissue of a live human subject using electromagnetic (EM) energy, the method comprising: without penetrating skin of the human subject, stimulating neurons at a buried target location that is beneath all external and internal skin surfaces of the human subject by at least 1 cm using externally-delivered EM energy from outside the body of the human subject such that: no locations within the human subject that are displaced from the selected target location by less than 5 cm and more than 2 cm are subjected to neuron-stimulating EM radiation; and i. for every circular patch of skin of the human patient whose area is 75 cm^2 via which at least 10% of the tissue-heating EM energy passes, a center of a best spherical section approximation of the circular patch of skin is displaced from the actual convergence peak location by at least 1 cm.

It is now disclosed a method of irradiating tissue:
a. determining a target depth underneath the tissue surface;
b. in accordance with the determined depth, locating and/or orienting a substantially spherical and/or Poynting-vector-matching-portion(s) of a bounding surface bounding a surrogate medium whose refractive index, for at least one of frequency that is less than 2.4 Gigahertz, a refractive index of the surrogate medium $n_{SURROGATE-MEDIUM}$ is at least one half of a refractive index of the biological tissue $n_{BIOLOGICAL-TISSUE}$; and
c. causing converging EM waves to enter into the surrogate medium via the bounding surface of the surrogate medium, to traverse the surrogate medium, and to enter into the biological tissue to irradiate where biological tissue.

In some embodiments, the target depth is determined in accordance with an ultrasound image, an NMR image, a CAT scan, an x-ray or any other medical image.

It is now disclosed a method of neuron irradiation comprising:
generating EM radiation having a frequency-dependent power profile determined in accordance with one or more resonance frequencies of mammalian neural cell(s) and/or neural tissue; and
causing the EM radiation generated outside of the mammalian subject to propagate outside of a mammalian subject and to subsequently penetrate the skin of the mammalian subject so as to irradiate neuron(s) of the live, mammalian subject.

In some embodiments:
iii. the frequency-dependent power profile is such that for a given resonance frequency band having a peak value PV and a peak width PW, a radiation power of at least one resonance frequency exceeds by at least a factor p a radiation intensity at any off-peak frequency that deviates from the peak width by at least twice the peak width and at most three times the peak width; and
iv. a value of p is at least 2 or at least 5 or at least 10 or at least 50.

In some embodiments, the EM radiation include converging EM waves of radiation.

In some embodiments, the EM converging waves are generated using an ellipsoidal reflector.

In some embodiments, the radiation is administered to produce a peak location at a depth exceeding 1 cm beneath the skin.

In some embodiments, the radiation is administered to produce a peak location at a depth exceeding 2 cm beneath the skin.

In some embodiments, the radiation is administered to produce a peak location at a depth exceeding 3 cm beneath the skin.

In some embodiments, the radiation is administered to produce a peak location at a depth exceeding 5 cm beneath the skin.

In some embodiments, the radiation is administered to produce a peak location at a depth d beneath a skin surface and a peak width PW around the peak location such that a ratio between the peak width PW and the depth d is at most 0.5.

In some embodiments, the ratio is at most 0.3 or at most 0.1.

In some embodiments, the irradiation of the neurons is sufficient to cause at least a 10% change in some neural cell membrane potential.

In some embodiments, the irradiation of the neurons is sufficient to cause depolarization and/or stimulate the neuron(s).

In some embodiments, the EM radiation is CW radiation.

In some embodiments, the EM radiation is applied to irradiate the neuron(s) for at least 30 seconds.

In some embodiments, EM radiation is applied to irradiate the neuron(s) for at least 5 minute or 20 minutes or 60 minutes.

In some embodiments, the EM radiation is applied to a subject's brain.

In some embodiments, the EM radiation is used to stimulate brain pleasure centers.

In some embodiments, the EM radiation is used to improve subject memory.

In some embodiments, the method is used to treat at least one condition selected from the group consisting of: clinical depression, non-clinical depression, dysthymia, bipolar disorder, drug addiction, substance abuse, anxiety disorder, obsessive compulsive disorder, or Parkinson's disease. s In some embodiments, the resonance frequency is less than 1 KHz.

In some embodiments, the resonance frequency is selected from the frequency bands of: 1-4 Hz, 4-8 Hz, 8-13 Hz, 13-30 Hz, 30-100 Hz, 100-250 Hz, and excluding 50 Hz and 60 Hz.

In some embodiments, the resonance frequency selected from the frequency bands of 1-4 Hz, and the neuron is in the frontal cortex.

In some embodiments, the resonance frequency selected from the frequency bands of 8-13 Hz, and the neuron is in posterior regions of head or in the sensorimotor cortex.

In some embodiments, the resonance frequency selected from the frequency bands of 30-100 Hz, and the neuron is in the somatosensory cortex.

It is now disclosed an apparatus comprising: a source of converging EM waves having a frequency-dependent power profile determined in accordance with one or more resonant frequencies of mammalian neural cell(s) and/or neural tissue.

These and further embodiments will be apparent from the detailed description and examples that follow.

BRIEF DESCRIPTION OF THE DRAWINGS

FIGS. 2A-2B illustrate focus points (PRIOR ART).

FIG. 7A-7B illustrate energy-density functions (PRIOR ART).

FIGS. 11, 13, 14A-14B, 15A-15F, 16, 18, 20A-20B, 21A-21F and 22A-22B illustrate systems for irradiating tissue according to some embodiments of the invention.

DETAILED DESCRIPTION OF EMBODIMENTS

Figure 1:
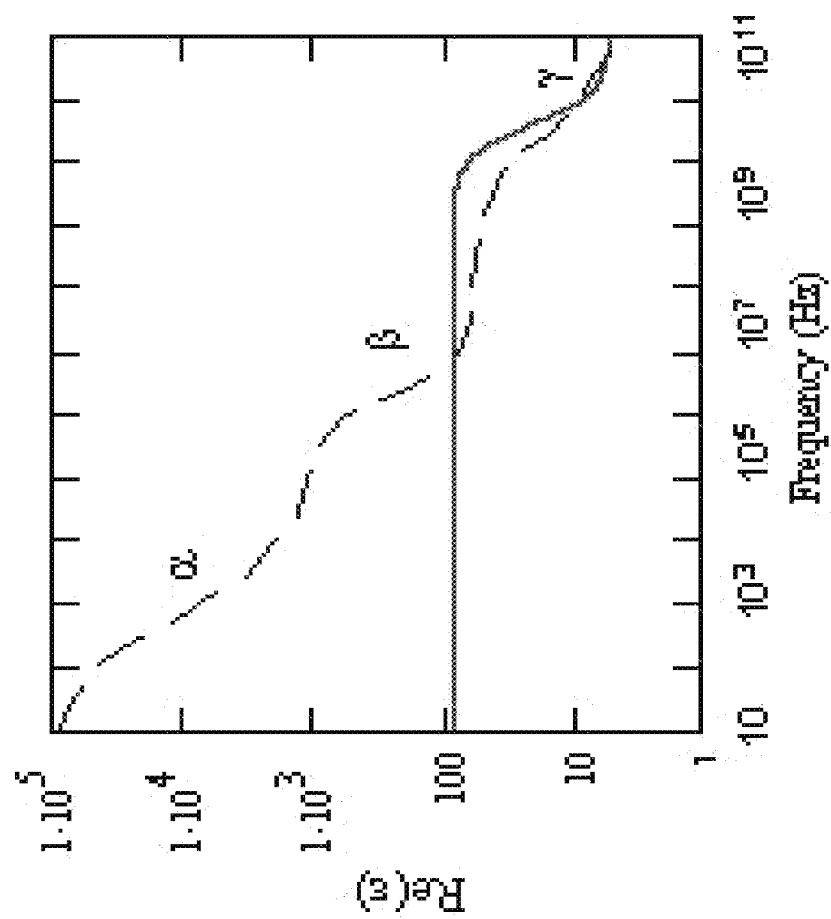
FIG. 1 illustrates the frequency dependence of the dielectric constant $\in$ of dispersion both for biological tissue as well as pure water (PRIOR ART).

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations of these embodiments will be apparent to those skilled in the art. Accordingly, it is intended to embrace all such alternatives, modifications and variations that fall within the spirit and broad scope of the appended claims.

This patent application claims the benefit of U.S. Ser. No. 13,108,924 filed on May 16, 2011, and the benefit of U.S. 61/334,620 filed on May 14, 2010. The disclosure of U.S. Ser. No. 13/108,924 filed on May 16, 2011 is incorporated herein by reference in its entirety.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Throughout, the term "stimulation" is meant to refer to any induced change of activity level, including but not limited to: increased activity, suppressed activity, and increased temperature. For example, "brain stimulation" is referred to both increased brain activity, inhibited brain activity, and combination thereof as measured by various parameters.

The present inventor is now disclosing a method and apparatus for irradiating biological tissue of a live human subject whereby converging EM waves (e.g. of EM radiation whose frequency(ies) is/are less than 10 Gigahertz—e.g. microwave radiation or RF radiation or long RF) enters the biological tissue via a surrogate medium outside of the human body. By employing a 'refractive-index-matching' surrogate medium (i.e. a medium whose refractive-index, at frequency(ies) less than 2 Gigahertz substantially matches that of biological tissue), it is possible to substantially retain a focus of focused EM energy, and to counteract or substantially reduce any biological-tissue-induced defocusing associated with EM radiation propagation into or within the biological tissue. In this manner, it is possible to focus EM radiation from external sources to a relatively 'small' target location in the biological tissue, even a target that is relatively 'deep' beneath the skin of the human subject, while subjecting surrounding biological tissue to a lesser intensity (and desired negligible effect) of radiation.

As was discussed above with reference to FIG. 1, while the refractive index of air remains essentially constant at about $n_{air}=1$, the refractive index of biological tissue may vary as a function of radiation frequency, and be significantly different from that of air. In particular, at frequencies less than 10 GHz (or less than 5 GHz or less than 3 GHz or less than 2 GHZ or less than 1 GHz) the refraction index of biological tissue may significantly exceed that of air. In non-limiting examples, the surrogate medium may be a liquid (e.g. an aqueous liquid such as water, saline solution, etc. . . . ), a gel, a colloid, a solid (e.g. plant tissue or animal tissue), and any natural or artificial material having a cellular-structure. It is appreciated that this list of examples is a non-exhaustive list, and that other materials may be used.

A non-limiting application of this technique includes but is not limited to electromagnetic stimulation of neural tissue (e.g. stimulation of brain tissue or 'deep brain tissue')—this may be useful, for example, for affecting memory, addiction, and mental disorders. Another non-limiting application relates to gland stimulation, for example, to regulate mood or for sexual stimulation or to regulate appetite. Other non-limiting applications include but are not limited to (i) damaging or inducing cell death of malignant cell(s) positioned at a relatively 'deep' location beneath the patient's; (ii) local hyperthermia; (iii) inducing blood coagulation and (iv) RF ablation.

Alternatively or additionally, it may be useful to irradiate neural tissue (for example, brain tissue) by focused or unfocused EM radiation having a power profile (i.e. distribution of EM power as a function of frequency) determined in accordance with one or more neural tissue resonant frequencies. These neural tissue resonant frequencies may include one or more frequencies less than a few kilohertz or less than a kilohertz, or selected from frequencies known in the published literature are: 'brain wave' frequency bands, and resonances in 10-50 Hz and 100-250 Hz frequency bands [Prog Brain Res. 2005; 148:181-8]. Preferred resonances are in the brain wave bands of—

| Type | Frequency (Hz) | Primary Location |
| --- | --- | --- |
| Delta | up to 4 | frontally in adults, posteriorly in children; high amplitude waves |
| Theta | 4-8 | Found in locations not related to task at hand |
| Alpha | 8-13 | posterior regions of head, both sides, higher in amplitude on dominant side. Central sites (c3-c4) at rest. |
| Beta | 13-30 | both sides, symmetrical distribution, most evident frontally; low amplitude waves |
| Gamma | 30-100 | Somatosensory cortex |
| Mu | 8-13 | Sensorimotor cortex |

For example, it may be judicious to irradiate neural tissue so that an intensity of radiation at the resonance frequencies exceeds an intensity of radiation at neighboring frequencies. In some embodiments, it is possible to electronically store (e.g. using any combination or digital electronics, analog electronics and software) value(s) of one or more of these resonant frequencies and to apply radiation to the human subject according to the stored frequency values.

Features related to neural tissue resonance frequencies may be combined with features related to focusing EM radiation and/or features related to surrogate medium introduced above. However, this is certainly not a requirement, and it is possible to irradiate biological tissue (e.g. brain tissue) according to values of neural tissue resonant frequencies without focusing in any manner disclosed herein and/or without utilizing surrogate medium as described herein or in any other manner.

A First Discussion of FIGS. 10-14

Figure 10:
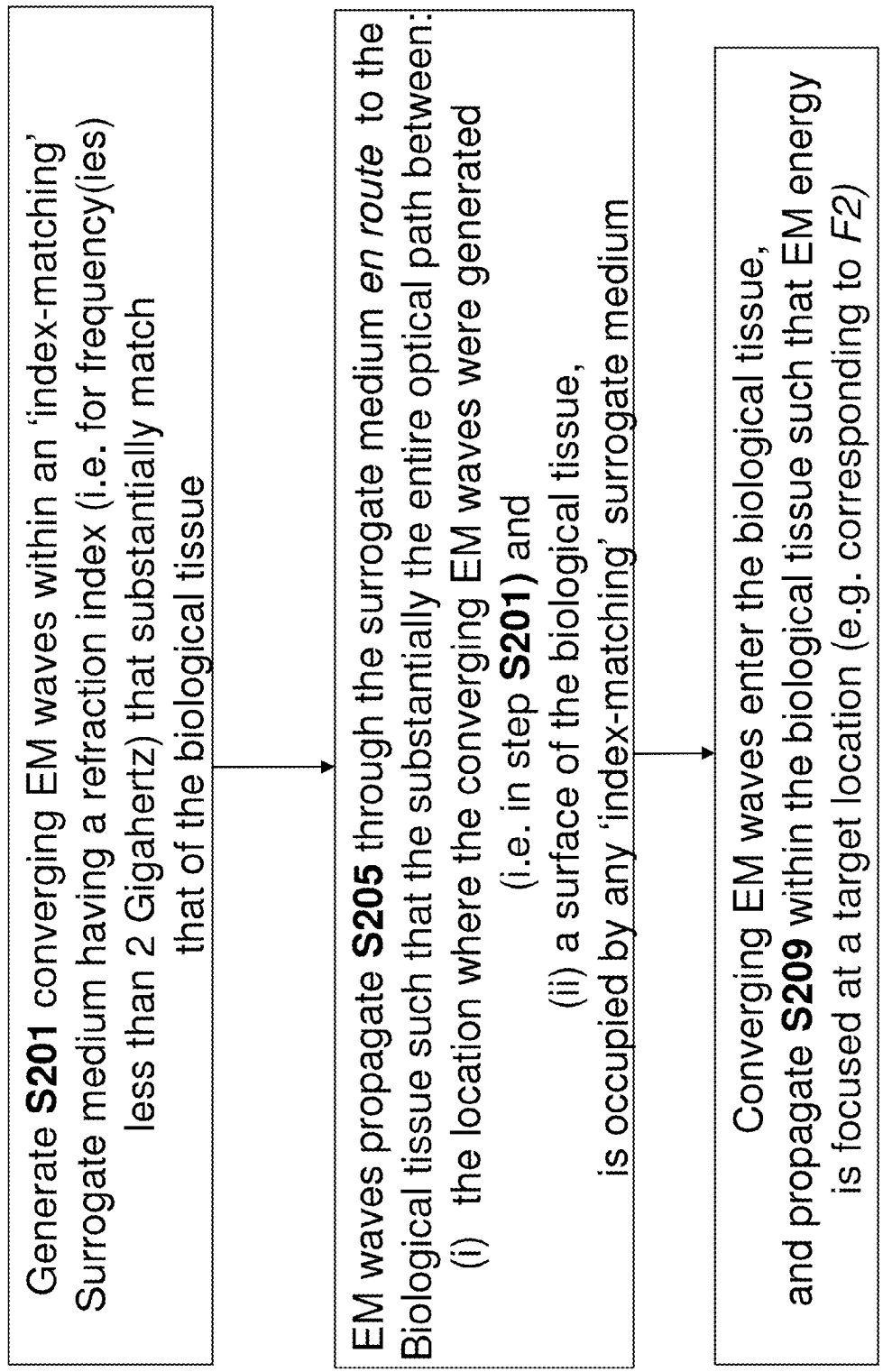
FIGS. 10, 12, and 14C are flowcharts of methods for irradiating tissue according to some embodiments of the invention.
Figure 11:
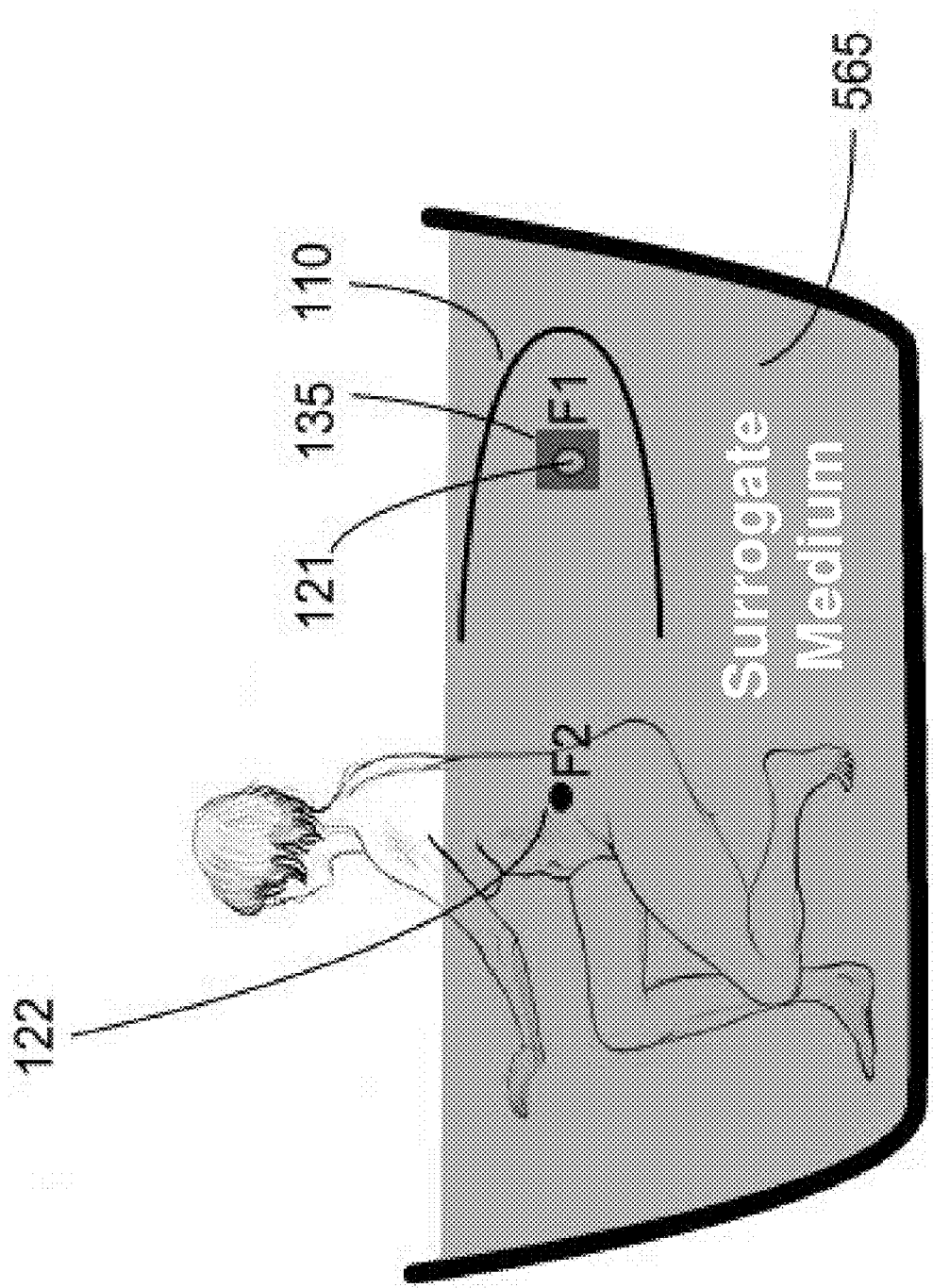

FIGS. 10-11 relate to a first example of a technique of irradiating biological tissue by converging EM waves via a refractive-index-matching surrogate medium whose presence is useful for focusing radiation to a target location beneath the skin of a human subject. According to the first example, converging EM waves are formed at a location within a 'refractive-index-matching' surrogate medium.

Figure 12:
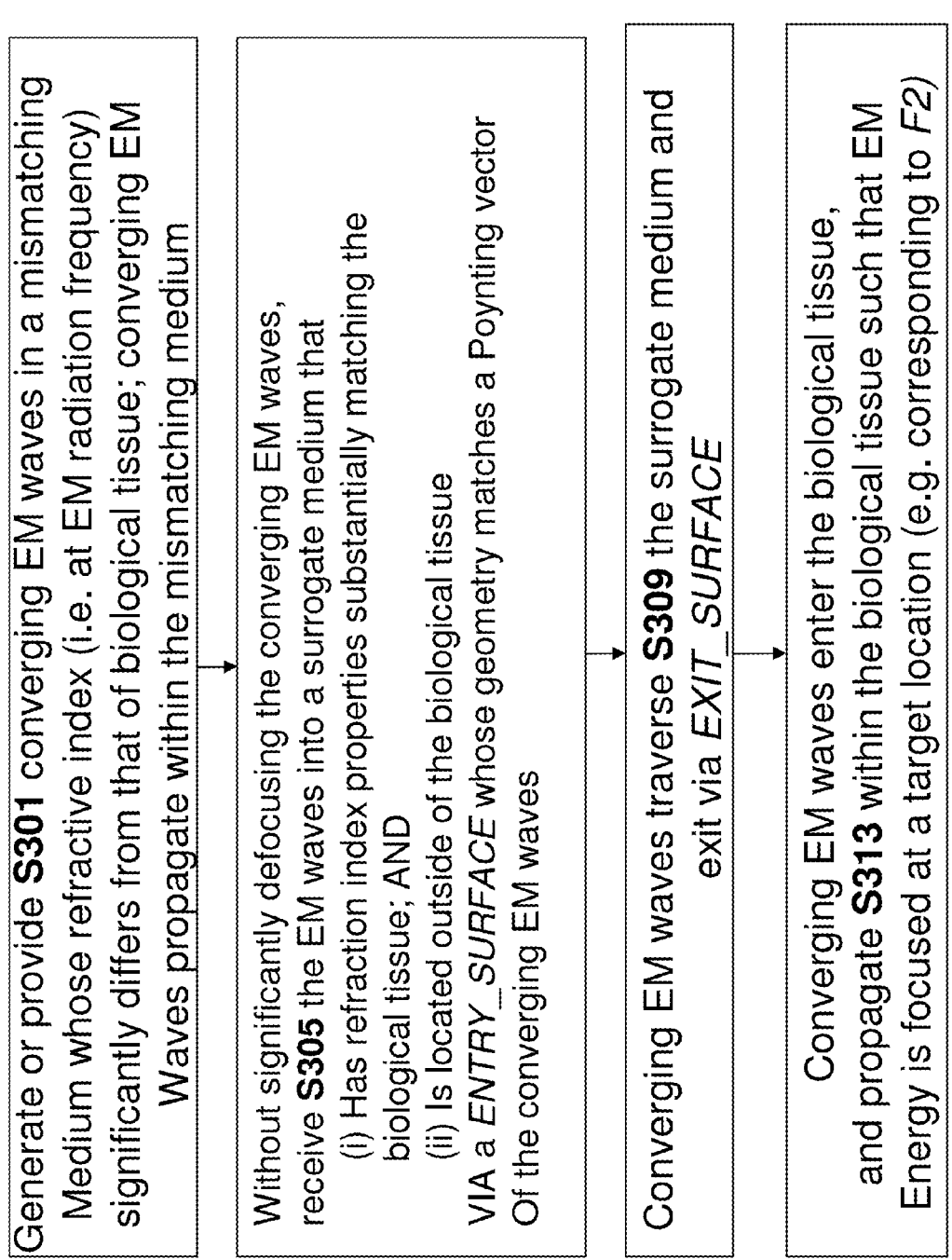
Figure 13:
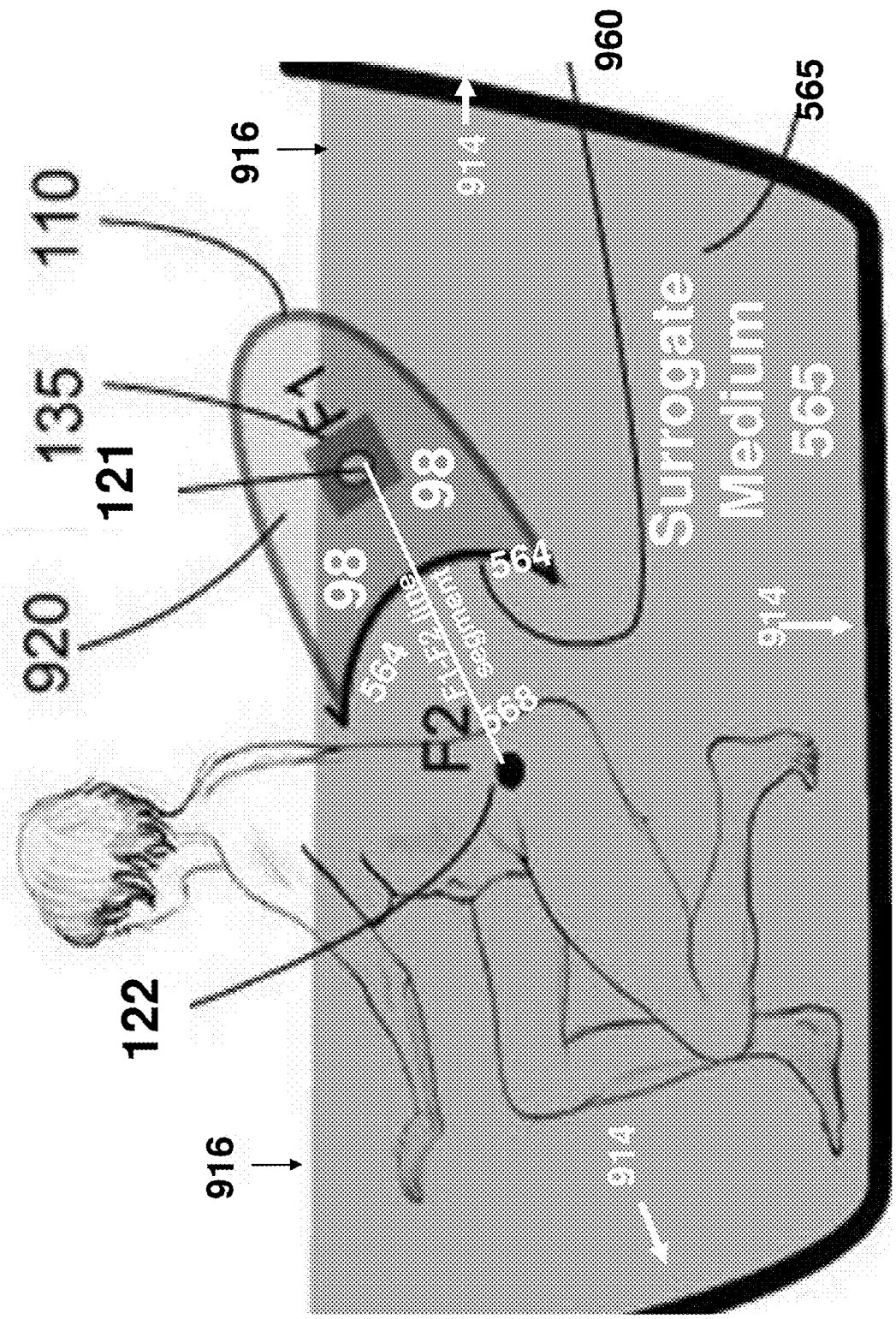

FIGS. 12-14 relate to second example of a technique of irradiating biological tissue by converging EM waves via a refractive-index-matching surrogate medium whose presence is useful for focusing radiation to a target location beneath the skin of a human subject. According to the second example, converging EM waves are formed at a location within mismatching medium whose refractive index does not match that of the biological tissue. The converging EM waves traverse an index-matching surrogate medium en route to the biological tissue via a ENTRY_SURFACE of the index-matching medium that provides geometric properties determined in accordance with the Poynting vector of the converging EM waves.

As explained more elaborately in the 'definition section' below: A surface shape match to or in accordance with the Poynting vector of EM wave is characterized in that the local normal (i.e., perpendicular) to the surface is substantially parallel to the local Poynting vector of EM wave crossing at that surface point.

FIG. 10 is a flow chart of a routine for irradiating biological tissue whereby converging EM waves are formed at a location within a 'refractive-index-matching' surrogate medium. FIG. 11 illustrates one implementation whereby at least a portion of skin of the human subject, an EM radiation source 135, and an ellipsoidal mirror 110 are all submerged within the surrogate medium (e.g. in a liquid or gel or colloid or other index-matching surrogate medium).

In step S201, converging EM waves having frequency(ies) of at most 10 Gigahertz (e.g. at most 5 GHz or at most 3 GHZ or at most 2 GHz or at most 1 GHZ or at most 10 MHZ or at most 2 MHZ or at most 1 MHZ) are formed at a location(s) within the refractive-index-matching surrogate medium outside of the human subject. In the non-limiting example of FIG. 11, this is accomplished by irradiating by diverging EM waves (e.g. generated by radiation source 135 positioned at focus F1 121) a surface of an ellipsoidal reflector 110 at a time when the ellipsoidal reflector surface is submerged in the refractive-index-matching surrogate medium. In step S205, these converging EM waves propagate through the surrogate medium en route to the biological tissue (and en route to the target location) so the converging EM waves only traverse locations whose refractive index (i.e. at frequency(ies) is less than 10 Gigahertz) substantially matches that of the biological tissue. After the traversing the surrogate medium (e.g. in FIG. 11, after travelling through the substance within the reservoir in which the ellipsoidal reflector 110 and a portion of the human subject are submerged), the converging EM waves enter the biological tissue and propagate therein (see step S209 of FIG. 11).

According to this 'first example,' it is possible to avoid a situation whereby converging EM waves directly enter the biological tissue from a 'mismatching' medium (i.e. a medium whose refractive index at frequency(ies) less than 10 Gigahertz differs substantially from that of biological tissue—one example is a gas such as air). As will be discussed below (see, for example, FIG. 17C), when converging EM waves directly enter the biological tissue from a 'mismatching' medium, the energy of the converging EM waves may be defocused.

As noted above, FIGS. 12-14 relate to a 'second example' of a technique whereby converging EM waves enter the biological tissue via the surrogate medium. FIG. 12 is a flowchart of a routine for irradiating biological tissue according to this 'second example.'

FIGS. 13-14 illustrate non-limiting example implementations of the routine of FIG. 12. In the example of FIG. 13, converging EM wave device comprises an ellipsoidal reflector 110, a source 135 of EM radiation having frequency(ies) of less than 10 Gigahertz located at focus F1 of the ellipsoidal reflector, and a lid 964 shaped like a spherical section is submerged within the surrogate medium. The inner region 920 of the converging EM wave device is bounded by lid 960 and by ellipsoidal reflector 110—this inner region 920 is occupied by a non-matching medium (e.g. a gas such as air) 98. In the example of FIG. 14, neither the human subject nor the ellipsoidal reflector are submerged within surrogate medium 565.

Reference is now made to FIG. 12. In step S301 converging EM waves are formed in a 'mismatching medium' 98 (e.g. a gas such as air). Although this routine is certainly not limited to ellipsoidal-reflector embodiments, in one implementation of step S301, EM radiation source 135 located at one focus F1 emits diverging EM waves which are reflected from a surface of ellipsoidal reflector 110 to form converging EM waves directed towards the other focus F2. These converging EM waves propagate within the mismatching medium 98.

Subsequently, in step S305, these converging EM waves enter the index-matching surrogate medium 565 via a ENTRY_SURFACE (for example, see 964 of FIG. 13 or 564 of FIG. 14) of the surrogate medium. As will be discussed below in greater detail, geometric properties of this ENTRY_SURFACE are determined according to a Poynting vector of the converging EM waves. In the example of FIG. 13, a shape of the lid 960 determines a shape of this 'ENTRY_SURFACE.'

As will be discussed below (see, for example, the discussion provided with reference to FIGS. 15-16), by shaping the ENTRY_SURFACE to match the Ponyting vector, it is possible for converging EM waves to cross from a first medium (e.g. mismatching medium 98) to a second medium (e.g. surrogate medium 565) having a refractive index that significantly differs from the first medium such that the Poynting vector without significantly defusing the converging EM waves.

In step S309 of FIG. 12, the converging EM waves traverse the surrogate medium and then exit via a EXIT_SURFACE (for example, see 968 of FIG. 13 or 568 of FIG. 14). In the example of FIG. 13, this EXIT_SURFACE is an interface between the patient's skin and the flowable matter within the reservoir; in the example of FIG. 14, this EXIT_SURFACE is the bottom surface of the surrogate medium object deployed on the person's head.

Figure 14A:
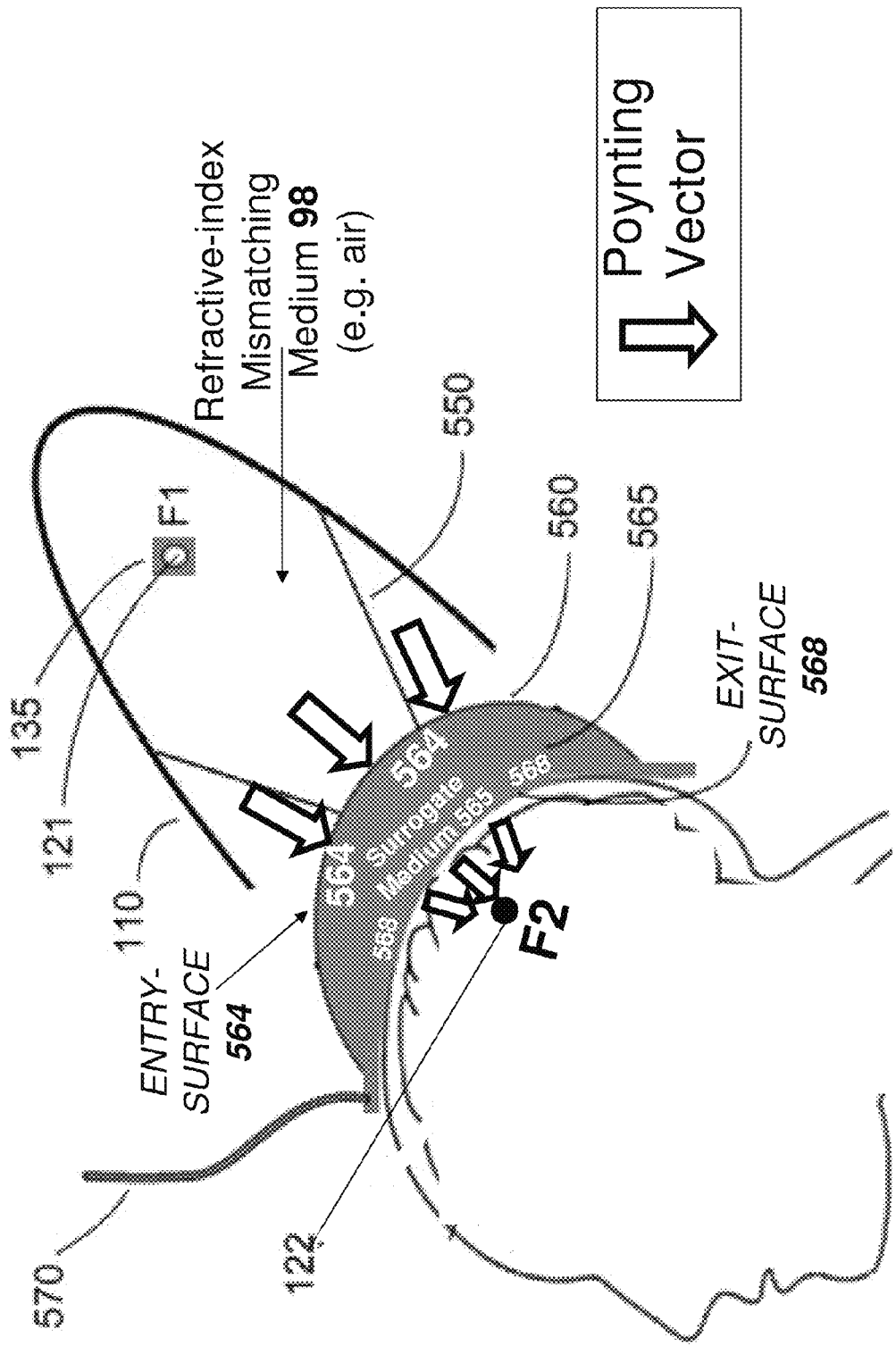
Figure 14B:
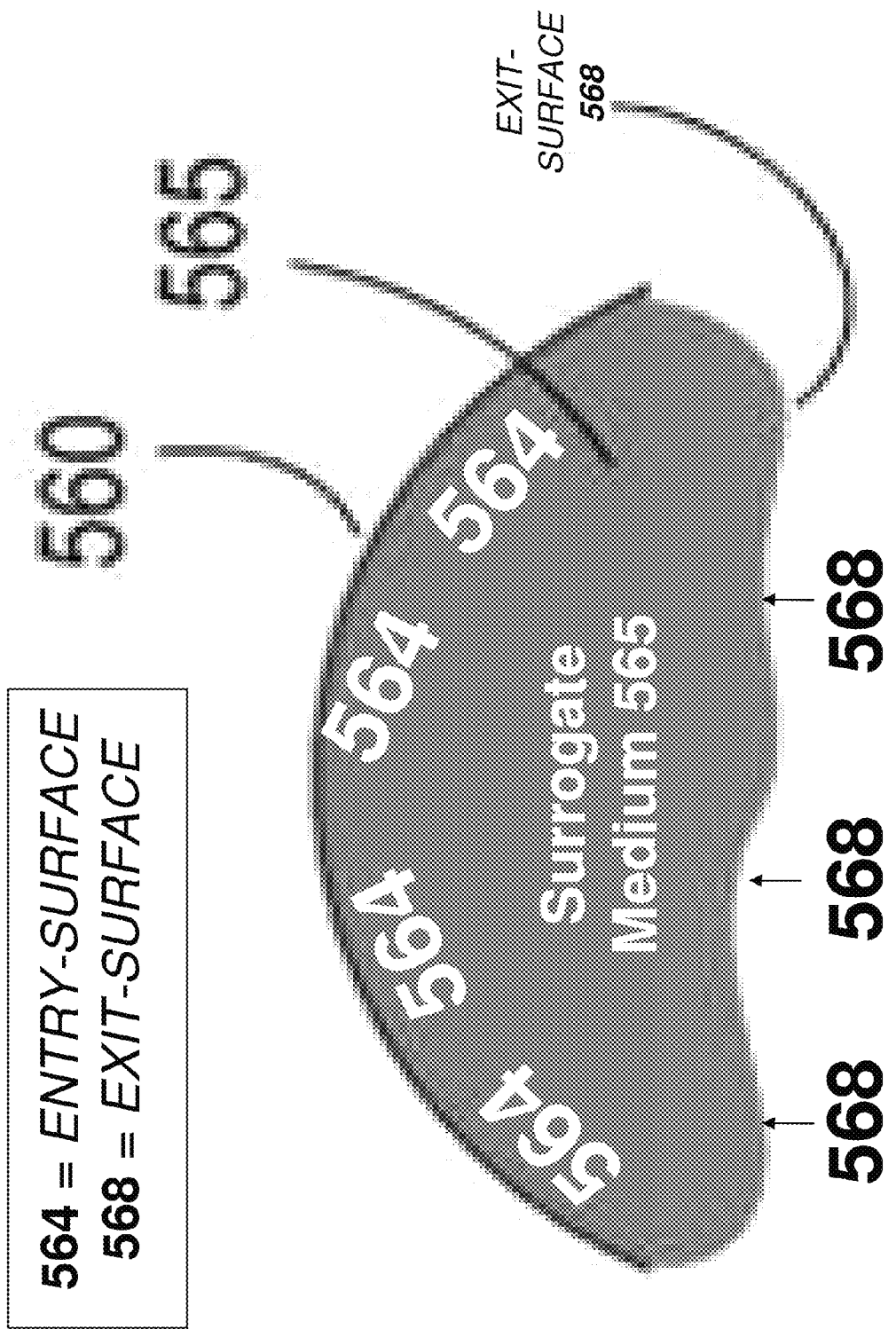

FIGS. 14A-14B illustrate an apparatus for focusing EM radiation at a target location beneath the surface of the biological tissue. The apparatus of FIG. 10A includes: (i) an ellipsoidal reflector 110 configured to reflect diverging waves of EM radiation from EM radiation source 135 so as to form converging waves of EM radiation; (ii) a surrogate medium having ENTRY-SURFACE 564 that is shaped so as to facilitate focusing of the EM radiation within the biological tissue; and (iii) a rod 550 which mechanically constrains a position and/or orientation of at least a portion of surrogate medium 565 and/or a surface 564 thereof relative to ellipsoidal reflector 110.

This may be useful for holding at least a portion of ENTRY-SURFACE 564 (e.g. a 'power-significant' portion thereof) in a position so as to reduce defocusing of the converging EM waves en route to a focus location within the biological tissue. For example, as will be discussed below, the 'power significant' portion of ENTRY-SURFACE 564 may be located so that a local normal line passes close to F2 and/or a local Poynting vector as locations of the 'power-significant' portion are perpendicular to ENTRY-SURFACE 564.

It is appreciated that not every illustrated element is required—e.g. some embodiments lack a connecting element (e.g. rod 550) between surrogate medium 565 and ellipsoidal reflector. Furthermore, the shape of rod 550 is intended as illustrative and not limiting.

As illustrated in FIG. 14A, (i) at least a portion of EM source 135 (i.e. an EM-radiation-emitting location) is proximate (i.e. at most 3 cm or at most 2 cm or at most 1 cm) to one of the foci (e.g. F1 121) and/or (ii) a centroid of EM source 135 is proximate to one of the foci (e.g. F1 121). For example, if EM source 135 includes a loop or coil, at least one location of the loop or coil and/or a centroid thereof may be proximate to one of the foci.

In some embodiments related to FIG. 14A (or to any other 'ellipsoidal reflector embodiment'), radiation source 135 may be relatively 'small'—for example, have a (i) characteristic length that is at most 25% or at most 20% or at most 10% or at most 5% or at most 2.5% or at most 1.5% or at most 1% of a wavelength of radiation transmitted therefrom and/or (ii) at most 3 cm or at most 2 cm or at most 1 cm or at most 5 mm or at most 3 mm or at most 2 mm or at most 1.5 mm or at most 1.5 mm and/or (iii) at most 20% (or at most 15% or at most 10% or at most 5%) of a distance between foci (i.e. the distance between F1 121 and F2 122).

In some embodiments, the surface of medium 565 which is facing towards F2 is bounded (or at least a portion thereof)—i.e. EXIT_SURFACE 566—is malleable or elastic boundary 566. In some embodiments, surrogate medium 565 is itself malleable or elastic. Thus, in some embodiments, EXIT_SURFACE or a power-significant portion thereof may conforms to the human subject body contour when pressed against it.

In some embodiments, it may be desired to both (i) a regulate a location of where EM radiation is focused within the biological tissue and/or a depth thereof and (ii) regulate the location in a manner which minimizes the defocusing or distortion of the radiation en route to the focus location. In some embodiments, this may be accomplished by moving both: (i) a location of ellipsoidal reflector 110 relative to the biological tissue and (ii) a location of ENTRY_SURFACE (or an energy-significant portion thereof) so that ENTRY_SURFACE remains properly aligned with a 'target location' where energy is to be focused. For one example of (ii), see step S355 of FIG. 14C.

Figure 14C:
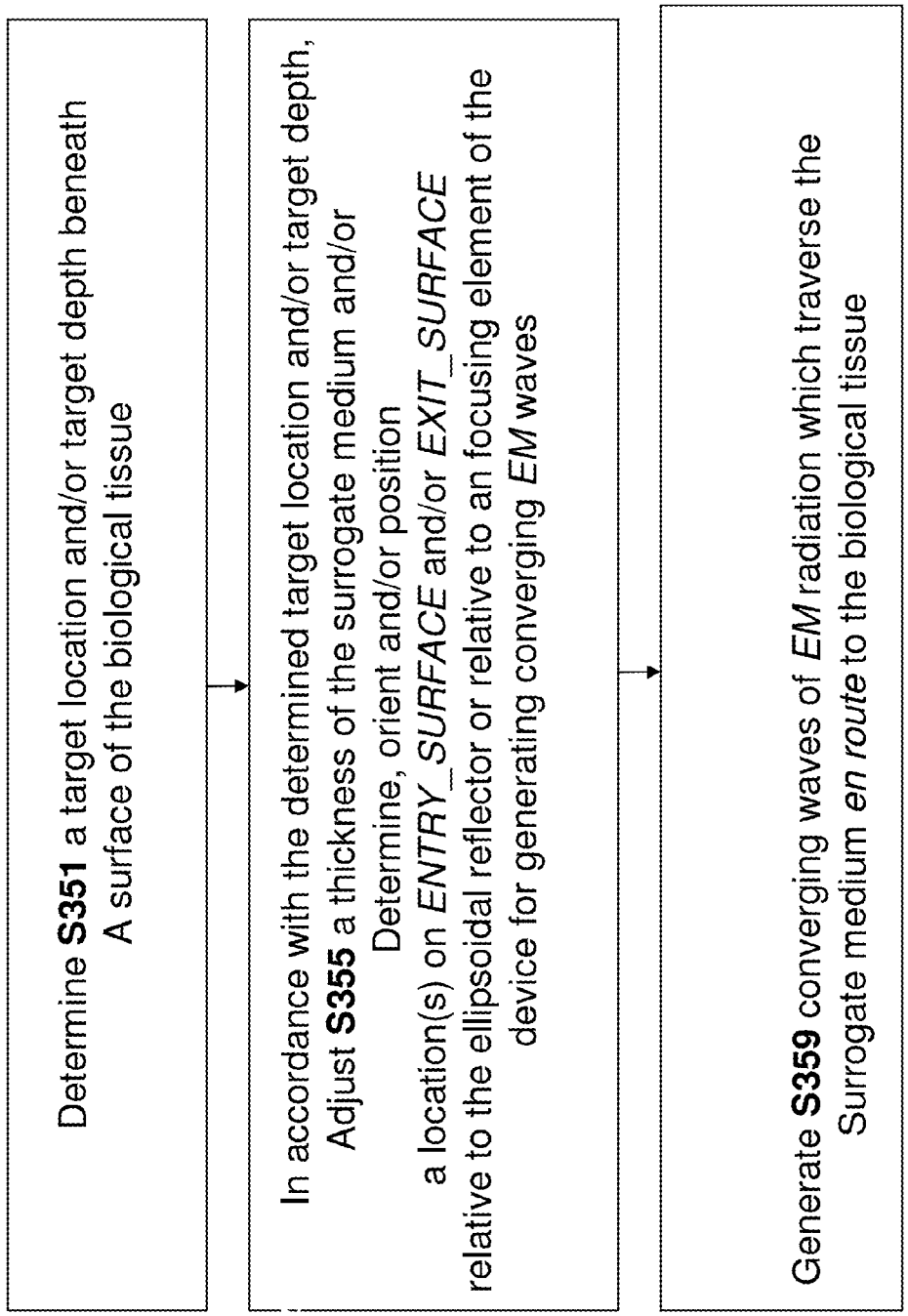

Reference is made to FIG. 14C. In step S351, a target location and/or depth beneath a surface of the biological tissue is determine. In step S355, in accordance with the determined target location or depth, it is possible to configure and/or adjust ENTRY_SURFACE and/or EXIT_SURFACE or (i) a location thereon; or (ii) a power-significant-portion thereof.

In one non-limiting example related to both FIG. 13 and to step S355 of FIG. 14C, the location or depth of the focus location coincides with F2 122 within the biological tissue. In this example, it is possible to determine a target location or depth in the biological tissue and then to orient and position ellipsoidal reflector 110 so that the target location coincides with F2 122. Because the lid is mechanically coupled to ellipsoidal reflector 110 and moves in tandem therewith, when ellipsoidal reflector 110 is thus oriented and position, the lid is also oriented and positioned so that a sphere center thereof (i.e. since the lid is shaped like a spherical section it defines a sphere center) also is co-located and/or coincides with the target depth or location. Since the surrogate medium 565 in FIG. 13 is flowable, the outersurface of lid defines ENTRY_SURFACE of the surrogate medium 565. As such, by positioning lid, this also oriented and/or positions ENTRY_SURFACE of the surrogate medium 565.

In one non-limiting example related to both FIG. 14A and to step S355 of FIG. 14C, the location or depth of the focus location coincides with F2 122 within the biological tissue. In this example, it is possible to volume of the surrogate medium 565 contained between ENTRY_SURFACE 564 and EXIT_SURFACE 566 (and thus the 'thickness' of surrogate medium 5650 can be varied by inflow or outflow of the medium n3 volume via an inlet lumen 570.

In both the example of FIGS. 13 and 14A, at least one location of EXIT_SURFACE 566 is (i) located on an F1-F2 line segment and (ii) is movable along the F1-F2 line segment relative to the ENTRY_SURFACE 564 (or to an energy-significant portion thereof) over a 'range' that is at least 1 mm or least 2 mm or at least 5 mm or at least 1 cm or at least 2 cm or at least 5 cm. This 'movability feature' may be useful for controlling a location and/or depth of the focused radiation within the biological tissue in a manner that allows use of the surrogate medium 565 to reduce or minimize or substantially eliminate defocusing A Discussion of FIGS. 15A-15F FIG. 15A is a closeup of portions of the apparatus of FIG. 14A The Poynting vector of the converging EM radiation, and F1-F2 line segment, are both illustrated. FIG. 12B illustrates just ENTRY_SURFACE 564.

Clearly, as illustrated in FIG. 15C, little or no power of converging EM waves from ellipsoidal reflector 110 traverse certain portions 1050 of ENTRY_SURFACE 564. However, 'power significant portions' of ENTRY_SURFACE 564 may provide certain features. The 'power significant portions' of ENTRY_SURFACE 564 are the portions of ENTRY_SURFACE 564 via which significant fractions (e.g. at least 0.1 or at least 0.2 or at least 0.3 or at least 0.5 of the power of converging EM waves from a source of converging EM waves—e.g. ellipsoidal reflector 110).

Figure 15A:
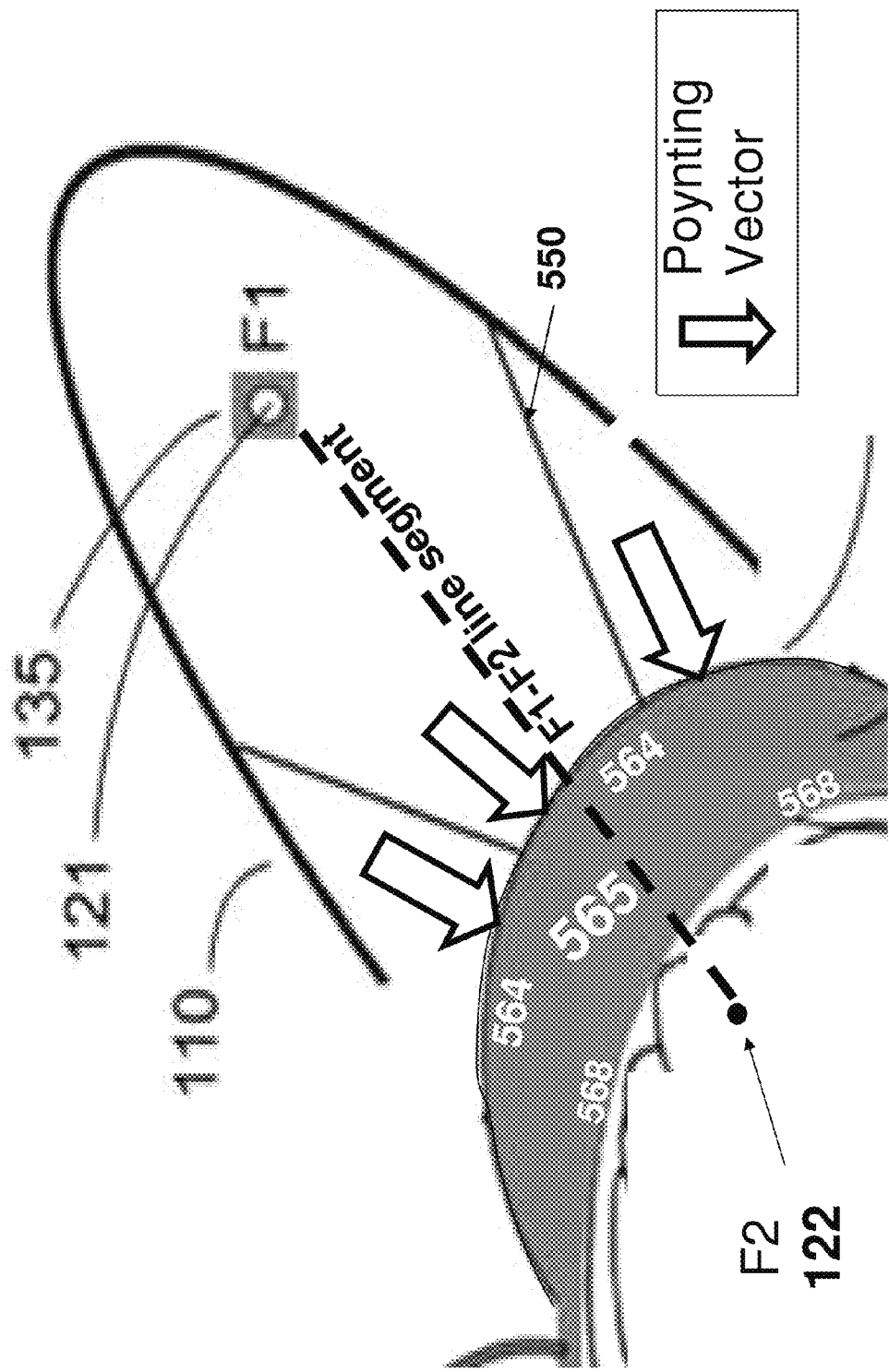
Figure 15D:
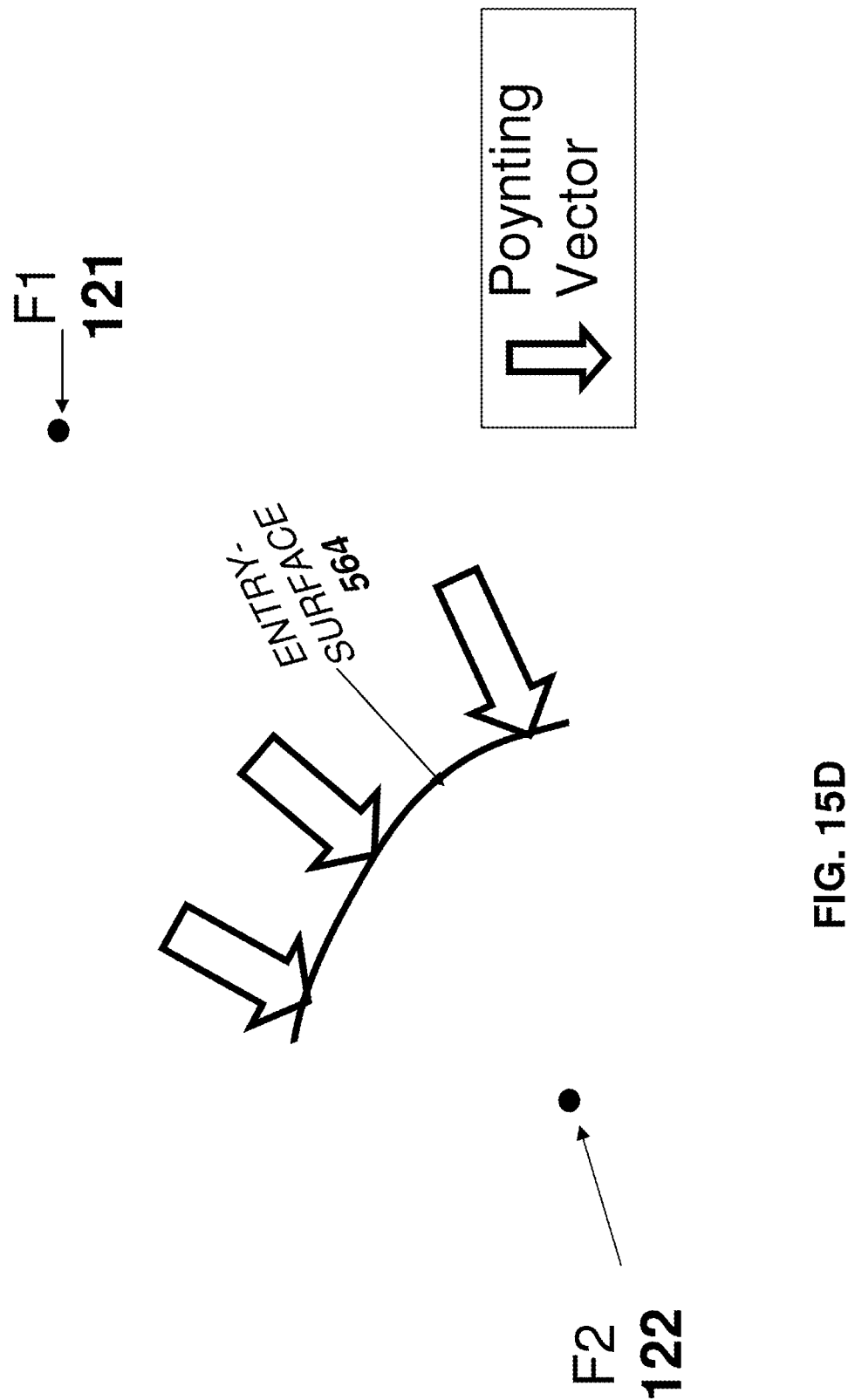
Figure 15E:
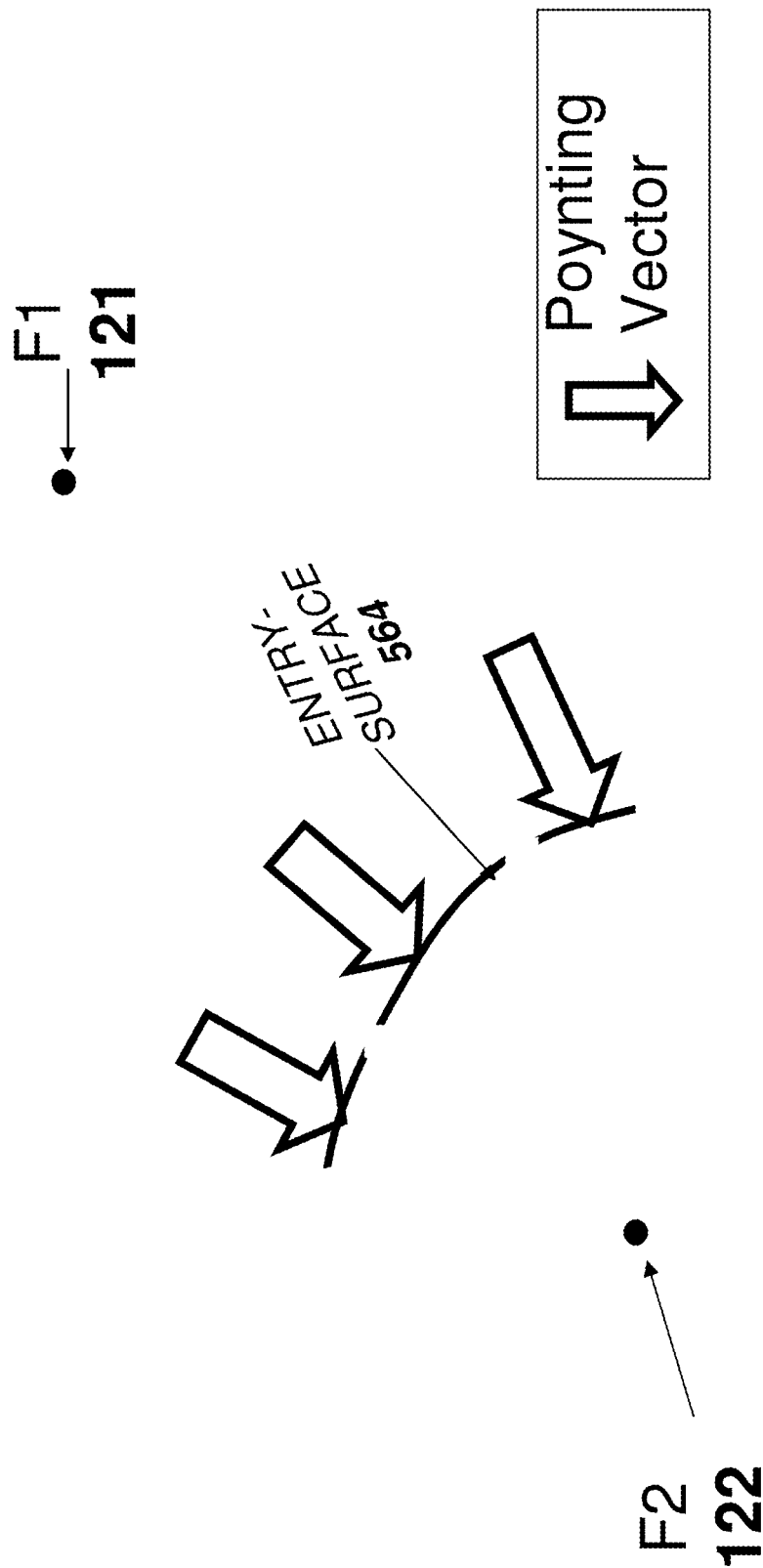

FIG. 15D illustrates one such power-significant portion of ENTRY_SURFACE 564. As illustrated in the figure, at most or all locations of the power-significant portion the Poynting vector is substantially normal to (i.e. perpendicular to) the local ENTRY_SURFACE 564. As illustrated in FIG. 15E, it is possible that the 'power-significant portion' of ENTRY_SURFACE 564 is not, in fact, contiguous.

Figure 15F:
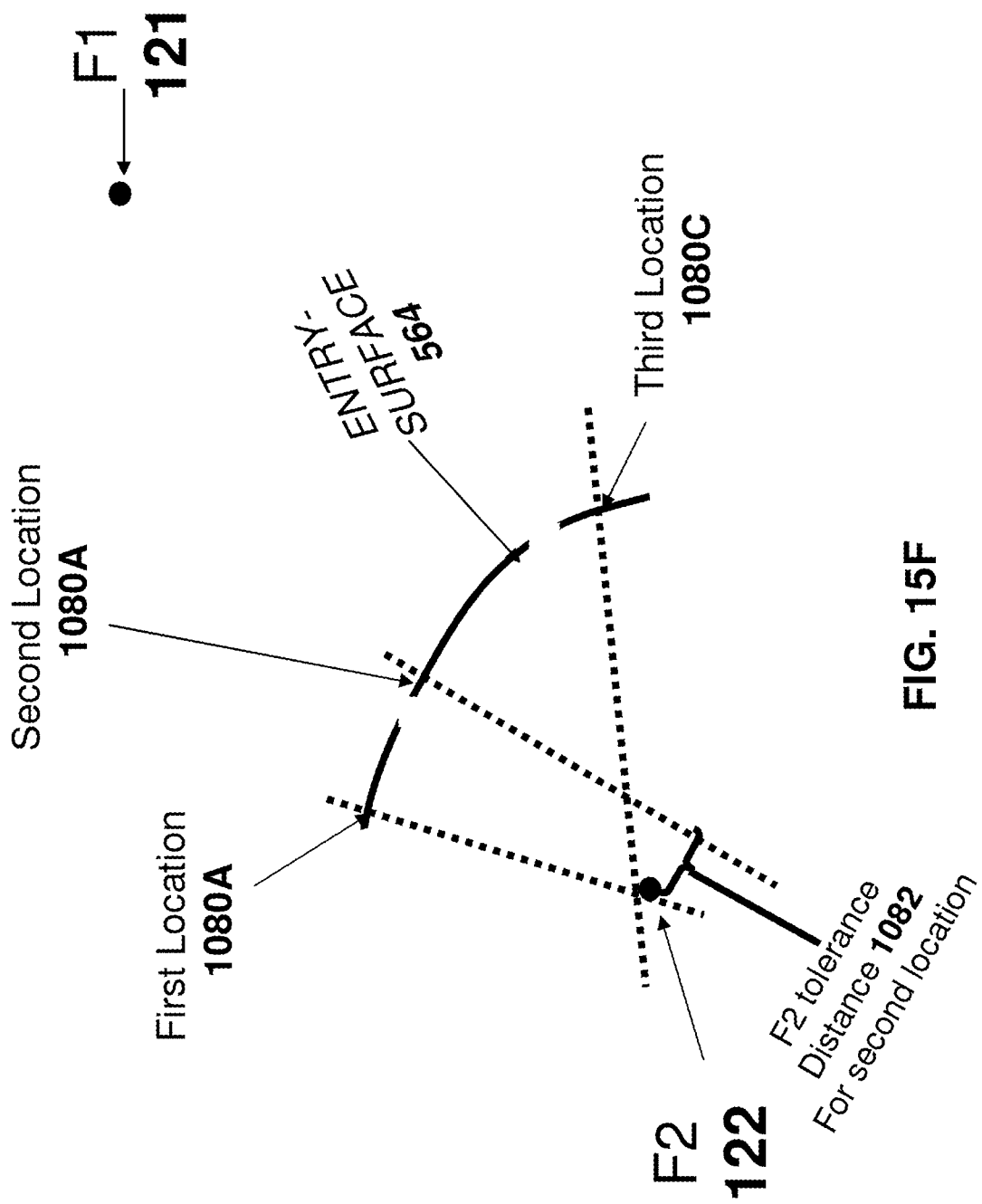

At every location ENTRY_SURFACE 564, a local normal may be defined. The 'line extension' of the local normal is co-linear to the local normal and extends infinitely in both directions. As illustrated in FIG. 15F, for various locations on the power-significant portion of ENTRY_SURFACE 564 the line extension of the normal includes points that are fairly close' to F2.

Although FIG. 15F relates to the specific example of a focus F2 of ellipsoidal reflector, similar features may be provided relative to other focus locations—for example, an 'initial focus location' IFL towards which Em radiation is focused before entering surrogate medium 565.

Figure 16:
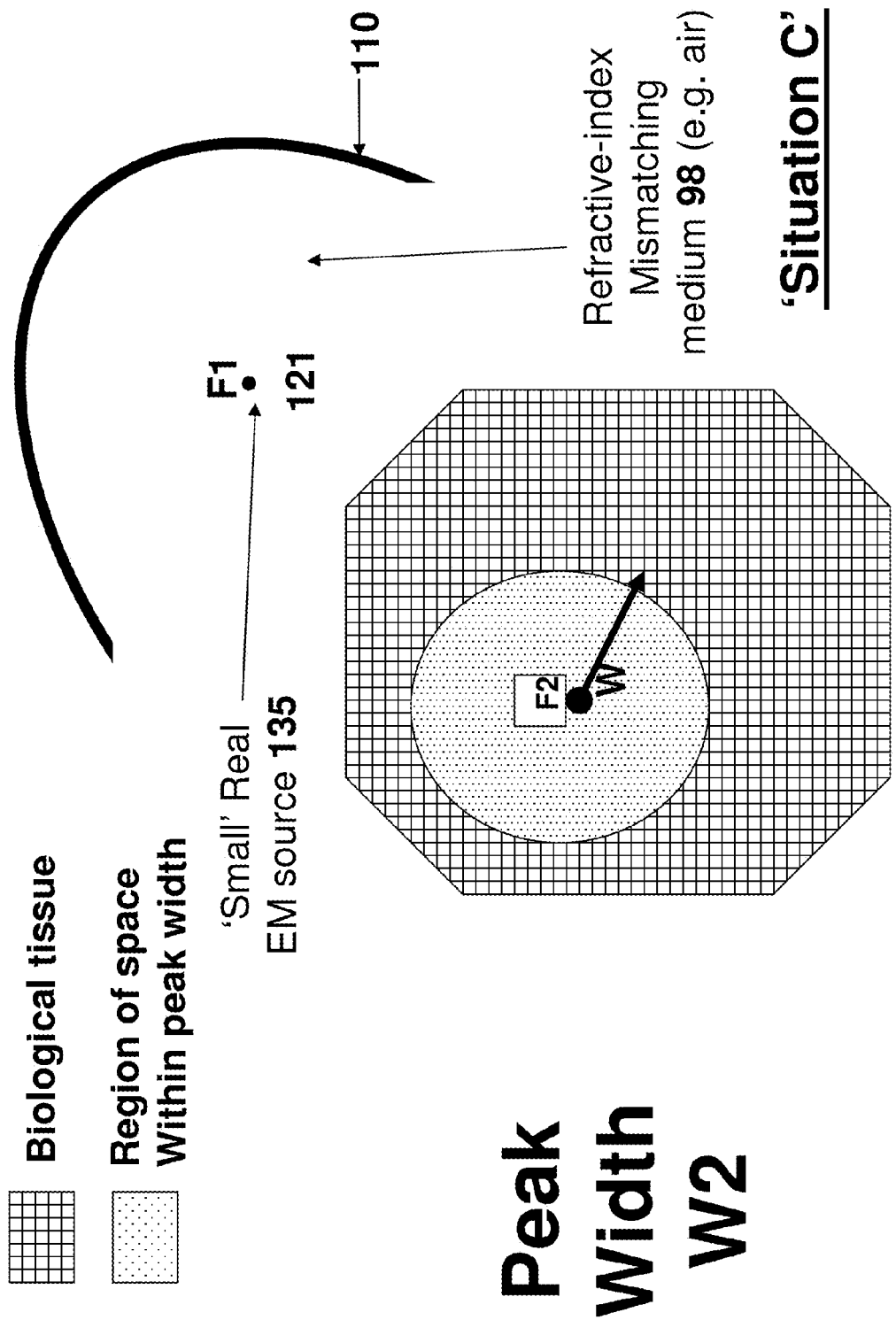

A Discussion of FIGS. 16-167—Refractive Index-Induced Defocusing

In the present section, it will be explained how a presence of biological tissue may, in certain situation, deform a wavefront shape and defocus converging EM waves that, prior to cross a boundary from a mismatching medium into biological tissue, are focused upon a target location within the biological tissue so that the peak width is relatively 'small.'

FIG. 16 illustrates a situation whereby converging EM waves, generated in a mismatching medium 98 by an ellipsoidal reflector, are directed towards a target location corresponding with a second focus F2 122 of the reflector that is located beneath the surface of a shaped piece of biological tissue. The particular example of FIG. 16, informally referred to as 'Situation C.'

Figure 5:
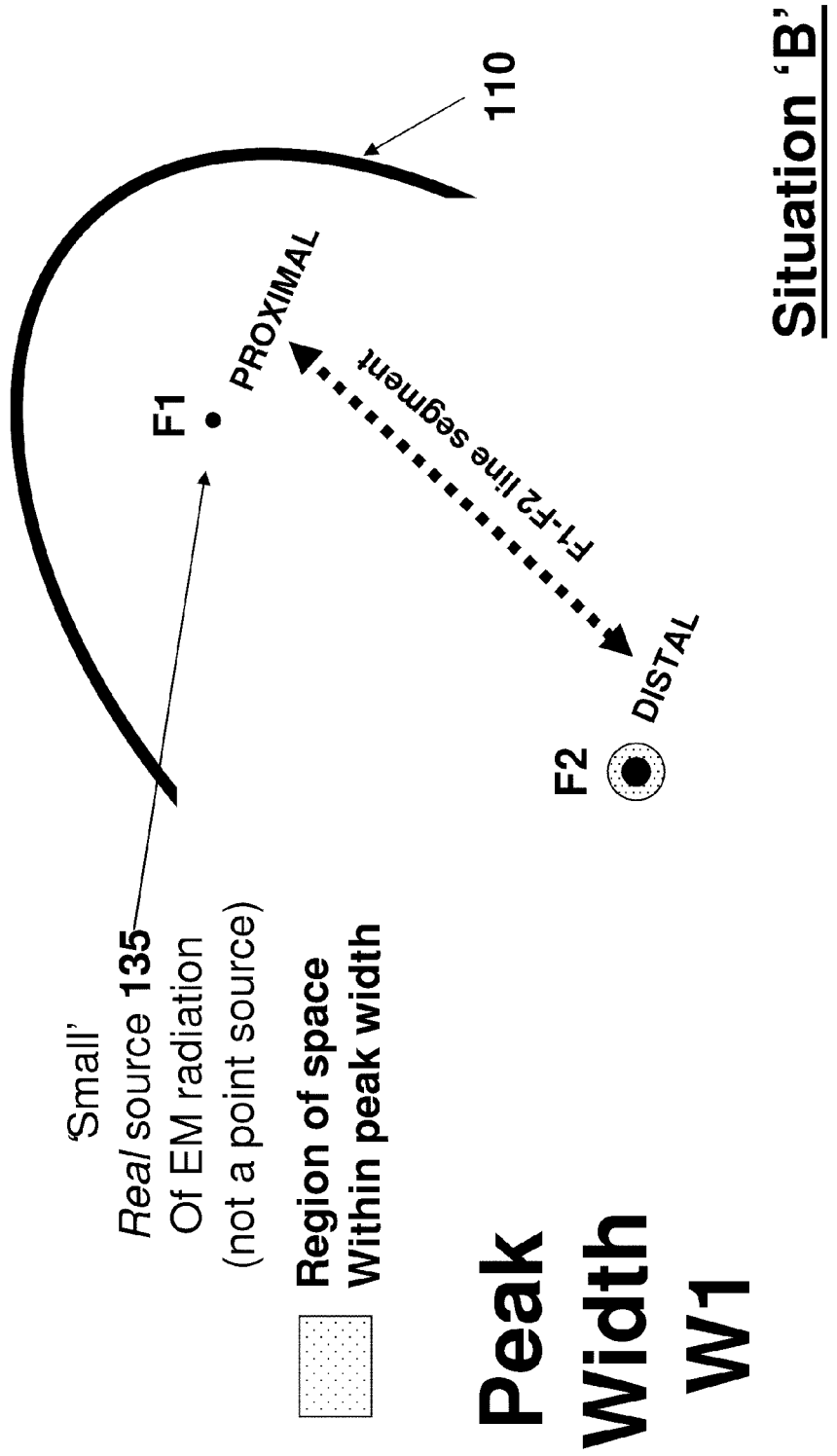
FIG. 5 illustrates a 'real-life' system comprising a source of EM radiation and an elliptical reflector (PRIOR ART).
Figure 6:
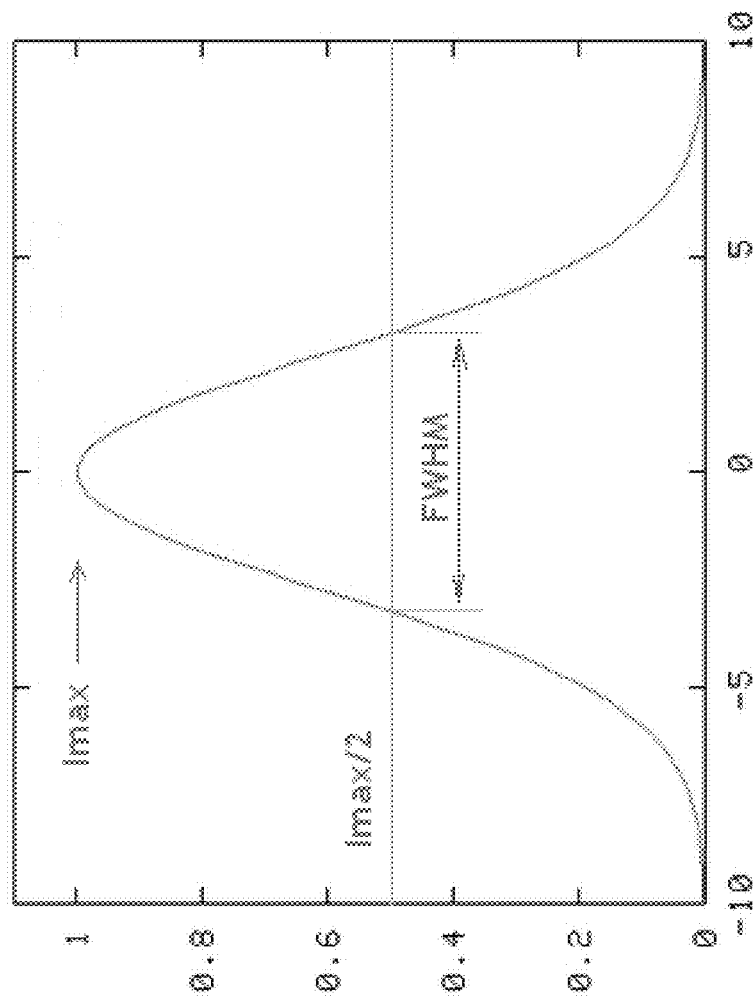
FIG. 6 is a graph illustrating a Gaussian-like peak (PRIOR ART).
Figure 8:
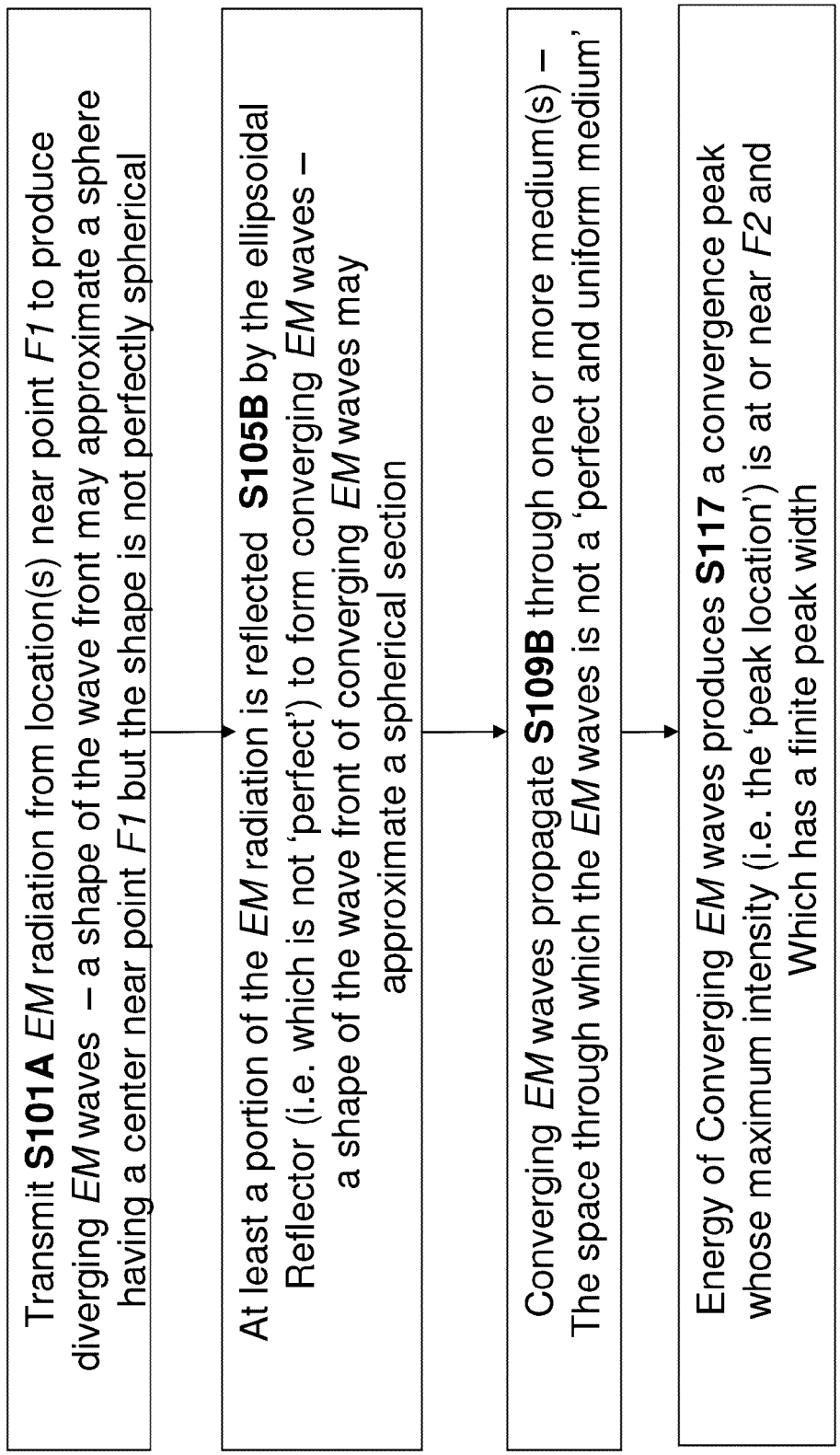
FIG. 8 illustrates a prior art technique for irradiating.

The ellipsoidal reflector 110 and the 'small' radiation source 135 located F1 121 of reflector 110 in FIG. 15 are identical as in the system of FIG. 5. Other than the biological tissue, the medium in which the EM waves propagate is also identical to that of FIG. 5—i.e. having a refraction coefficient near 1. In both FIG. 5 and FIG. 15, converging EM waves whose frequency(ies) is less than 10 Gigahertz propagate through a medium whose refractive index is close to one. In both FIG. 5 and FIG. 15, a shape of a wavefront of the converging EM waves is close to spherical when the EM radiation is reflected from the ellipsoidal reflector, indicating a 'good focus' to focus F2 122. This situation prevails in FIG. 15 in regions of space between the ellipsoidal reflector and the biological tissue.

However, in contrast to the Situation B of FIG. 5, in FIG. 15 the biological tissue is present. When converging EM waves cross from the mismatching medium into the biological tissue, the wavefront is distorted by the disparity in refractive indices, and the wavefront shape, which outside of the biological tissue nearly matched a spherical section, becomes distorted. As such, this may 'smear' the focus, causing the peak width W2 to be much larger than what could be observed in FIG. 1.

Figure 17A:
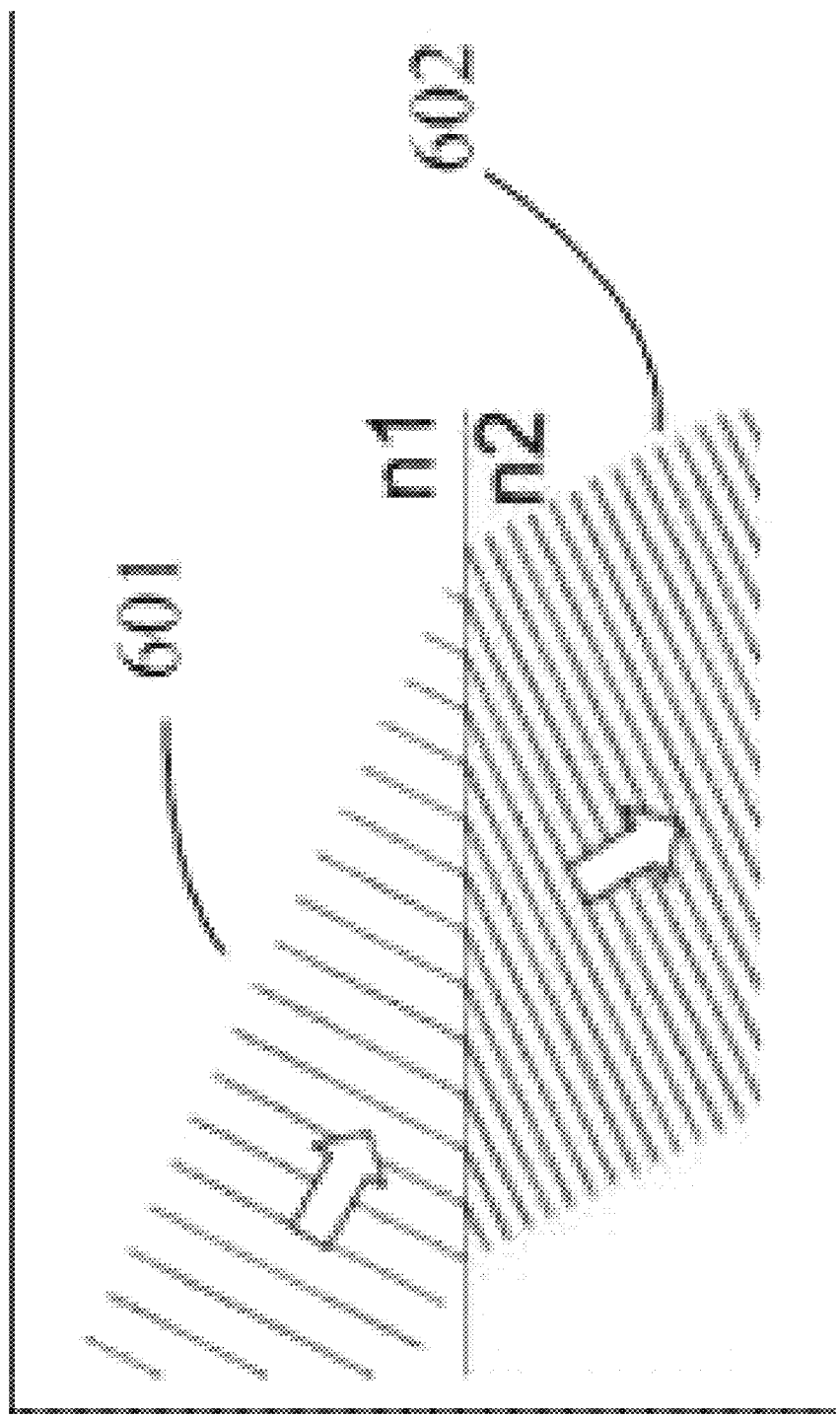
FIGS. 17A-17C and 19A-19B illustrate refraction of EM radiation.

FIG. 17A illustrates, in accordance with Snell's law, deflection of EM radiation that crosses a planar boundary from a first medium having a first index of refraction n1 into a second medium having a second index of refraction n2. The direction of energy propagation is modified from 601 to 602 due to the disparity between indices of refraction.

Figure 17B:
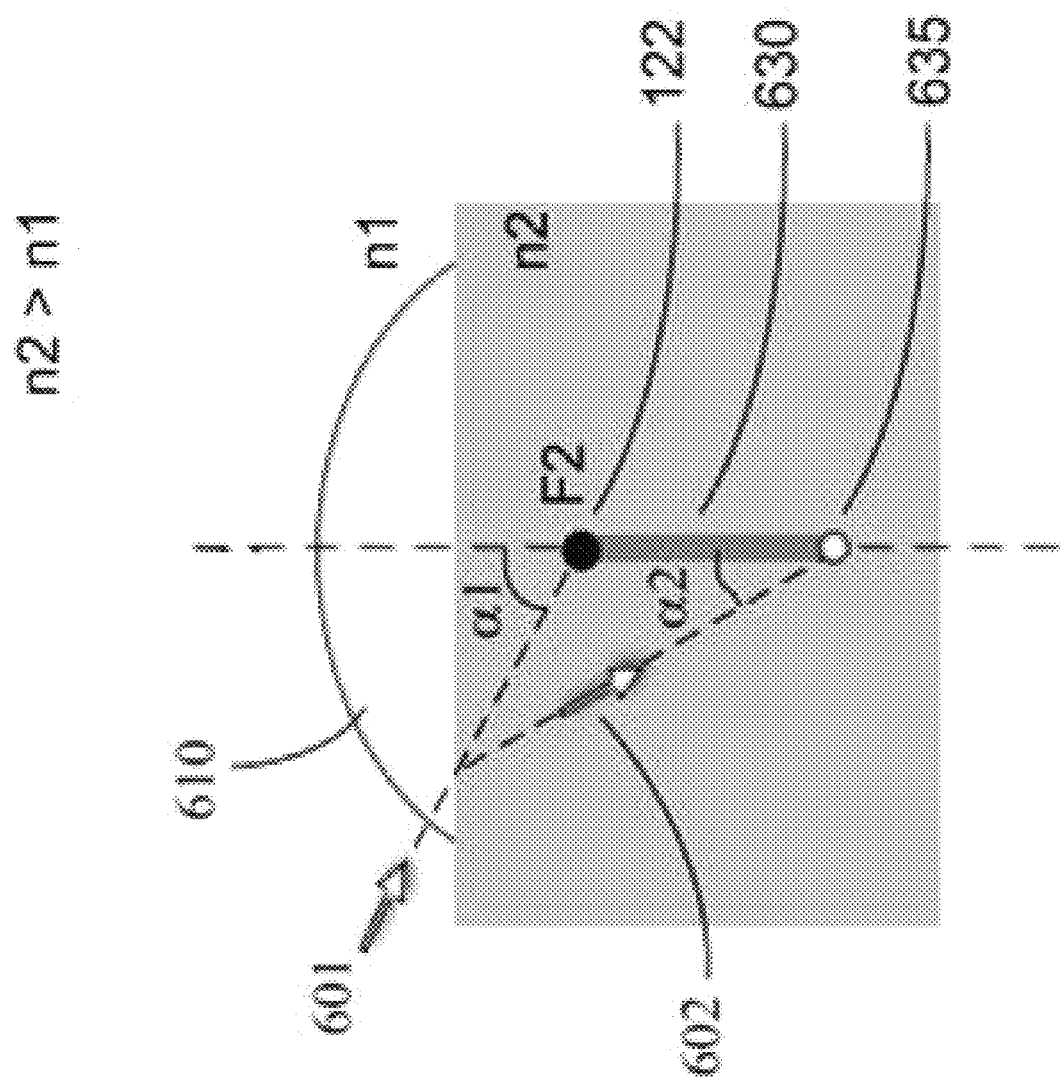

In FIG. 17B, a spherically-shaped wavefront 610 of converging EM waves crosses a planar boundary from a first medium (e.g. a gas such as air or any other 'mismatching' medium) having a first index of refraction n1 (for example, an index of refraction which is differs significantly from that of biological tissue) into a second medium (e.g. biological tissue) having a second index of refraction n2. As was observed in FIG. 17A, for a packet of EM energy whose direction of energy propagation within the first medium is initially is 601, this energy is deflected upon crossing the planar boundary so that a new direction is 602. However, for different location on the spherical wavefront, the amount of deflection will differ since the angle of incidence between the 'initial propagation direction' in the first medium and the interface plane differs as a function of location within the spherically shaped wavefront.

As a consequence, different 'packets' of energy are deflected differently, causing a 'blur' in the focus. If before the EM radiation crosses the planar boundary (i.e. when propagating through the first medium whose index of refraction is n1) the energy is 'tightly' focused around point F2 122 (as was observed in 'Situation B' of FIG. 5), after crossing the planar boundary EM energy is 'smeared' over a region of space that includes line segment 630 between 122 and 635.

Thus, in the example of FIG. 5, the energy density function near focus F2 121 was a 'close to perfect reflection' of the energy density function near the 'small' source of EM radiation 135 located at focus F1 122. Thus, in FIG. 5, a value of an energy density peak width at focus F2 122 was very 'close' to a value of an energy density peak width near the source 135 at focus F1 121. In contrast, in the situation of FIG. 15 and FIG. 17B, the energy density function near focus F2 is a 'very blurry image' of radiation source 121. Thus, even if the radiation source 135 is quite 'small,' due to the 'blurred image' caused by the disparity of refraction indices the peak width W3 is significantly larger than what would be observed (see FIG. 5) in the absence of the biological tissue.

In the example of FIG. 17B, there is a single 'medium crossing event'—a wavefront of energy 610 (i.e. whose shape is close to spherical) crosses from the first medium (i.e. a 'mismatching' medium 98) having a refractive index of n1 into the second medium (e.g. biological tissue) having a refractive index of n2 via a planar surface. Due to the disparity in refractive indexes, this 'medium crossing event' distorts a shape of the wavefront and blurs an energy focus.

Figure 17C:
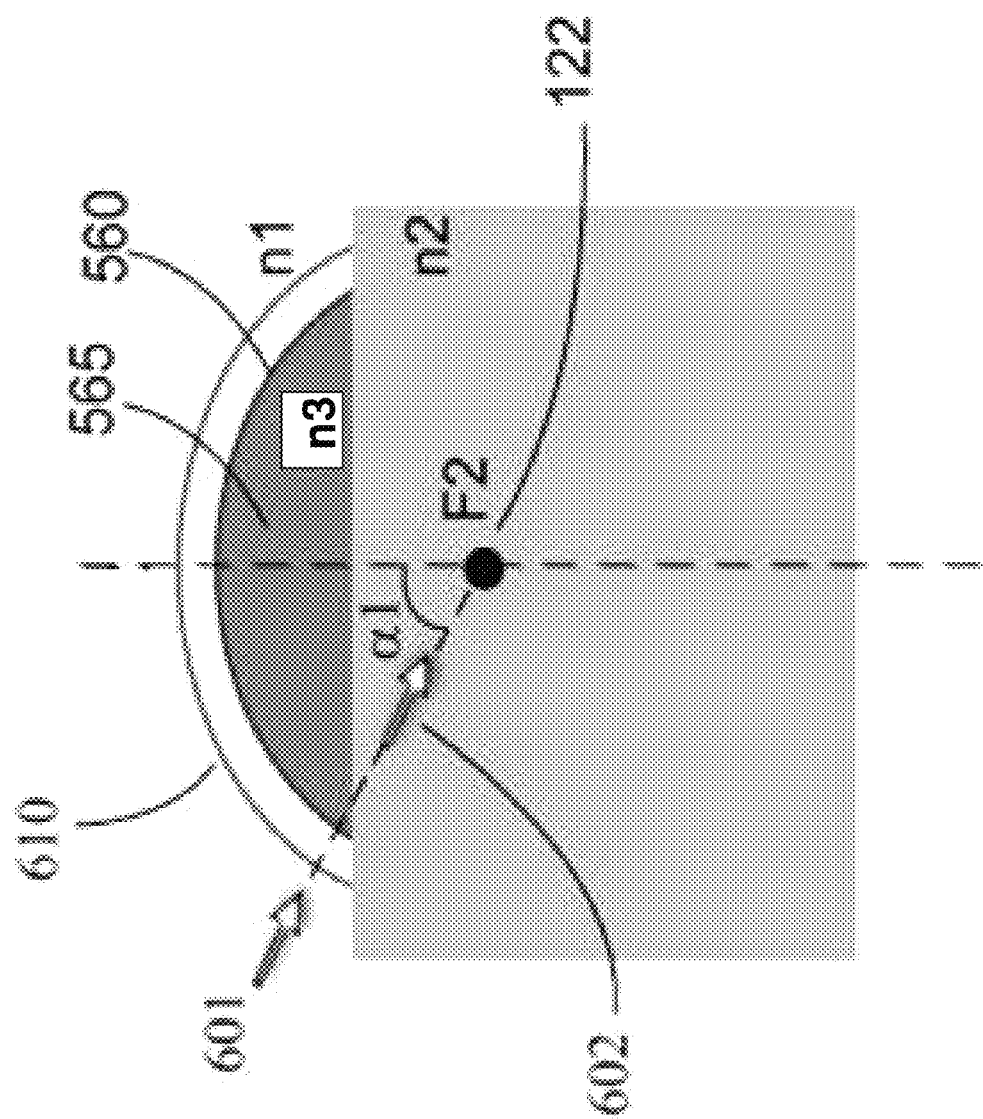
Figure 18:
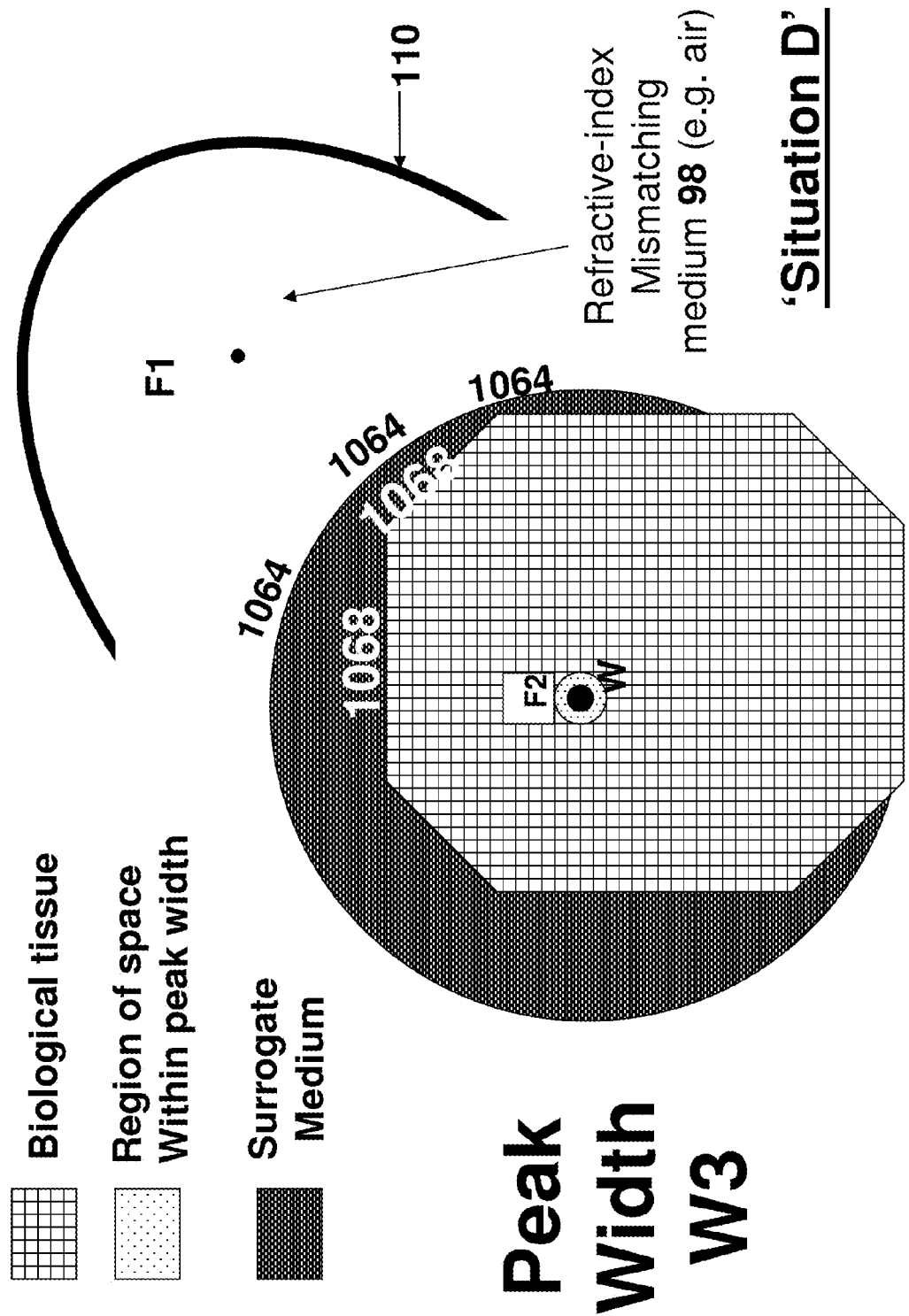

A Discussion of FIGS. 17C-18—Use of Surrogate Medium to Reduce or Eliminate Defocusing Caused by the Biological Tissue The example of FIG. 17C also relates to situation where a converging EM wavefront 610 propagates in a first medium (i.e. a mismatching medium such as air or any gas or any other mismatching medium) whose refractive index is n1 such that a 'future focus location' is a target location F2 beneath a planar surface of a second medium (e.g. biological tissue).

However, in the example of FIG. 17C, the EM energy traverse a surrogate medium 565 having a third index of refraction n3 en route from the first medium (i.e. mismatching medium 98) to the second medium (e.g. biological tissue). In the example of FIG. 18, a refractive index n3 of the surrogate medium 565 substantially matches n2.

In the example of FIG. 17C, there are two medium crossing 'events.' In a 'first medium crossing event,' the wavefront of energy 610 crosses from the first medium (i.e. a mismatching medium 98) into surrogate medium 565 (i.e. a 'matching medium' since its refractive index n3 substantially matches the index n2 of the biological tissue) via a ENTRY_SURFACE 564 of the biological tissue whose shape matches a Poynting vector of the wavefront 610 within the first medium. In the example of FIG. 18, this shape is very close to spherical (i.e. shaped as a spherical section').

In a second 'medium crossing event,' the EM energy crosses from the surrogate medium 565 into the biological tissue via a planar interface.

In contrast with the 'medium crossing event' of FIG. 17B, the first medium crossing event of FIG. 17A does not substantially distort a shape of the wavefront because an angle of incidence of the converging EM waves upon an interface between the first and third media (i.e. a 'mismatching' medium 98 and a surrogate medium 565) is substantially 90 degrees throughout the interface between the first and second media. This is because the ENTRY_SURFACE 564 of the surrogate medium has a shape that matches a Poynting vector of the wavefront 610 within the first medium.

Similarly, the second media crossing event of FIG. 17 also does not substantially distort a shape of the wavefront the refractive indexes of the surrogate medium n3 substantially matches that n2 of the biological tissue.

FIG. 17C corresponds to the example of FIG. 17 for the non-limiting case where the converging wavefront is generated using an ellipsoidal reflector 110 (as noted throughout the specification, this is never a requirement). In the example of FIG. 18 (i.e. 'Situation D') the peak width is W3 which is significantly smaller than the peak width W2 of the example of FIG. 15 (i.e. 'Situation C').

In theory, it is possible to construct a system where the peak width W3 will equal peak width W1 (see FIG. 5). The skilled artisan will appreciate that no surrogate medium is perfect—nevertheless, in different embodiments, the two peak widths will be on the same order of magnitude—for example, a ratio between W3 and W1 will be at most 10 or at most exceed 5 or at most 2.

In some embodiments, when characterizing an 'actual' peak width of converging EM waves delivered to biological tissue via a surrogate medium 565 (for example, see FIG. 18), it is possible to characterize this 'actual' peak width in terms of a first 'hypothetical situation' (for example, see FIG. 5—'Situation B') in the hypothetical absence of the biological tissue and in the hypothetical absence of the surrogate medium. Thus, in some embodiments, the surrogate medium provides a situation where the peak width (e.g. W3 of FIG. 18) is no more than 2 times or no more than 5 time or no more than 10 times what would prevail (e.g. W1 of FIG. 5) in the hypothetical absence of both the surrogate medium and the biological tissue. This is one technique for quantifying how the presence of the surrogate medium can significantly 'cancel out' the defocusing caused by the presence of the biological tissue (e.g. see FIG. 17B).

In some embodiments, when characterizing an 'actual' peak width of converging EM waves delivered to biological tissue via a surrogate medium 565 (for example, see FIG. 18), it is possible to characterize this 'actual' peak width in terms of a second 'hypothetical situation' (for example, see FIG. 17B—'Situation C') in the hypothetical absence of the surrogate medium 565. Thus, in some embodiments, the surrogate medium provides a situation where the peak width (e.g. W3 of FIG. 18) is at most 50% or at most 20% or at most 10% or at most 5% of what would prevail (e.g. W2 of FIG. 17B) in the hypothetical absence of both the surrogate medium.

A Discussion of FIG. 19 and Example values of W2 and W3

Once again, not wishing to be bound by theory, FIGS. 19A-19B relate to a mathematical physics proof and quantification of the defocusing that is observable in situations similar to what was described with reference to FIGS. 15 and 17B.

Figure 19A:
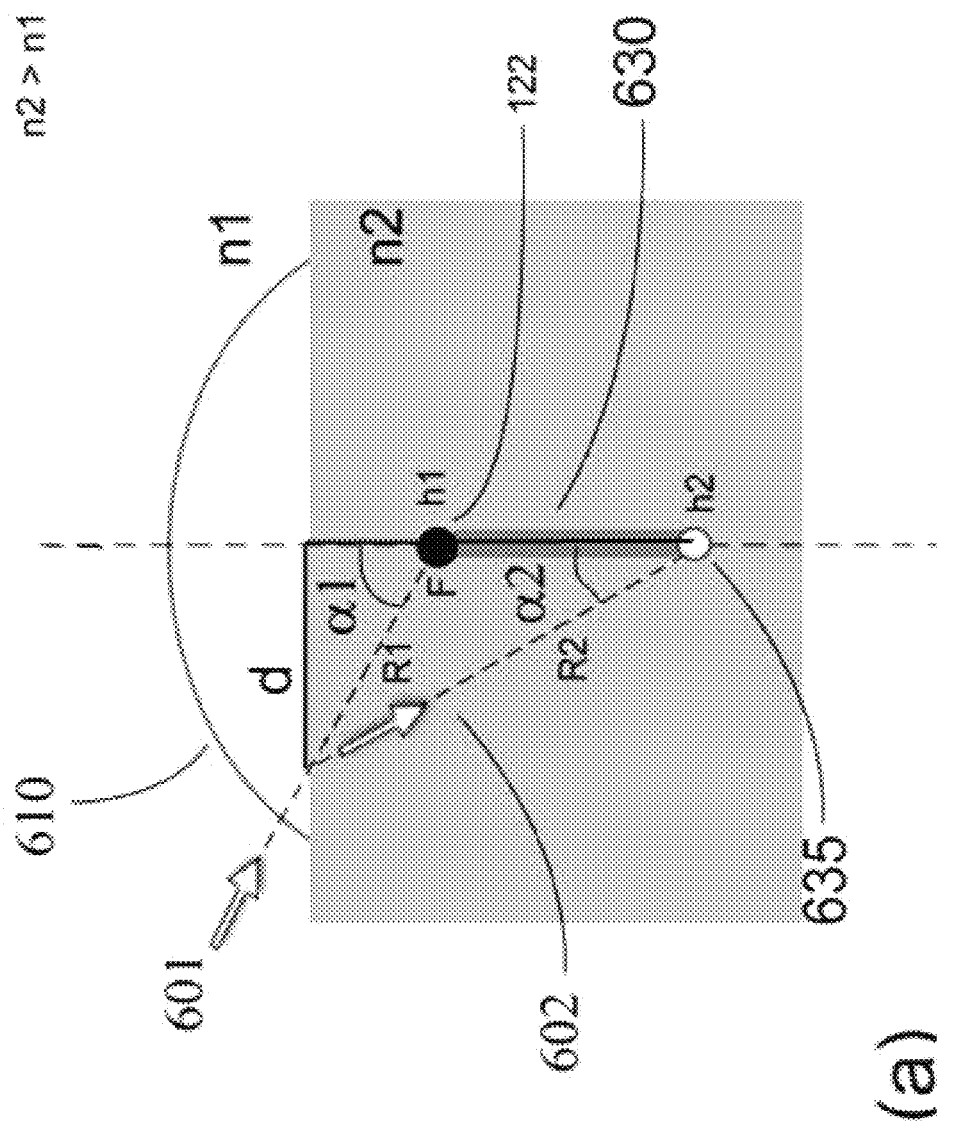
Figure 19B:
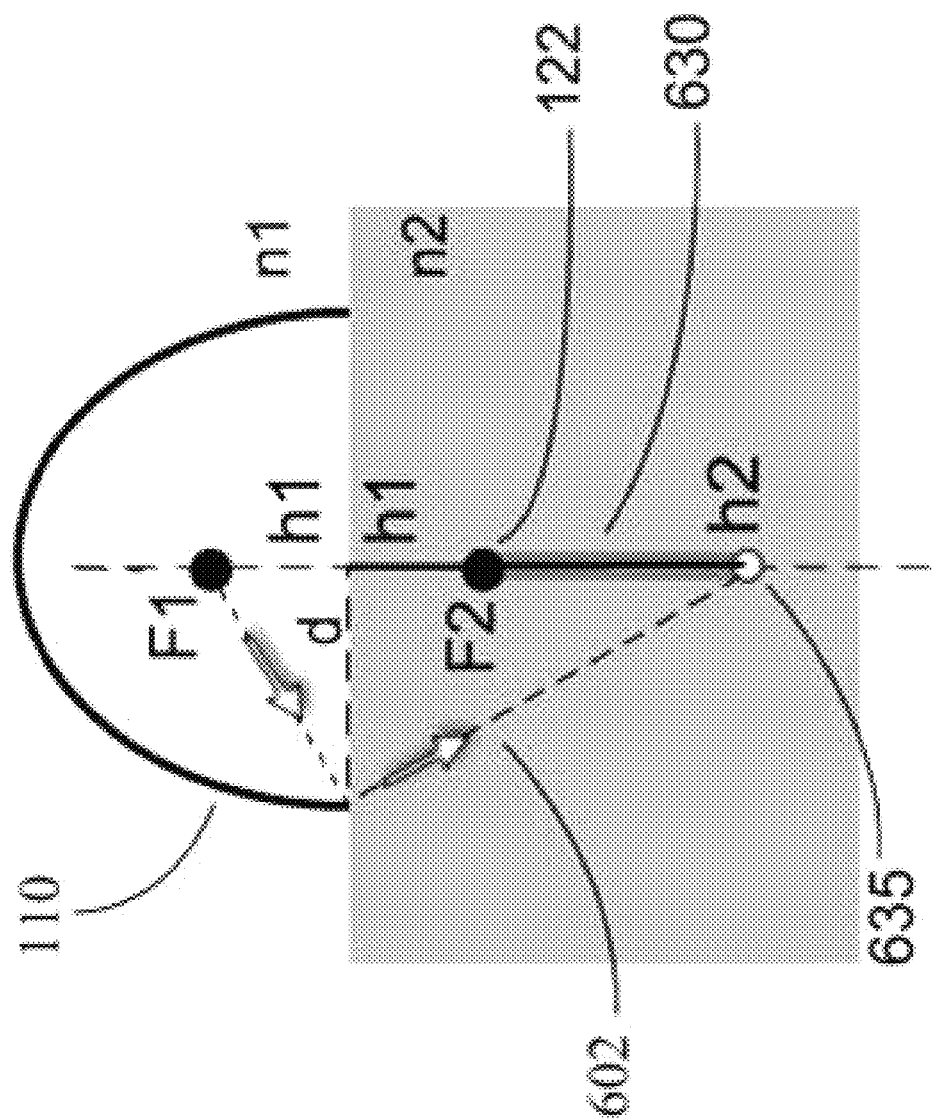
Figure 21A:
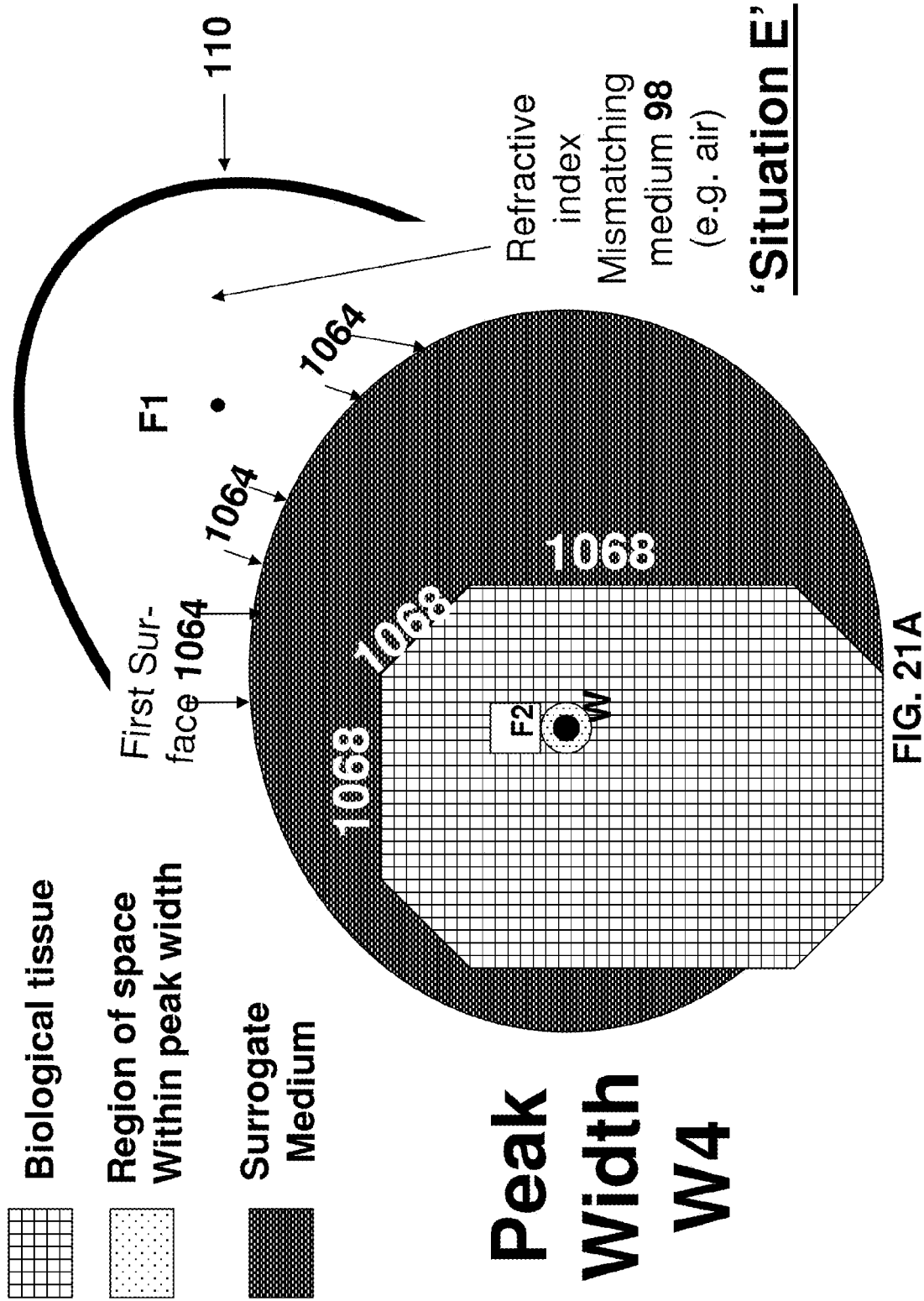
Figure 21B:
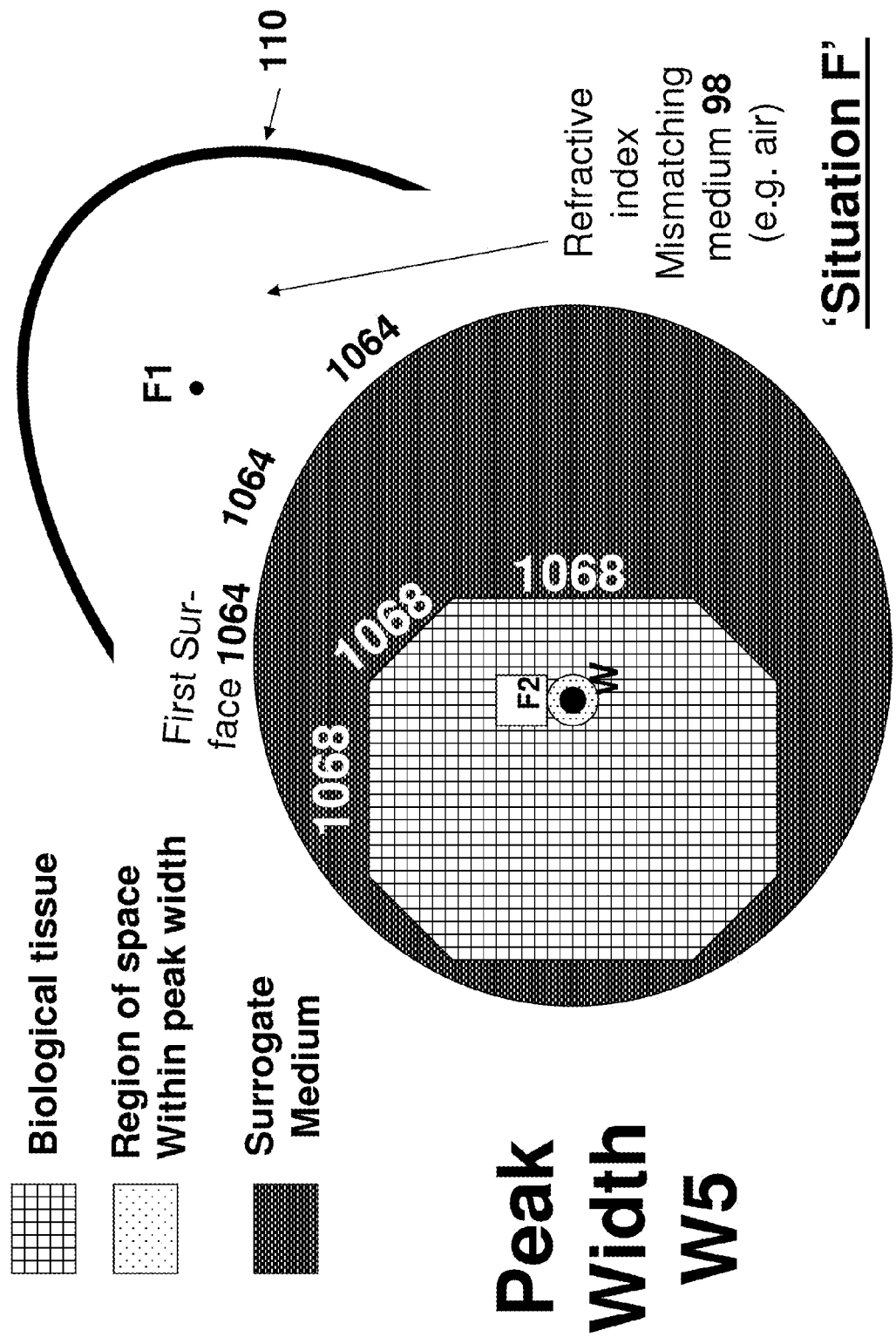
Figure 21C:
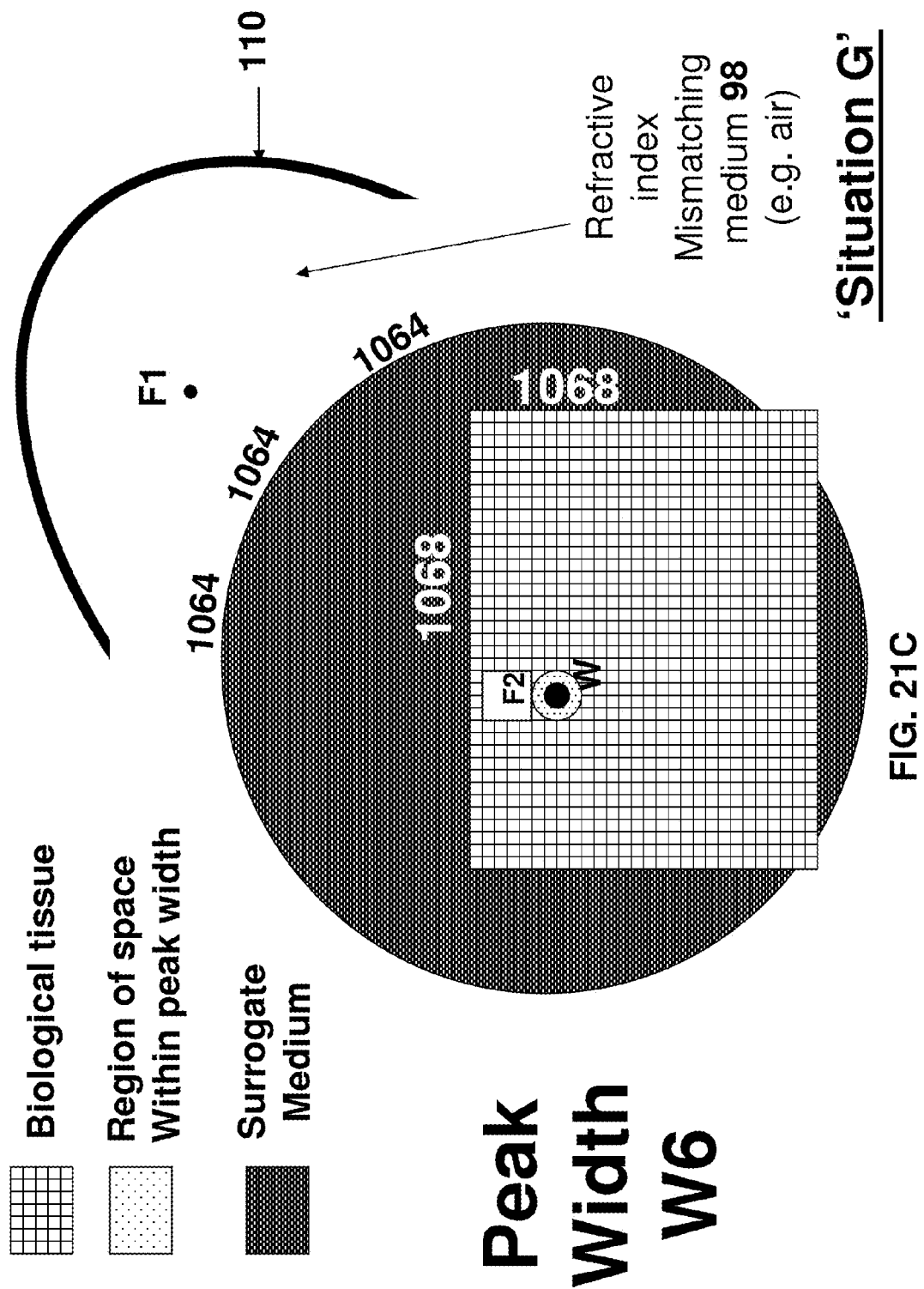

In FIG. 19(a), an exemplary spherical wave front 610 is coming from medium n1, such that its motion is convergent towards its geometrical center at the focal point "F" if unobstructed. Yet, when coming through the flat boundary between medium n1 and medium n2 the spherical wave front will be refracted. We calculated the refraction of a section 601 of the wave front which is arriving at an angle $\alpha 1$ in medium n1, and is refracted to continue moving along a trajectory 602 at an angle $\alpha 2$ in medium n2. Consequently, instead of arriving at the focal point F located a distance h1 below the refracting boundary, it will arrive at a location distance $h_2$ below said boundary. The wave front 601 is crossing the medium boundary at a geometrical distance "d" from the normal to the surface from the focal point F. We now calculate the dependence of the distance $h_2$ on d, i.e., find the functional form of $h_2(d)$.

Using the law of refraction: $\sin(\alpha 2)/\sin(\alpha 1) = (n1/n2)$

By geometry (Fig. 19A): $\sin^2(\alpha 1) = d^2/[d^2 + (h_1)^2]$ $1/\sin^2(\alpha 1) = 1 + (h_1)^2/d^2$ $h_1 = d\cos(\alpha 1)/\sin(\alpha 1)$ -continued $$h_2 = d\cos(\alpha 2)/\sin(\alpha 2)$$

$$(h_2)^2 = d^2[1/\sin^2(\alpha 2) - 1]$$
$$= d^2(n2/n1)^2/\sin^2(\alpha 1) - d^2$$
$$= d^2(n2/n1)^2/[1 + (h_1)^2/d^2] - d^2$$
$$= (n2/n1)^2(h_1)^2 + [(n2/n1)^2 - 1]d^2$$

Thus we find that the wave front 601 is arriving to distance $h_2$ instead of arriving to the focal point F at distance $h_1$ below the boundary surface, where $$(h_2)^2 = (n2/n1)^2(h_1)^2 + [(n2/n1)^2 - 1]d^2 \quad \text{(Eq. 8)}$$

We make the following observations: (a) If the two mediums have the same index of refraction, n2=n1, then h2=h1 independent from d, i.e., indeed every part of the incoming spherical wave front is arriving to the focus point F. But, (b) if n2>n1 then each part of the wave front arrives at a different distance h2 depending on d.

In one non-limiting example, it is possible to utilize the equations above to roughly quantify the amount of defocusing (see FIG. 17B) for a situation where: (i) the biological tissue surface (e.g. skin surface) is perfectly planar; (ii) the index of refraction n1 of mismatching medium 98 is exactly 1; (iii) the index of refraction of the biological tissue n2 is about 10 which approximately matches what prevails for microwave radiation (see FIG. 1); (iv) the ellipsoidal reflector 110 is exactly a half ellipse where the boundary surface between the mismatching medium 98 and the biological tissue lies exactly midway between the two focal points F1 and F2 and is distanced from both foci by 5 cm (i.e. h1=5 cm; d=5 cm); (v) the radiation source 135 has a location that sufficiently corresponds to the first focus F1 and has a size the is 'small enough' so that it may be assumed that the wavefront shape within mismatching medium 98 is exactly spherical (i.e. shaped like a spherical section.

Substituting these values into the above equation, we find the spread of defocusing to be estimated as $$(h_2)^2 = (n2/n1)^2(h_1)^2 + [(n2/n1)^2 - 1]d^2$$
$$= (10)^2(5)^2 + [(10)^2 - 1]5^2$$
$$(h_2)^2 = 199 * 25$$
$$h_2 > 60 \text{ cm}$$

i.e., more than 50 cm smearing of the radiation focus.

This gives an 'order of magnitude' approximation of what prevails in FIG. 15 (i.e. 'Situation B')—i.e. W2 is on the order of magnitude of 50 cm.

Embodiments of the present invention relate to situations where the peak width (see, for example, FIG. 18) is significantly smaller—for example, on the order of magnitude of 5 cm (e.g. less than 10 cm) or on the order of magnitude of 1 cm (e.g. less than 5 cm or less than 2 cm) or even smaller.

DEFINITIONS

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

Biological Tissue Index of Refraction—

At a given frequency of EM radiation, different biological tissues have somewhat different index of refraction (typically about 10% variance mostly dependent upon water content of the tissue). Hence, to first order, any number within 10% of a given representative human tissue can be taken as standing for 'Biological tissue index of refraction'. In preferred embodiments 'Biological tissue index of refraction' can be taken as some calculable or representative average number within the range of human tissue index of refraction. For example, averaging over all body tissue, or averaging over the tissue layers specifically on the path from skin surface to a representative target within the body.

Refractive Index Mismatch—

Embodiments of the present invention relate to irradiating biological tissue of a human subject via an index-matching 'surrogate medium.' As is evident from FIG. 1, for frequencies of interest (e.g. at most 10 Gigahertz) the refractive index of air is about 1 ($n_{air}$~1) while the refractive index of biological tissues $n_{bio}$ is typically more than 2 times the refractive index of air. Thus, there is a large mismatch between the refractive index of air and biological tissue— the ratio between $n_{bio}$ and $n_{air}$ is greater than 2, which cause large angular refraction of EM wave fronts crossing from one to the other.

Stated generally, if for a specified frequency (i.e. a specified frequency less than 10 Gigahertz), a first medium (e.g. a medium 98 in which converging EM waves propagate before reaching a surrogate medium) having refractive index n1 is a medium that is 'refractive-index-mismatching' relative to a second medium (e.g. biological tissue) having a refractive index n2, this means that, for the specified frequency, a ratio between (i) greater refractive index (i.e. max(n1,n2)); and (ii) a less refractive index (i.e. min(n1,n2)) is at least 'M', where M defines the mismatch criterion. For the purpose of the propagation from air into biological tissue at frequencies less than 2 GHz we set M=2. If a first and second medium are designated as 'refractive-index-mismatching' and no frequency is specified, this ratio may be minimized with respect to frequency for all frequencies less than 10 Gigahertz.

Refractive Index Matching—

For the purpose of the invention a surrogate medium 'Refractive index matching' $n_1$ is first of all matching in the sense that it is better matching than air in that $(n_{bio}/n_1)<(n_{bio}/n_{air})$. Thus, if two medium have a 'matching refractive index' there is no requirement for an exact match. Yet, there is advantage for greater equality between the two mediums (i.e., a ratio closer to 1). It is appreciated that the 'refractive index' of a given material is taken as a bulk averaged property.

If for a specified frequency (i.e. a specified frequency less than less than 10 Gigahertz), a first medium (e.g. a surrogate medium 565) having refractive index n1 is a 'refractive-index-matching medium' relative to a second medium (e.g. biological tissue) having a refractive index n2, this means that, for the specified frequency, the ratio of (i) the greater refractive index (i.e. max(n1,n2)); to the (ii) the lesser refractive index (i.e. min(n1,n2)) is at most 3 or at most 2 or at most 1.5 or at most 1.3 or at most 1.1 or at most 1.05. If a first and second medium are designated as 'refractive-index-matching' and no frequency is specified, this ratio may be maximized with respect to frequency for all frequencies less than 10 Gigahertz, and the maximum of this ratio must be at most 2 or at most 1.5 or at most 1.3 or at most 1.1 or at most 1.05.

If three medium (i.e. first, second and third medium) are designated having respective refractive indexes n1, n2 and n3, (ordered in increasing magnitude) and it is said that the '$2^{nd}$ medium matches the $3^{rd}$ medium much better than the $1^{st}$ medium' with respect to refractive index), this means that a ratios satisfy the relation (n3/n2)<(n3/n1).

Surrogate Medium—

Embodiments relate to irradiating biological tissue via a surrogate medium—e.g. index-matching surrogate medium. The surrogate medium is situated outside of the tissue of the human subject. Examples of surrogate medium may include solid objects (e.g. a piece of meat), granular materials, soft materials, flowable substances such as liquids, colloids, gels, or foams.

In one example (see, for example, FIG. 11 or 13) the biological tissue is at least partially submerged in a Towable substance' surrogate medium 565. In another example (e.g. see FIG. 14), it is possible to deploy a 'surrogate medium object' outside of a skin of the human subject—for example, resting the surrogate medium object on the patient's skin and/or pressing the object to the skin.

One example of a 'surrogate medium object' (e.g. see FIG. 14) is shaped to having a ENTRY_SURFACE whose shape is determined in accordance with the Poynting vector. For example, a piece of meat may be 'sculpted' so that its ENTRY_SURFACE 564 is as shown in FIG. 14. Another example of a 'surrogate medium object' is a flowable substance within some sort of container—for example, a plastic container (or any other container that is relatively 'transparent' to radiation of a frequency less than 10 Gigaheretz) having a ENTRY_SURFACE shaped in accordance with the Poynting vector.

Depending on the embodiment and context, the 'shape' of a surface of the surrogate medium may thus be determined by a shape of a surface of a solid object that is a surrogate medium object or by a shape of a solid surface which retains a flowable surrogate medium object—for example, an outer surface of lid 960 or by a shape of a container in which a flowable surrogate medium is contained.

Spherical Shape—

When a something (e.g. a wave front or a surface) has a shape that is 'spherical' this does not require the entire sphere or that an entire sphere surface is present—a spherical section (some partial area of a sphere) is sufficient.

When a visible object or surface is 'substantially spherically shaped' or 'shaped like a spherical section,' this means that upon inspection of the object, it is clear that the object appear spherical—it is possible that deviations from a spherical shape may be detected by an exact measuring instrument. When a wave front is 'substantially spherically shaped,' this means that in the hypothetical situation where the wave front is allowed to propagate in a perfectly uniform medium, the focus is quite 'small'—e.g. at most 5 cm or at most 3 cm or at most 1 cm, or at most 1 mm. Once again, in these examples an entire sphere is not required—a spherical section is sufficient.

Surface Shape 'Matching' to or 'in Accordance with' the Poynting Vector—

A surface shape such that at any point on the surface local normal to the surface is substantially parallel to the local Poynting vector of EM wave crossing at the point. A perfect match is when the surface local normal is everywhere exactly parallel to the local pointing vector. Yet we use the terms 'match' and 'in accordance' to mean substantially close to parallel, i.e., a deviation angle of less than 10 degrees, or less than 5 degrees, or less than 1 degree from parallel over all the surface. A total surface can be considered as having a 'match' to the pointing vector if at least a significant portion of it is matching in the above noted sense, e.g., when at least 50% of it is matching.

As a first example: given a converging EM radiation of spherical section wavefront having its convergence focus centered at location F2, a perfectly matching surface is any spherical section whose arc center is also at F2. A surface with relatively slight deviating center spherical section arc from F2 may still have substantial enough match according to our definition.

As a second example: given a converging EM radiation of elliptical wavefront having its convergence focus centered at location F2, a perfectly matching surface is any elliptical section whose arc center is also at F2 and having the same eccentricity as the EM wavefront at the surface location. Yet, if the eccentricity of the elliptical wavefront is relatively small (as is indeed the case for wavefront at a distance from a small finite size emission source) then a spherical section surface whose arc center is also at F2 can qualify as having a substantial enough match according to our definition.

Peak Location—

The location of maximum intensity of energy density distribution.

Peak Width—

Some embodiments relate to a 'peak width.' As was explained above with reference to FIGS. 7A-7B, a 'peak location' of an energy density function is the location of maximum energy density. To determine the peak width, one needs to examine the region of space surrounding the 'peak location' where the energy density is at least one half of the maximum—the 'peak width' is the diameter of the smallest circumscribing sphere that circumscribes this 'region of space.'

Focus Location—

The neighborhood within peak width around the peak location.

It is noted that for every point in time and for every location, a converging EM wave is associated with a Poynting vector that describes, for that point in time a peak width and a focus location. As a converging EM wave encounters different local refractive index media condition, this may increase a peak width and/or modify a focus location. However, it is possible to speak of a peak width and/or a focus location (i) before converging EM waves move into different medium (e.g. some sort of 'initial conditions') and (ii) after the EM waves move into different medium (i.e. which may increase a peak width and/or move a focus location).

Source of EM Radiation—

Embodiments of the present invention relate to an EM radiation 'source' for transmitting EM radiation into some sort of medium (e.g. a mismatching medium 98 as in FIGS. 13-14 or an index-matching surrogate medium such as in FIG. 11). In a first example, it possible to directly deploy into the medium an antenna array of one or more antennae as the 'radiation source.' In another example, it is possible to generate EM radiation at a remote location and to send the EM radiation to a EM radiation 'source location' via a waveguide. In this example, the source location relates to the end of the waveguide where the EM radiation may propagate within the medium.

The antenna array of one or more antennae may include any antenna known in the art—for example, a line or a coil or any other shaped-antenna.

Since there is no 'point-sized' source of EM radiation, a radiation source 'size' is some sort of characteristic length of a non-point sized radiation source. Similarly, a 'location' 135 of an EM radiation source refers to the location of its centroid—for example, a center of a coil.

Ellipsoidal Reflectors—

Figure 9:
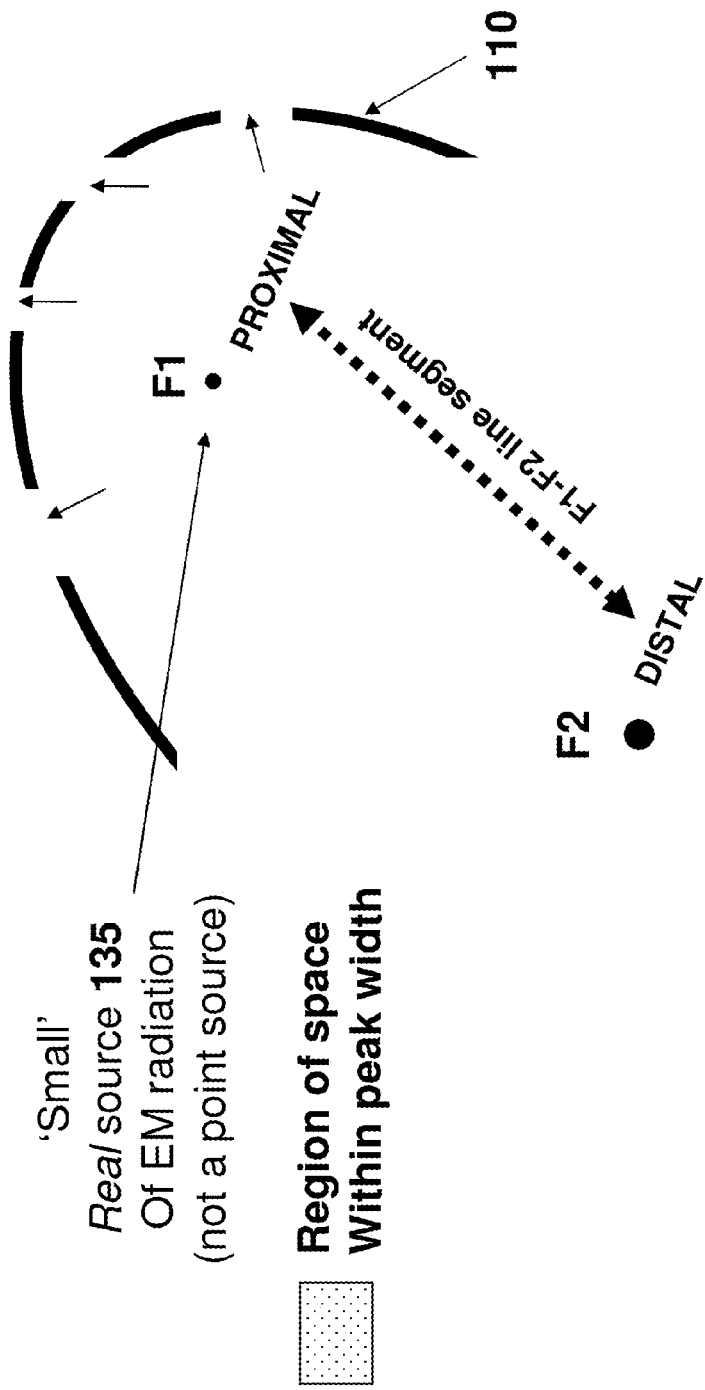
FIG. 9 illustrates a prior art system for irradiating.

Embodiments of the present invention relate to employing an 'ellipsoidal reflector' 110. As is clear from the figures, there is no need to use an entire ellipsoid (i.e. this was the case in FIG. 3)—it is sufficient to employ a portion of an ellipsoid (for example, see FIGS. 5 and 11 and 13-14). Furthermore, as is evident from FIG. 9, there may be any number of voids within the ellipsoidal reflector.

As illustrated in FIG. 20A and FIG. 20B, ellipsoidal reflectors 110 are 3D mirror structures. Examples of ellipsoidal reflector include (a) an ellipsoid generated by rotating an ellipse about the axis connecting the two focal points, as illustrated in FIG. 20A, or (b) a "longitudinal ellipse" generated by parallel transporting an ellipse along a line path, as illustrated in FIG. 20B.

A salient feature of an ellipsoidal reflector 110 is that there are two foci having a finite distance from each other. In different embodiments, a distance |F2-F1| between the focii F1 121 and F1 122 of an ellipsoid defined by the ellipsoidal reflector is at least 3 cm or at least 5 cm or at least 10 cm or at least 20 cm and/or at most 100 cm or at most 50 cm. A mathematical elliptical surface is also characterized by the semi-major and semi-mirror axis. In preferred embodiments of the present invention, both the semi-major and semi-mirror axis are larger than 5 cm and smaller than 100 cm.

In some embodiments, a peak location or target location produced by the converging EM waves is 'substantially at' one of the foci—this means that a distance between the 'peak location' and the foci is at most 10% or at most 5% or at most 2.5% or at most 1% of the distance |F2-F1| and/or at most 2 cm or at most 1 cm or at most 5 mm or at most 2.5 mm.

Location and Size of Radiation Source 135 for Some Ellipsoidal Reflector Embodiments—

Figure 3:
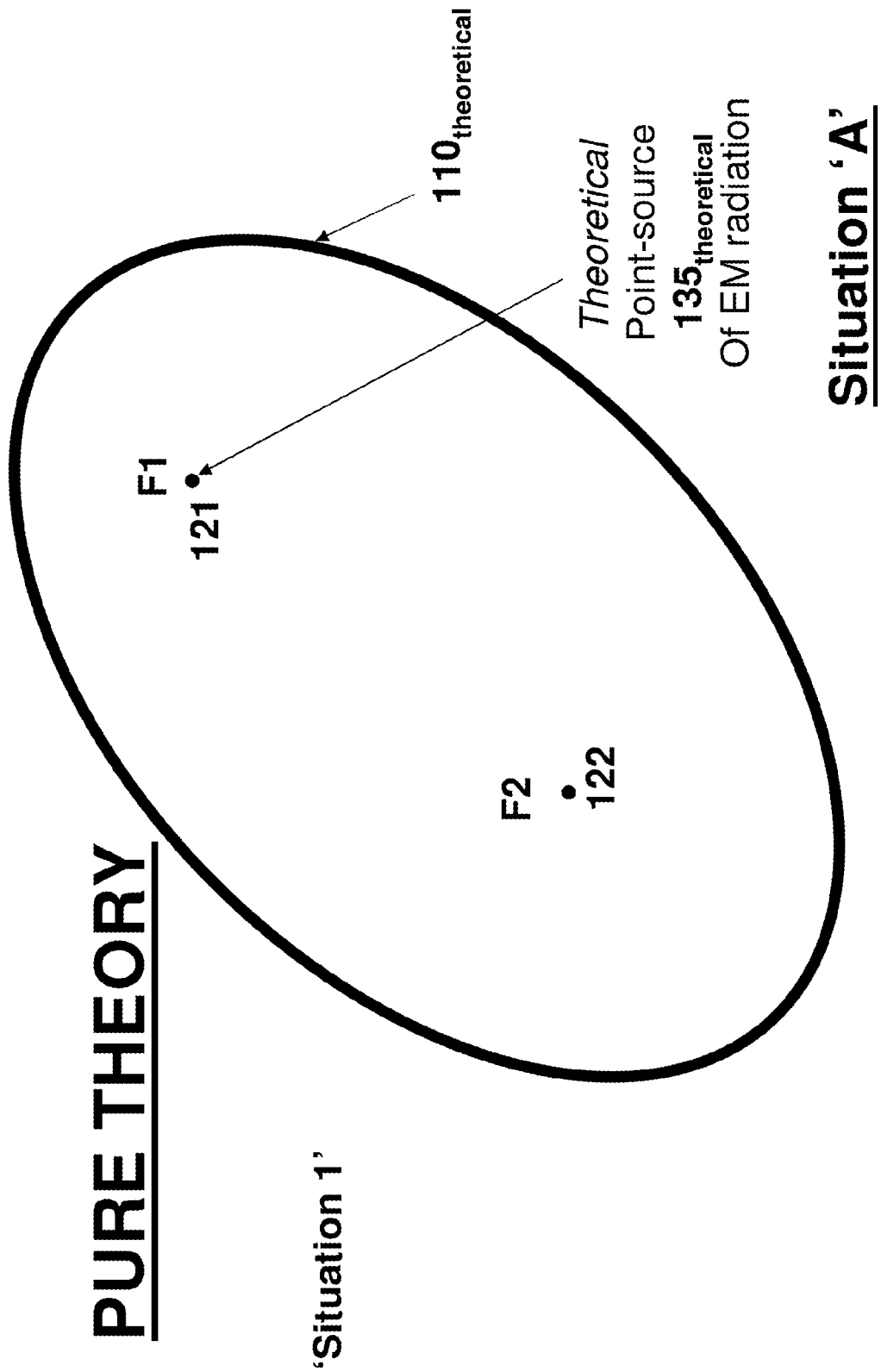
FIG. 3 is a system illustrating a 'pure theory' case (PRIOR ART).

Comparing FIGS. 3 and 5, it is noted that there is no exactly 'point-sized' source of EM radiation. Nevertheless, it is possible to deploy source that is 'small' (i.e. 'point-like') at a location that 'substantially corresponds' to a location '121 of one of the foci F1. A real radiation source is having of physical distribution over some special volume. The location of the source can be considered as represented by its center of mass. For example, a ring antenna location can be associated with its geometrical center (though there is actually no wire material there).

When a source 135 of radiation deployed relative to an ellipsoidal reflector 110 is 'small' this means that the size of the radiation source 135 is significantly less than a characteristic dimension of the ellipsoid defined by the ellipsoidal reflector 110. In different embodiments, this means that a ratio between a 'size' of the radiation source 135 and a diameter of the ellipsoid at the plane of the focal point F1 is at most ⅕ or at most 1/10 or at most 1/20.

When a source 135 of radiation is 'deployed to provide a tight focus' this means that the source 135 of radiation is small enough and deployed close enough to the focus F1 such that in the hypothetical situation where the ellipsoidal reflector has no defect and the medium is perfectly uniform, a source of radiation will produce an energy density peak (i) whose location is displaced from F2 by at most 20% or at most 10% or at most 5% or at most 1% of the distance |F2-F1| between F1 and F2; and (ii) whose peak width is 'small'—i.e. less than 5 cm or less than 3 cm or less than 1 cm or less than 0.5 cm or less than 30% of distance |F2-F1| or less than 20% of distance |F2-F1| or less than 10% of distance |F2-F1| or less than 1% of distance |F2-F1|.

Depth of a Target Location Beneath a Tissue Surface—

The depth of a target location beneath a surface of biological tissue is the minimum distance between the target location and the skin surface.

Resonance Frequency—

Resonance is a response property that is associated with a peak having a peak center and a band width around the center. The resonance band is commonly defined as the range of frequencies within the full width at half maximum (FWHM) of the resonance peak. Thus the term 'resonance frequency' or 'at resonance' should be understood to mean any frequency within the resonance band width. In the context of neural electric resonance, exemplary detection and resonance band width definition can be found in J Neurophysiol 79:1592-1596, 1998 article by L. Stan Leung and Hui-Wen Yu.

A Discussion of FIGS. 21A-21F

ENTRY_SURFACE relative to focus F1 is relatively fixed, while position of the ENTRY_SURFACE relative to the skin of the human subject may vary. Similarly, these scenarios refer to different tissue geometry and/or to situations where locations at different depths in the same tissue are targets. In all of these scenarios, the 'peak width' obtainable (i.e. assuming proper movement or orientation of the 'ENTRY_SURFACE 1064' even when F1 and/or ellipsoidal reflector 110 move or are re-oriented) does not substantially vary—i.e. does not increase to more than 10 times or more than 5 times or more than 2 times the 'minimum peak width' obtainable for the 'best depth beneath the tissue surface' for the region of the human tissue being irradiated.

Thus, in the examples of FIGS. 21A-21F, the radiation is delivered in a manner such that a peak width is substantially independent of a position of the 'peak location' within the biological tissue.

Figure 22A:
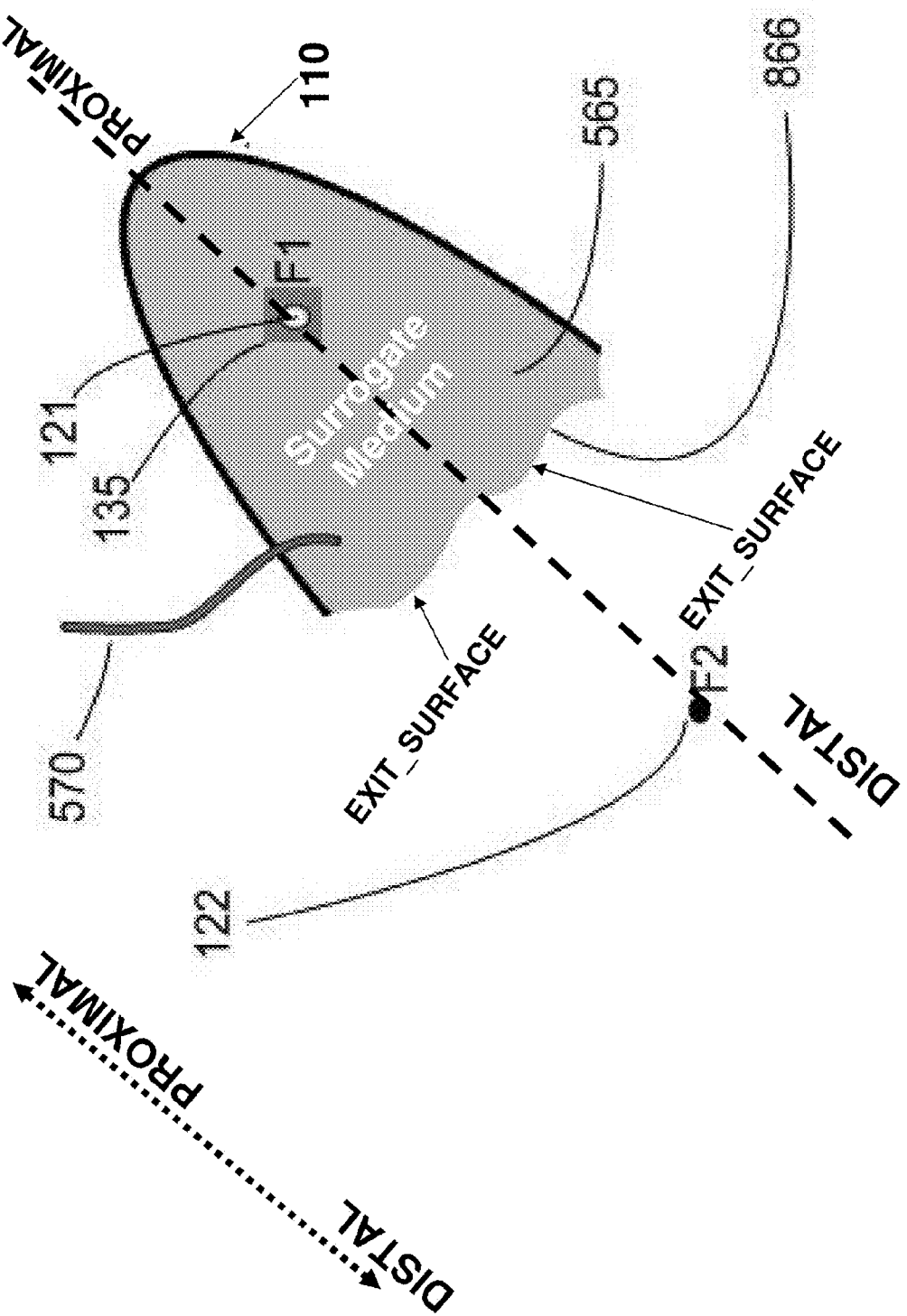
Figure 22B:
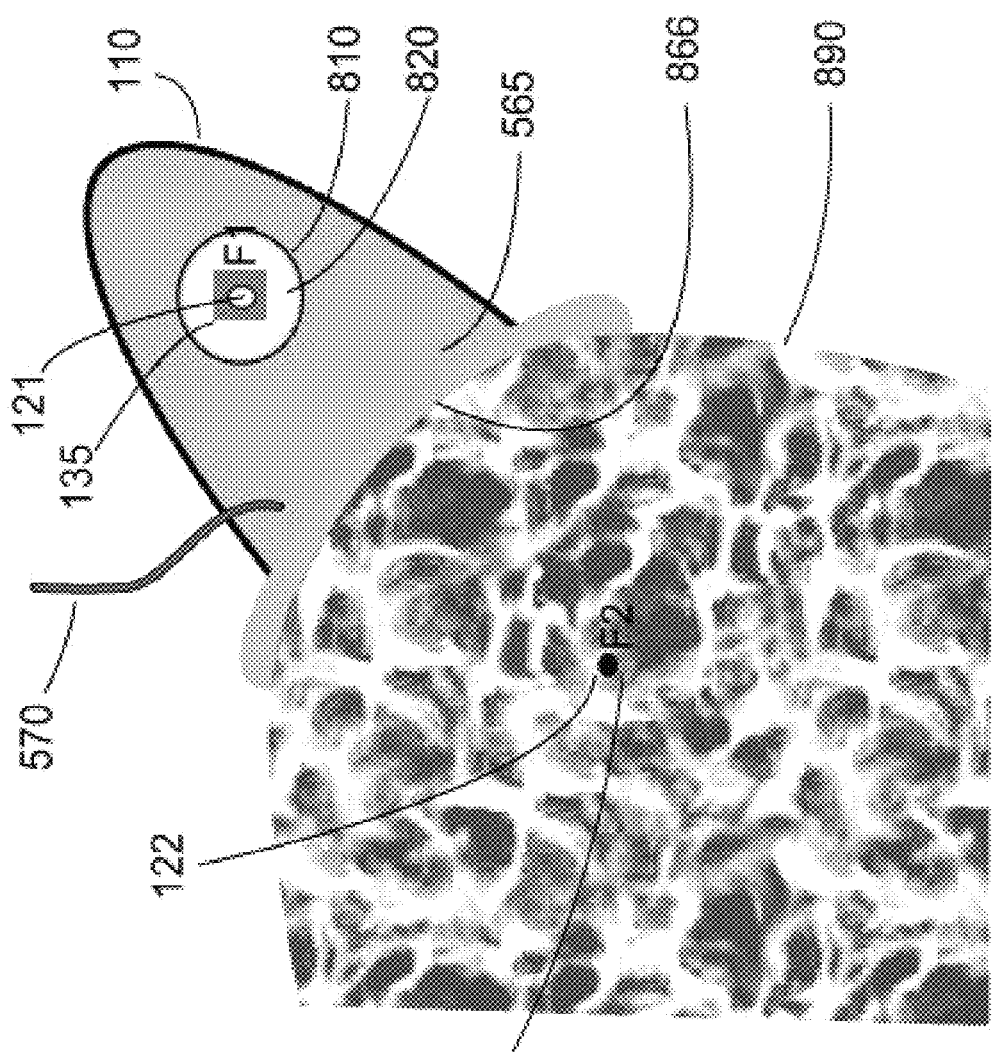

A Discussion of FIGS. 22A-22B

FIGS. 22A-22B illustrate a majority where the surrogate medium 565 fills a majority of the volume between the elliptical reflector 110 surface and patient body 890. In some embodiments, the surrogate medium 565 fills at least the portion of the ellipsoidal reflector 110 proximal to F1.

Surrogate medium 565 includes EXIT_SURFACE 866 via which converging waves of EM radiation exit. In some embodiments, i. at least 30% or at least 50% of power of the converging EM waves pass at the selected one or more frequency(ies) pass through the EXIT_SURFACE; and ii, an average refractive index $n^{AVERAGE}_{SURROGATE\_MEDIUM}$ of the surrogate medium equals at least a minimum refractive-index threshold value that is at least 2 (or at least 3 or at least 4 or at least 5 or at least 6 or at least 8).

In some embodiments, EXIT_SURFACE is located distal to F1 and proximal to F2.

In some embodiments, EXIT_SURFACE is convex and/or flat.

In some embodiments, ellipsoidal reflector 110 is part of a shell assembly.

In some embodiments, EXIT SURFACE 866 includes a movable location on the F1-F2 line segment (or on an 'line extension thereof'—i.e. on a line that is collinear with the F1-F2 line segment—e.g. at a location distal to focus F2) between foci F1 and F2 that is movable relative to the ellipsoidal reflector over a range of at least 2 mm or at least 5 mm or at least 1 cm or at least 2 cm along the F1-F2 line segment (or along the 'line extension'—i.e. the infinite line collinear with the F1-F2 line segment) For example, to achieve the movability of this 'movable location' on EXIT_SURFACE 866, an inlet/outlet 570 is implemented for transfer of secondary medium material may be provided.

First Additional Discussion

The present invention delineates methods and devices for non-invasive generation of concentrated electric fields within a subject animal body using electromagnetic field sources placed outside of said animal body. Said sources, placed externally of the body, are operable to induce electric currents within the body of that subject and particularly in the brain.

Embodiments of the method apply a generation of contracting sections of squai spherical wave fronts. In preferred embodiments, further introducing an index of refraction mediating medium between the human subject body and the radiation source.

In some embodiments, the invention method of is based on generating a concentrating section of quasi-spherical wave front by: introducing a relatively small source 135 emitting electromagnetic waves (e.g., an emission antenna, optical fiber, etc. . . . ) outside of a subject body 190; and placing said source at one of the geometric focal points (F1) 121 of a section of an elliptical mirror 110, reflecting at least a portion of the emitted radiation from said elliptical mirror 110; placing the a body part 190 of a human subject in a location such that a desired pre-selected body region of the subject is located at the second geometrical focal point (F2) 122 of said elliptical mirror 110; thereby creating a focused image of the source 135 radiation at the region of said F2 focal point within the body of said subject animal. The smaller is the radiation source 135 the closer to ideal spherical is the produced wave.

We note with reference to FIG. 1 that the average index of refraction n2 of the human body is in fact frequency dependent, i.e., n2=n2(w) varies with the frequency "w" of the radiation. Commonly all materials index of refraction varies with frequency. The method and apparatus of the present invention are optimized the closer the index matching medium n3 is closer in value to n2 at the particular frequency of electromagnetic radiation in which the device is operated.

For the case that the index matching medium 565 is selected to be water, the graph 565 shows that there is relatively good match between the refraction index n3 of water and the index n2 of a typical human body tissue only above 6.5 MHz. It is expected that the same is true also for saline, plasma, or blood fluids. Therefore, we conclude that in preferred embodiments of the present invention the electromagnetic radiation source is operated at frequencies above 6.5 MHz.

Figure 4:
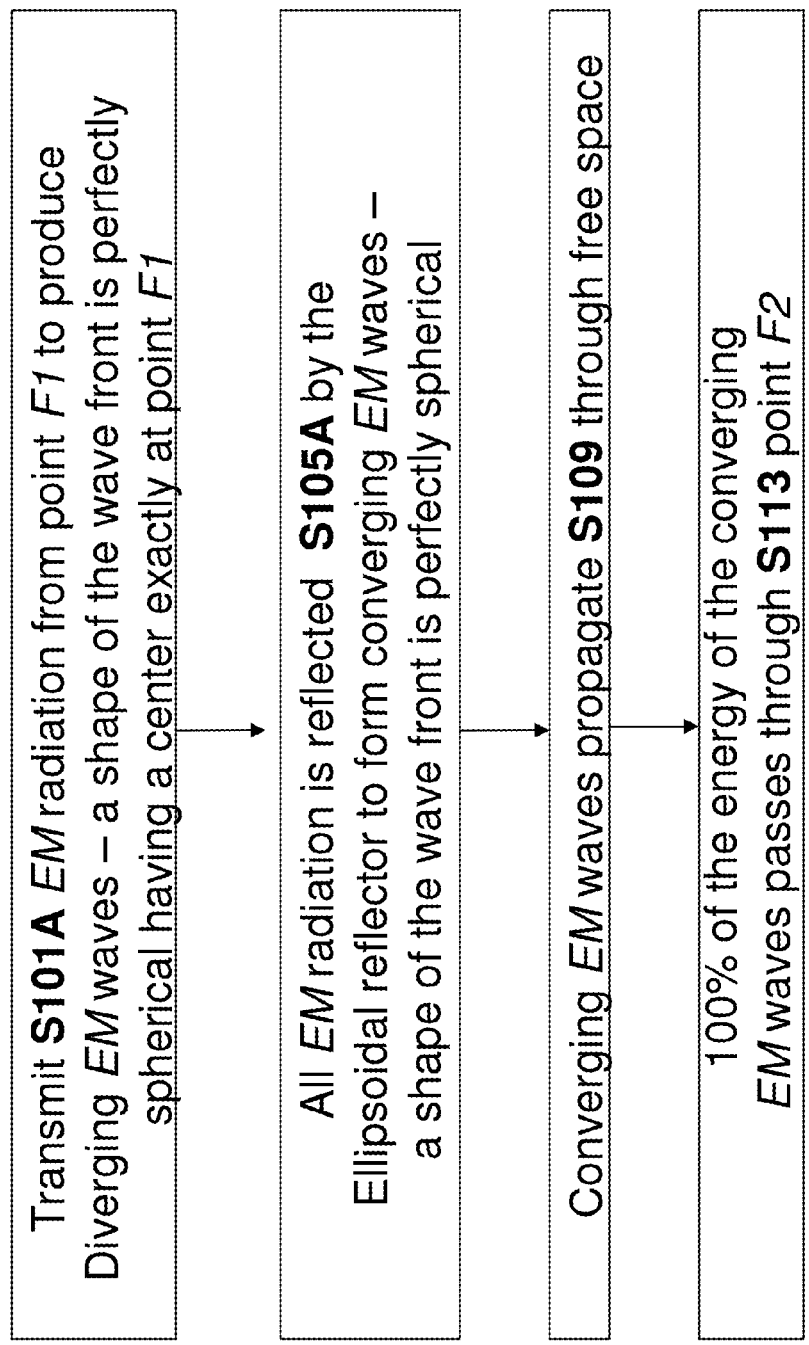
FIG. 4 is a flow-chart illustrating a 'pure theory' case (PRIOR ART).

If particular applications of the present invention call for operation at frequencies lower than 6.5 MHz, then in preferred embodiments the appropriate index matching medium is selected to be such that its index of refraction n3 is matching to the n2 of human tissue at that selected frequency of operation. The putative approximate values of said index n3 can be inferred from the graph of FIG. 4 with the conversion n2~$[Re(\in)]^{1/2}$.

Some embodiments relate to a method of inducing deep brain tissue stimulation (DBS) is based on:

(a) providing an elliptical reflecting surface/mirror 110 (or subsection 110 of an elliptical mirror) having one geometrical focal point F1 and a second geometrical focal point F2; providing a relatively small source 135 capable of emitting radiation of selected electromagnetic waves (e.g., an emission antenna); providing a secondary medium 565 confined under a spherical sub-section shell 560, said spherical shell being substantially transparent to the electromagnetic waves emitted by the source 135;

(b) placing said electromagnetic radiation source 135 at one of the geometric focal points (F1) 121 of said elliptical mirror 110 outside of the body of a human subject;

(c) placing said medium 565 confined under a spherical sub-section shell 560, such that the geometrical center of said shell 560 is coinciding with said focal point F2 of said elliptical reflecting surface 110;

(d) placing a pre-selected body organ region 190 for treatment (e.g., brain region, cancer tumor region, etc. . . . ) of the subject at position overlapping the second geometrical focal point (F2) 122 of said elliptical mirror 110;

(e) adjusting the volume content of the medium 565 such that its bottom surface 566 is tightly conforming to the contact surface of the body of said human subject;

(f) in operation, reflecting at least a portion of the emitted radiation from said elliptical mirror 110; thereby getting the emitted radiation from source 135 to be significantly concentrated at the region of said F2 focal point within said selected body organ region of said human subject.

(g) operating the radiation source 135 emission according to a pre-selected protocol for medical treatment of a pre-selected condition of said human subject; said protocol specifying at least the radiation frequency, intensity, and duration of said radiation In some examples relating to FIG. 14(*a*), in order to hold the confining spherical section shell 560 positioned such that its geometrical sphere center coincides with the geometrical focal point F2 of the elliptical surface 110, there is some form of rigid connector element between them represented by rod 550 in FIG. 5(*a*). The rod shape of the rigid connector element 550 is only illustrative and is not meant to be limiting.

In some embodiments, the secondary medium 565 and/or its container is detachable from said elliptical reflector surface 110, such that it enables interchange of one medium 565 by another, and/or changing of the medium volume, and/or changing of the spherical shell 560 size and/or spherical shell 560 radius.

In position, the spherical shell side of index matching secondary medium 565 is facing towards the source 135 at focal point F1 of the reflecting elliptical surface 110 while the other side of medium 565 is facing towards the other focal point F2 which in operation is to be located within the human subject body. In order to minimize the distortion of the radiation wave front upon entering the human subject body, it is preferred that the secondary medium 565 contour will be as snugly fitting as possible to the contour of the subject body at the contact area. Therefore, as illustrated in FIG. 5(*b*), in preferred embodiments, the side of medium 565 which is facing towards F2 is bounded with a malleable or elastic boundary 566, and the contained medium 565 is itself malleable or elastic. Thereby it conforms to the human subject body contour when pressed against it.

In order for allowing variable positioning of the focal point F2 within a human subject body. Variable sizes of the spherical shell 560 and volume content of the medium 565 is possible. In preferred embodiments, the volume of the medium 565 contained between the shell 560 and bottom boundary 566 can be varied by inflow or outflow of the medium n3 volume via an inlet lumen 570.

In many instances we shall discuss the invention with respect to action targeted at brain tissue. Any such reference to brain stimulation, is not meant to be limiting, and should be regarded as a canonical example to application of the invention in any body tissue in general and nerve tissue in particular.

In particular embodiments, devices according to the invention can be used for focused deep brain stimulation (DBS) of selected brain regions with minimal effect on undesired brain regions. If placed outside the skull of a subject, is capable of stimulating the brain of the subject, including deep regions of the brain. Methods for using this device include treating human subjects with neurophysiological conditions, such as clinical or non-clinical depression, substance abuse, drug addiction, and other uses of DBS as known in the art of electromagnetic brain stimulation.

In order to preferentially stimulate selected deep brain regions, with minimum undesired effect on other brain regions, it key to have concentrated well peaked field. i.e., fields distribution where the field amplitude at the peak region is significantly bigger than away from the peak within the brain.

In addition, the invention relates to methods for inducing particular brain-wave states in selected brain regions.

Generation of said concentrated electric field in the brain can be used to generate local heating of brain regions. Optionally, said local electric fields, currents, and heating can be used to affect local blood clotting during hemorrhage or surgical wounds.

We recognize that the failure of prior art to produce well peaked deep brain electromagnetic fields stems from prior art non-invasive brain simulation reliance on producing an initial distribution of static magnetic fields. In contrast, we use focused electromagnetic waves (i.e., alternating fields) to induce local alternating currents in the brain.

All brain stimulation is actually generated by electric fields, not magnetic fields. In the prior art of so-called "magnetic brain stimulation" (MBS), it is the short duration transient electric fields (generated with a sharp turning off of the static magnetic field) which create the brain stimulation. In contrast, the present invention generates focused alternating electromagnetic fields of any duration and any desired intensity pattern.

In some embodiments, the method of inducing deep brain stimulation (DBS) is based on: introducing a relatively small source 135 emitting electromagnetic waves (i.e., an emission antenna) outside of a subject scull 190; and placing said source at one of the geometric focal points (F1) 121 of an elliptical mirror 110 (or subsection of an elliptical mirror), reflecting at least a portion of the emitted radiation from said elliptical mirror 110; placing the head 190 of an animal subject in a location such that a pre-selected brain region of the subject is located at the second geometrical focal point (F2) 122 of said elliptical mirror 110; thereby creating a focused image of the source 135 radiation at the region of said F2 focal point within the brain of said subject animal.

In some embodiments, local nerve stimulation in prior art was generally reliant on invasive electrode placement at the neighborhood of the target nerve, and influence the nerve activity by currents emanating from the electrode. Such nerve stimulation has found many medical applications. Since electromagnetic fields can induce local currents, in present invention we claim to provide non-invasive method of focusing of electromagnetic to influence nerve activity, and thereby provide non-invasive medical treatment methods to the same ends as with prior art invasive electrodes.

For example, the prior art of brain stimulation described in US patent application 2006/0200206 is comprising of an electrodes implanting procedure; involving positioning first and second electrodes at the identified stimulation site, and a stimulating procedure involving applying an electrical current between the first and second electrodes. Instead, the present invention can be implemented to the same treatment ends, by replacing the electrode stimulation with focused electromagnetic stimulation to convergence focal point F2 positioned to reside at the identified stimulation site.

Moreover, while electrode placement is fixed in place (and any electrode relocation is an added invasive procedure), the present invention convergence focus can be moved from place to place (and even smoothly along a continuous path) with no resistance and no need for repeated invasive procedures.

In preferred embodiments of the present invention for nerve stimulation, the radiation frequency is selected to be at an absorption resonance of said neuronal tissue, i.e., within a range of half-width of a local peak absorption frequency.

A condition for the electromagnetic waves to penetrate to deep brain regions is that the frequency or group of frequencies of the electromagnetic fields is selected to be such that is not significantly attenuated when traveling through the scull and brain tissue. Known examples of such frequency ranges are those of the well known EEG brainwaves bands between 1-40 Hz; and radio waves, from 3 MHz to 10 GHz (3 cm), are also known to be transmitted well though body tissue (e.g., including as in such uses as RFID typical devices). To be precise, the skin depth ($\delta$) is defined as the penetration distance at which the field decreases to 1/e=0.368 of its value just inside the scull boundary surface. Approximating the human body as a "good conductor" we can use the equations $$\delta = \frac{1}{\omega[\frac{\mu\epsilon}{2}(\sqrt{1+p^2}-1)]^{1/2}}, \quad \text{(Eq. 7)}$$

$$p = \frac{\sigma}{\omega\epsilon} \gg 1 \text{ and } \delta = \frac{1}{\sqrt{\pi f \mu \sigma}}$$

The average human body conductivity is $\sigma$=0.5[S/m]. Thus at 1 Mhz the average $\delta \sim 1/[\pi \xi 10^6 \xi 4\pi 10^{-7}\xi(0.5)]^{1/2} \sim 1$ m. From this characteristic value, since the skin depth equation is proportional to $[1/f]^{1/2}$, we can approximate for 100 MHz a skin depth of $\delta \sim 10$ cm, and for 10 GHz a skin depth of □~1 cm. In the published literature (see the book "Electromagnetic Shielding" By Kenneth L. Kaiser) we found that for human fat the range p=0.37 to 1.4 gives a 30 MHz skin depth of about 0.6 m to 2.2 m. Similarly for muscle tissue we found in the literature (Arumugam & Engels, "Characterization of RF Propagation in muscle Tissue for Passive UHF RFID Tags", 2008) the value p=0.59. When p is in this range of values then a better approximation is to take not $\delta \sim [1/f]^{1/2}$ but $\delta \sim 1/f$. Hence, at frequency f=300 MHz we get another estimate skin depth of $\delta \sim 6$ cm to 22 cm. Altogether, we reach the conclusion that for frequencies up to 500 MHz there is good penetration of electromagnetic waves to any location in the human body. Yet, also at around 500 MHz there begins to be significant absorption and therefore heating of body tissue. (for comparison, microwave ovens operate at around 2.5 GHz; cellphones commonly operate at 900 MHz to 1800 MHz bands).

A Second Additional Discussion

In this section, a number of applications are further discussed.

Neural Stimulation—

Field strengths in preferred embodiments are selected such that they produce sufficient induced currents in brain to result in neuronal depolarization.

The electric field developed across the resting membrane of neural cells is around 107 V/m. Hence, it may be required in preferred embodiments that the source fields at the first focal point will be of comparable magnitude. In preferred embodiments, such high fields may be generated by high field capacitors. For example, various ceramic based capacitors can withstand around 1 MV/cm (i.e., 108 V/m) fields, and hence can be suited for use as high field electromagnetic radiation sources.

In preferred embodiments, the source 135 is a magnetic dipole source, such as a coil.

In preferred embodiments, neural stimulation is operated at frequencies corresponding to electromagnetic absorption resonances of the neural tissue. Some selected such resonance frequencies known in the published literature are: brain wave states in the range 4-15 Hz, and resonances in 10-50 Hz and 100-250 Hz frequency bands [Prog Brain Res. 2005; 148:181-8], Highly localized neural stimulation by focused electromagnetic radiation of the present invention can be implementing as non-invasive method to the same application as electrode stimulation of neurons. For example, stimulation of brain blood flow by stimulating selected neurons or neural regions as elaborated in US patent application 20040220644 the content of which is here incorporated in its entirety.]

Brainwaves State Enhancement—

The present invention also introduces a method and apparatus for enhancing particular brainwaves states in local areas of the brain. In use, the elliptical mirror 110 is placed such that the F2 convergence focus 122 is located within the desired target brain area for induction of brain waves. In preferred embodiments, the source is selected to emit one or more frequencies in the ranges of: delta waves lie in the frequency range of 0 to 3.5 Hz; theta waves lie in the frequency range of 4 to 7 Hz; alpha waves lie in the frequency range of 8 to 13 Hz; beta waves lie in the frequency range above 13 HHz; and sensorimotor rhythm (SMR) waves lie in the frequency range of 12 to 15 Hz.

RF Ablation—

The present invention also introduces the first method of non-invasive radiofrequency ablation surgery. The term "radiofrequency (RF) ablation probe" refers to a class of medical devices operating between 460-550 kHz that deliver therapeutic energy into soft tissues. The intent of these devices is to thermally necrose tissue by raising targeted tissue temperatures to approximately 100° C. for a period of 10-15 minutes [1,2]. Instead of present art ablation probes being inserted percutaneously or subdermally (e.g., into tissues where cancerous tumors have been identified), the present invention creates a focused image at a focal point inside the body of a RF source placed outside the body at the other focal point of an elliptical mirror. The elliptical mirror serves to transmit the RF radiation energy from the source to the focal point inside the body. At 500 kHz, liver conductivity is approximately 0.148 S/m. By comparison, liver conductivity at 27 MHz and 2.45 GHz are 0.382 and 1.687 S/m.

Local Hyperthermia—

The invention also introduces a non-invasive method and apparatus of inducing local hyperthermia of cancer tissue, by focusing of electromagnetic radiation. The intent of the electromagnetic radiation hyperthermia devices (preferably operating at 27 MHz or 2.45 GHz) is to raise the temperature of timorous tissues to between 43-45° C. for extended periods of time on the order of hours.

In use, the elliptical mirror 110 is placed such that the F2 convergence focus 122 is located within the desired target human organ for hyperthermia.

Blood Coagulation Stimulation

The invention also introduces a non-invasive method and apparatus for inducing enhanced blood coagulation. In use, the elliptical mirror 110 is placed such that the F2 convergence focus 122 is located within the desired target human tissue for treatment, and where said location is anywhere under the skin. Such target tissue may comprise of surgical cuts, brain hemorrhage, and other internal body parts in need of prevention or inhibition of bleeding.

The radiation source power at F1 is selected so that the power transferred to the F2 convergence focus is such as not to raise the temperature of the surrounding tissues to such high values as to cause collapse of the tissue of the blood vessel. In other words an object is to obtain that the temperature transmitted by the electromagnetic radiation to the tissue to be coagulated never exceeds 70-75° C.

Also advantageously the resonance frequency of radiation is preferably but not necessarily chosen around 4 MHz. In preferred embodiments a combination of other frequencies is employed, e.g., a modulating wave may have the frequency, for instance 50 or 60 Hz or a frequency of 20-30 KHz.

The presence of a spectrum of harmonics in the resulting wave causes the manipulator to transmit a power and therefore an energy to the tissue under coagulation, which is the sum of the different specific energies due to the various frequencies. This is particularly important because at each molecule of the cellular tissue to be coagulated of different nature corresponds an ideal energy to be transmitted to reach in the present case, the correct temperature allowing transformation of the fibrinogen into fibrin without causing damages to the other adjacent cells.

Having thus described the foregoing exemplary embodiments it will be apparent to those skilled in the art that various equivalents, alterations, modifications, and improvements thereof are possible without departing from the scope and spirit of the claims as hereafter recited. In particular, different embodiments may include combinations of features other than those described herein. Accordingly, the claims are not limited to the foregoing discussion.

What is claimed is:

1. A noninvasive method for providing focused tissue stimulation to a human patient, comprising of performing a procedure to determine the location of target tissue at which a desired stimulation is to be performed;

positioning a source of electromagnetic radiation at first focal point of an elliptically curved reflecting surface, placing both said reflecting surface and said first focal point outside of said patient body;

positioning said target tissue to overlap with the second focal point of said elliptically curved reflecting surface;

applying an electrical current signal to said source to generate radiation of electromagnetic radiation at one or more selected frequencies; and continuing said radiation of a predetermined treatment session duration to affect said tissue, wherein the tissue is brain tissue and said desired stimulation is brain waves amplitude enhancement, where said brain waves frequency is in the range of 0 to 20 Hz, and said radiation frequency is in the range of 0 to 20 Hz.

* * * * *